US006907280B2

(12) United States Patent
Becerra et al.

(10) Patent No.: US 6,907,280 B2
(45) Date of Patent: Jun. 14, 2005

(54) METHOD AND APPARATUS FOR OBJECTIVELY MEASURING PAIN, PAIN TREATMENT AND OTHER RELATED TECHNIQUES

(75) Inventors: Lino R. Becerra, Cambridge, MA (US); Hans C. Breiter, Lincoln, MA (US); David Borsook, Concord, MA (US)

(73) Assignee: The General Hospital Corporation, Boston, MA (US)

( * ) Notice: Subject to any disclaimer, the term of this patent is extended or adjusted under 35 U.S.C. 154(b) by 186 days.

(21) Appl. No.: 09/822,585

(22) Filed: Mar. 30, 2001

(65) Prior Publication Data

US 2002/0042563 A1 Apr. 11, 2002

Related U.S. Application Data

(63) Continuation-in-part of application No. 09/729,665, filed on Dec. 4, 2000.
(60) Provisional application No. 60/228,950, filed on Aug. 28, 2000, provisional application No. 60/193,300, filed on Mar. 30, 2000, and provisional application No. 60/168,660, filed on Dec. 2, 1999.

(51) Int. Cl.[7] .................................................. A61B 5/05
(52) U.S. Cl. ........................ 600/407; 600/410; 424/9.2
(58) Field of Search ................................. 600/408, 409, 600/436, 407, 410, 411, 425, 473, 475, 547, 544; 435/4; 324/307, 309; 382/128; 607/45, 46, 58; 424/9.3, 9.2

(56) References Cited

U.S. PATENT DOCUMENTS 3,998,209 A 12/1976 Macvaugh
4,960,815 A 10/1990 Moos
5,011,846 A 4/1991 Gittos et al.

(Continued)

FOREIGN PATENT DOCUMENTS

WO    WO 97 33515 A    9/1997

OTHER PUBLICATIONS

Breiter, Hans C. et al., "Acute Effects of Cocaine on Human Brain Activity and Emotion", Neuron, vol. 19, Sep. 1997, pp. 591–611.

Gelnar, Patricia A. et al., "A Comparative fMRI Study of Cortical Representations for Thermal, Painful, Vibrotactile, and Motor Performance Tasks", Neuroimage, vol. 10, 1999, pp. 460–482.

(Continued)

Primary Examiner—Shawna J. Shaw
(74) Attorney, Agent, or Firm—Clark & Elbing LLP

(57) ABSTRACT

A method for measuring indices of brain activity includes non-invasively obtaining signals of central nervous system (CNS) activity, localizing signals to specific anatomical and functional CNS regions, correlating the signals from pain and reward brain regions, and interpreting the correlation results. The results of interpreting the correlation results can be used for objectively measuring, in individual humans or animals, their responses to motivationally salient stimuli including but not limited to stimuli which are internal or external, conscious or non-conscious, pharmacological or non-pharmacological therapies, and diseased based processes. This method for measuring brain activity in reward/aversive central nervous system regions, can further be used to determine the efficacy of compounds.

31 Claims, 40 Drawing Sheets

U.S. PATENT DOCUMENTS

| | | | |
|---|---|---|---|
| 5,189,064 A | | 2/1993 | Blum et al. |
| 5,234,680 A | | 8/1993 | Rogers, Jr. et al. |
| 5,320,825 A | | 6/1994 | Kung |
| 5,324,504 A | | 6/1994 | Roger, Jr. et al. |
| 5,397,563 A | | 3/1995 | Rogers, Jr. et al. |
| 5,552,406 A | | 9/1996 | Mendelson et al. |
| 5,559,125 A | | 9/1996 | Kulagowski et al. |
| 5,574,140 A | | 11/1996 | Pollack et al. |
| 5,603,322 A | | 2/1997 | Jesmanowicz et al. |
| 5,632,276 A | | 5/1997 | Eidelberg et al. |
| 5,656,267 A | | 8/1997 | Sagen et al. |
| 5,659,041 A | | 8/1997 | Pollack et al. |
| 5,662,112 A | | 9/1997 | Heid |
| 5,858,327 A | | 1/1999 | Pollack et al. |
| 5,910,728 A | * | 6/1999 | Sodickson ................. 324/309 |
| 5,925,634 A | | 7/1999 | Olney |
| 5,958,596 A | | 9/1999 | Claussen et al. |
| 6,015,786 A | | 1/2000 | Mascarenhas et al. |
| 6,018,675 A | | 1/2000 | Apkarian et al. |
| 6,025,332 A | | 2/2000 | Mascarenhas et al. |
| 6,025,368 A | | 2/2000 | Mascarenhas et al. |
| 6,073,041 A | * | 6/2000 | Hu et al. ..................... 600/410 |
| 6,099,319 A | | 8/2000 | Zaltman et al. |
| 6,196,226 B1 | | 3/2001 | Hochman et al. |
| 6,240,308 B1 | | 5/2001 | Hardy et al. |
| 6,289,234 B1 | | 9/2001 | Mueller |
| 6,298,258 B1 | | 10/2001 | Heid et al. |
| 6,321,105 B1 | | 11/2001 | Jenkins et al. |
| 6,356,781 B1 | | 3/2002 | Lee et al. |
| 6,517,812 B1 | | 2/2003 | Breiter et al. |
| 2002/0058867 A1 | * | 5/2002 | Breiter et al. ................ 600/407 |
| 2003/0211459 A1 | * | 11/2003 | Breiter et al. ................... 435/4 |
| 2004/0052730 A1 | * | 3/2004 | Hochman .................... 424/9.2 |
| 2004/0082862 A1 | * | 4/2004 | Chance ........................ 600/473 |
| 2004/0092809 A1 | * | 5/2004 | DeCharms .................. 600/410 |

OTHER PUBLICATIONS

Kai–Hsiang, Chuang et al., "Model–Free Functional MRI Analysis Using Kohonen Clustering Neural Network and Fuzzy C–means", IEEE Transactions on Medical Imaging, IEEE, vol. 18, No. 12, Dec. 1999, pp. 1117–1128.

PCT International Search Report dated Oct. 10, 2001 corresponding to International Application No. PCT/US01/10377.

Adolphs, R., Tranel, D., Damasio, H., and Damasio, A. (1994). Impaired recognition of emotion in facial expressions following bilateral damage to the human amygdala. Nature 372, 669–672.

Adolphs, R., Tranel, D., Damasio, H., and Damasio, A. (1995). Fear and the human amygdala. J. Neurosci. Sep. 15, 5879–5891.

Aggleton, J.P., Burton, M.J., and Passingham, R.E. (1980). Cortical and subcortical afferents to the amygdala in the rhesus monkey (*Macaca mulatta*). Brain Res. 190, 347–368.

Adler, L.J., Gyulai, F.E., Diehl, D.I., Mintun, M.A., Winter, P.M., and Firestone, L.L (1997). Regional brain changes associated with fentanyl analgesia elucidated by positron emission tomography. Anesth, Analg. 84, 120–126.

Aguirre GK, Zarahm E, D'Esposito M. A critique of the use of the Kolmogorov–Smirnov (KS) statistic for the analysis of BOLD fMRI data. Magn Reson Med. Mar. 1998;39(3):500–5.

Albanese A, Minciacchi D. Organization of the ascending projections from the ventral tegmental area: a multiple fluorescent retrogate tracer study in the rat. J Comp Neurol. Jun. 1, 1983; 2 1 6(4):406–20.

Altier N, Stewart J. Dopamine receptor antagonists in the nucleus accumbens attenuate analgesia induced by ventral tegmental area substance P or morphine and by nucleus accumbens amphetamine. J Pharmacol Exp Ther. Apr. 1998;285(1):208–15.

Amaral, D.G., and Price, J.L. (1984). Amydgalo–cortical projections in the monkey (*Macaca fascicularis*). J. Comp. Neurol. 230, 465–496.

Amorapanth P, LeDoux JE, Nader K. Different lateral amygdala outputs mediate reactions and actions elicited bya fear–arousing stimulus. Nat Neurosci. Jan. 2000;3(1):74–9.

Apkarian A V, Darbar A, Krauss BR, Gelnar PA, Szeverenyi NM. Related Articles Differentiating cortical areas related to pain perception from stimulus identification: temporal analysis of fMRI activity. J Neurophysiol. Jun. 1999;81(6):2956–63.

Arvanitogiannis, A., Waraczynski, M., and Shizgal, P. (1996). Effects of excitotoxic lesions of the basal forebrain on MFB self–stimulation. Physiology and Behavior 59(4/5), 795–806.

Bain, G. T., and Kornetsky, C. (1987). Naloxone attenuation of the effect of cocaine on rewarding brain stimulation. Life Sciences 40, 1119–1125.

Ballantine HT Jr, Cassidy WL, Flanagan NB, Marino R Jr. Stereotaxic anterior cingulotomy for neuropsychiatric illness and intractable pain. J Neurosurg. May 1967;26(5):488–95.

Bandettini, P.A., Wong, E.C., Hinks, R.S., and Hyde, J.S. (1992). Time course EPI of human brain function during task activation. Mag. Res. Med. 25, 390–397.

Barasi S. Responses substantia nigra neurones to noxious stimulation. Brain Res. Jul. 27, 1979;171(1):121–30.

Barch, D.M., Braver, T.S., Nystrom, L.E., Forman, S.D., Noll, D.C., and Cohen, J.D. (1997). Dissociating working memory from task difficulty in human prefrontal cortex. Neuropsychologia 35, 1373–1380.

Basbaum AI, Fields HL.Endogenous pain control mechanisms: review and hypothesis. Ann Neurol. Nov. 1978;4(5):451–62.

Baune A, Sommer FT, Erb M, Wildgruber, Kardatzki B, Palm a, Grodd W. Dynamical cluster analysis of cortical fMRI activation. Neuroimage. May 1999;9(5):477–89.

Baxter, L.R., Schwartz, J.M., Phelps, M.E., Mazziotta, J.C., Guze, B.H., Selin, C.E., Gerner, R.H., and Sumida, R.M. (1989). Reduction of prefrontal cortex glucose metabolism common to three types of depression. Arch Gen Psychiatry 46, 243–250.

Becerra L, Breiter H, Jenkins L, aonzalez a, Borsook D. Early Activation of Reward/Aversive Circuitry following Noxious Thermal Stimuli: Dissociation of Motivation–Emotion Circuitry from Sensory–Discriminative Circuitry (in preparation).

Becerra, L.R., Breiter, H.C., Stojanovic, M., Fishman, S., Edwards, A., Cornite, A.R., Oonzalez, R.G., and Borsook, D. (1999). Human brain activation under controlled thermal stimulation and habituation to noxious heat: an fMRI study. Magnetic Res. in Medicine 41, 1044–1057.

Bechara, A., Damasio, H., Tranel, D., and Damasio, A.R. (1998). Dissociation of working memory from decision making within the human prefrontal cortex. J. Neurosci. 18, 428–437.

Behbehani MM. Behaviors. Prog. Neurobiol. 3.247–279.
Behbehani MM. Functional characteristics of the midbrain periaqueductal gray. Prog Neurobiol. Aug. 1995;46(6):575–605.

Belliveau, J.W., Kennedy, D.N., McKinsey, R.C., Buchbinder, B.R., Weiskoff, R.M., Cohen, M.S., Vevea, J.M., Brady, T.J., Rosen, B.R. (1991). Functional mapping of the human visual cortex by magnetic resonance imaging. Science 254, 716–719.

Bench, C.J., Friston, K.J., Brown, R.G., Frackowiak, R.S.J., and Dotan, R.J. (1993). Regional cerebral blood flow in depression measured by positron emission tomography: The relationship with clinical dimensions. Psych. Med. 23, 579–590.

Bench, C.J., Friston, K.J., Brown, R.G., Scott, L.C., Frackowiak, R.S.J., & Dolan, R.J. (1992). The anatomy of melancholia –focal abnormalities of cerebral blood flow in major depression. Psych. Med. 22, 607–615.

Bennett, A.J., and Mayer, D.J. (1979). Inhibition of spinal cord interneurons by narcotic microinjection and focal electrical stimulation in the periaqueductal central gray matter. Brain Res. 172(2), 243–257.

Berkowitz, B.A.. Cerreta. K. V., and Spector. S. (1974). The influence of physiologic and phannacologic factors on the disposition of morphine as determined by radioimmunoassay. J Phannacol Exp Ther. 191(3), 527–534.

Berns, G.S., Cohen, J.D., & Mintun, M.A. (1997). Brain regions responsive to novelty in the absence of awareness. Science 276, 1272–1275.

Bester, H. et al., The Spino(trigemino) Pontoamygdaloid Pathway: Electrophysiological Evidence for An Involvement in Pain Processes. J. Neurophysiol. Feb. 1995; 73(2): 568–585.

Blackburn, J., Pfaus, J., & Phillips, A. (1992). Dopamine functions in appetitive and defensive behaviors. Prog. Neurobiol. 3, 247–279.

Blair et al., Dissociable neural responses to facial expressions of sadness and anger Brain (1999) 122, 883–893.

Bernard JF, Huang oF, Besson JM. Nucleus centralis of the amygdala and the globus pallidus ventralis: electrophysiological evidence for an involvement in pain processes. J Neurophysiol. Aug. 1992;68(2):551–69.

Blackburn, J., Phillips, A., Jakubovic, A., and Fibiger, H. (1986). Increased dopamine metabolism in the nucleus accumbens and striatum following consumption of a nutritive meal but not a palatable non–nutritive saccharine solution. Pharmacology Biochemistry and Behavior 25, 1095–1100.

Blackburn, J., Phillips, A., Jakubovic, A., and Fibiger, H. (1989). Dopamine and preparatory behavior: II. a neurochemical analysis. Behavioral Neuroscience 103(1), 15–23.

Borod, 1.C., Koff, E., Perlman–Lorch, M., and Nicholas, M. (1986). The expression and perception of facial emotion in brain–damaged patients. Neuropsychologia 24(2), 169–180.

Borod, J.C., Koff, E., Perlman–Lorch, M., and Nicholas, M. (1985). Channels of emotional expression in patients with unilateral brain damage. Arch. Neurology 42, 345–348.

Botvinick M, Nystrom LE, Fissell K, Carter CS, Cohen JD. Conflict monitoring versus selection– for–action in anterior cingulate cortex. Nature. Nov. 11, 1999;402(6758): 179–81.

Boxerman, J.L., Bandettini, P.A., Kwong, K.K., Baker, J.R., Davis, T.L., Rosen, B.R., and Weisskoff, R.M. (1995). The intravascular contribution to fMRI signal change: Monte Carlo modeling and diffusion–weighted studies in vivo. Magn. Reson. Med 34, 4–10.

Boynton et al., Linear sysems analysis of functional magnetic resonance imaging in human V1, The journal of neuroscience, Jul. 1, 1996, 16(13): 4207–4221.

Bozarth MA, Wise RA. Involvement of the ventral tegmental dopamine system in opioid and psychomotor stimulant reinforcement. NIDA Res Monogr. 1986:67:190–6.

Braver, T.S., Cohen, J.D., Nystrom, L.E., Jonides, J., Smith, E.E., and Noll, D.C. (1997). A parametric study of prefrontal cortex involvement in human working memory. Neuroimage 5(1), 49–62.

Breiter HC, BecelTa L, Gonzalez RO, Huffman, EK, Harter K, Ienkins L, Cornite A, Borsook D. Morphine activates reward circuitry in the human brain. (submitted to Neuron). (unpublished).

Breiter HC, EtcoffNL, Whalen PJ, Kennedy W A, Rauch SL, Buckner RL, Strauss MM, Hyman SE, Rosen BR. Response and habituation of the human amygdala during visual processing of facial expression. Neuron. Nov. 1996;17(5):875–87.

Breiter, H.C., and Rosen, B.R. (1989). Functional magnetic resonance imaging of brain reward circuitry in the human. N.Y. Acad. Sci. 877, 523–547.

Breiter, H.C., Rauch, S.L., Kwong, K.K., Baker, I.R., Weisskoff, R.M., Kennedy, D.N., Kendrick, A.D., Davis, T.L., Iang, A., Cohen, M.S., Stern, C.E., Belliveau, I. W., Baer, L., O'Sullivan, R.L., Savage, C.R., Ienike, M.A., and Rosen, B.R. (1996a). Functional magnetic resonance imaging of symptom provocation in obsessive–compulsive disorder. Arch. Oen. Psychiatry 53, 595–606.

Brock, J.W., Ng, J.P., and Justice, J.B. Jr. (1990). Effect of chronic cocaine dopamine synthesis in the nucleus accumbens as determined by microdialysis perfusion with NSD1015. Neurosci. Lett. 117, 234–239.

Buckner, R.L., Petersen SoB., Ojemann, J.C., Miezin, F.M, Squire, LR., and Raichle, M.E., (1995). Functional anatomical studies of explicit and implicit memory retrieval (aSks. I. Neurosci. 15, 12–29.

Bushnell MC, Duncan GH, Hofuauer RK, Ha B, Chen JI, CalTier B. Pain perception: is there a role for primary somatosensory cortex? Proc Natl Acad Sci U S A. Jul. 6, 1999;96(14):7705–9.

Cabanac, M. (1971). Physiological role of pleasure. Science 173(2), 1103–1107.

Cabib S, Puglisi–Allegra S. Opposite responses ofmesolimbic dopamine system to controllable and uncontrollable aversive experiences. J Neurosci. May 1994;14(5 Pt 2):3333–40.

Cadoni, C., Solinas, M., Chiara, G. (2000). Psychostimulant sensitization: differential changes in accumbal shell and core dopamine. Eur. J. Pharmacol. 388(1), 69–76.

Cador, M., Robbins, T.W., and Everitt, B.J. (1989). Involvement of the amygdala in stimulus–reward associations: interaction with the ventral striatum. J. Neurosci. 30, 77–86.

Cahill, L., Haier, R.J., Fallon, J., Alkire, M.T., Tang, C., Keator, D., Wu, I., and McGaugh, J.L. (1996). Amygdala activity at encoding conelated with long–tenn, free recall of emotional infonnation, Proceedings Nat. Acad. Sci. U.S.A. 93, 8016–8021.

CalTive P. The periaqueductal gray and defensive behavior: functional representation and neuronal organization. Behav Brain Res. Dec. 20, 1993;58(1–2):27–47.

Calder, A.J., Young, W.W., Rowland, D., PelTett, D.I., Hodges, J.R., and Etcoff, N.L. (1996). Facial emotion recognition after bilateral amygdala damage: differentially severe impainment of fear. Cognitive Neuropsychology 13, 699–745.

Carelli, R.M., Ijames, S.G., and Crumling, A.J. (Evidence that separate neural circuits in the nucleus accumbnes encode cocaine versus .natural (water and food) reward. J. Neurosci. 20(11): 4255–4266, Jun. 2000.

Carr DB, Sesack SR. Projections from the rat prefrontal cottex to the ventral tegmental area: target specificity in the synaptic associations with mesoaccumbens and mesocortical neurons. J Neurosci. May 15, 2000;20(10): 3864–73.

Carrive P. The periaqueductal gray and defensive behavior: functional representation and neuronalorganization. Behav Brain Res. Dec. 20, 1993;58(1–2):27–47.

Carstens, E., Steizer, B., and Zilrunermann, M. (1988). Microinjections of glutamate or morphine at coincident midbrain sites have different effects on nociceptive dorsal horn neurons in the rat. Neurosci Lett. 95(1–3), 185–191.

Casey KL, Minoshima S, Berger KL, Koeppe RA, Morrow TJ, Frey KA. Positron emission tomographic analysis of cerebral structures activated specifically by repetitive noxious heat stimuli. J. Neurophysiol. Feb. 1994;71(2):802–7.

Casey KL, Minoshima S, MolTOW TI, Koeppe RA. Comparison of human cerebral activation pattern during cutaneous warmth, heat pain, and deep cold pain. J Neurophysiol. Jul. 1996;76(1):571–81.

Casey KL. Forebrain mechanisms of nociception and pain: analysis through imaging. Proc Natl Acad Sci U S A. Jul. 6, 1999;96(14):7668–74.

Chance, W.T., Foli–Nelson, T., Nelson, J.L., and Fischer. J.E. (1987). Neurotransmitter alterations associated with feeding and safety. Brain Research 416, 228–234.

Chapman CR, Gavrin J. Suffering: the contributions of persistent pain. Lancet. Jun. 26, 1999;353(9171):2233–7.

Chiou, L.C., and Huang, L. Y. (1999). Mechanism underlying increased neuronal activity in the rat ventrolateral peraqueductal grey by a $\mu$–opioid. J. Physiol. (Land). 518 (Pt 2), 551–559.

Chudler EH. Response properties of neurons in the caudate–putamen and globus pallidus to noxious and non–noxious thermal stimulation in anesthetized rats. Brain Res. Nov. 23, 1998;8 1 2(1–2):283–8.

Chudler, E.H., Sugiyama, K., Dong, W.K., Nociceptive responses in the neostriatum and globus pallidus of the anesthetized rat, Journal of Neurophysiology, vol. 69, No. 6, Jun. 1993, 1890–1903.

Church, R.M. (1984). Properties of the internal clock. In Timing and Time Perception. Gibbon, J., Allan, L. (eds.), New York: New York Academy of Sciences, 566–582.

Clarke PB, Franklin KB. Infusions of 6–hydroxydopamine into the nucleus accumbens abolish the analgesic effect of amphetamine but not of morphine in the formalin test. Brain Res. May 15, 1992;580(1–2): 106–10.

Cody, F.W. and Richardson, H.C> (1977) Trigeminal projections to the cerebellar cortes in the cat. Proc. IEEE Physiologicl Soc. 1977 41P.

Coghill, R.C., Talbot. J.D.. Evans, A.C., Meyer, E., Gjedde, A., Bushnell, M.C., and Duncan, G.H. (1994). Distributed processing of pain and vibration by the human brain. J. Neurosci. 14.4095–4108.

Coghill. R.C.. Sang. C.N.. Maisog, J.M., and Iadarola, MJ. (1999). Pain intensity processing within the human brain: a bilateral. distributed mechanism. I. Neurophysiol. 82(4). 1934–1943.

Cohen SR, Melzack R. The habenula and pain: repeated electrical stimulation produces prolonged analgesia but lesions have no effect on fonnalin pain or morphine analgesia. Behav Brain Res. Apr. 30, 1993;54(2): 171–8.

Cohen, M.S., Kosslyn, S.M., Breiter, H.C., DiGirolamo, GJ., Thompson, W .L., Anderson, A.K., Bookheimer, S. Y ., Rosen, B.R., Belliveau, J. W .(1996). Changes in cortical activity during mental rotation: A mapping study using functional MRI. Brain 119, 89–100.

Commons, K.G., van Bockstaele, E.I., and Pfaff, D. W. (1999). Frequent colocalization of mu opioid and NMDA–type glutamate receptors at postsynaptic sites in periaqueductal gray neurons. J. Comp. Neurol. 408(4),549–559.

Corrigal, W.A.. and Vaccarino, F.J. (1988). Anatagonist treatment in the nucleus accumbens or periaqueductal grey affects heroin self–administration. Pharm. Bioch. and Behvioral. 30, 443–450.

Craig AD, Chen K, Bandy D, Reiman EM. Thermosensory activation of insular cortex. Nat Neurosci. Feb. 2000;3(2): 184–90.

Craig, A.D., Bushnetl, M.C., Zhang, E.T., and Blomqvist, A. (1994). A thalamic nucleus specific for pain and temperature sensation. Nature 372, 770–773.

Craig, A.D., Reiman, E.M., Evans, A., and Bushnell, M.C. (1996). Functional imaging of an illusion of pain. Nature 384, 258–260.

Critchley HD, Elliott R, Mathias CJ, Dolan RJ. Neural activity relating to generation and representation of galvanic skin conductance responses: A functional magnetic resonance imaging study. J Neurosci. Apr. 15, 2000;20(8):3033–40.

D'Esposito, M., Detre, J.A., Alsop, D.C., Shin, R.K., Atlas, S., and Grossman, M. (1995). The neural basis of the central executive system of working memory. Nature 378(6554), 279–281.

Daghero, A.M., Bradley, E.L. Jr, and Kjssin, I. (1987). Midazolam antagonizes the analgesic effect of morphine in rats. Anesth. Analg. 66(10), 944–947.

Dale, A.M. (1999). Optimal experimental design for event–related fMRI. Human Brain Mapp. 8(2–3), 109–114.

Dalton JA, Feuerstein M, Carlson, J, Roglunan K. Biobehavioral pain profile: development and psychometric properties.Pain. Apr. 1994; 57(1):95–107.

Damasio, A.R., Individuals with sociopathic behavior caued by frontal damage fail to respond autonomically to social stimuli, Behavioural Brain Research, 41 (1990), 81–94.

David, A., Blamire, A., & Breiter, H.C. (1994). Functional magnetic resonance imaging. Brit. J. Psychiatry 164, 2–7.

Davidson, R.J., & Sutton, S.K. (1995). Affective neuroscience: The emergence of a discipline. Current Opin. Neurobiology 5, 217–224.

Davidson, R.J. (1998). Affective style and affective disorders: Perspectives from affective neuroscience. Cognition and Emotion 12, 307–330.

Davidson, R.J., and Fox, N.A. (1982). Asymmetrical brain activity discriminates between positive and negative affective stimuli in human infants. Science 218, 1235–1236.

Davidson, R.J., and Fox, N.A. (1988). Frontal brain asymmetrical predicts infants' response to maternal separation. Journal of Abnormal Psychology, vol. 98, No. 2, 127–131.

Davidson, R.J., Ekman, P., Saron, C.D., Senulis, J.A., and Friesen, W.V. (1990). Approach–withdrawal and cerebral asymmetry: Emotional expression and brain physiology I. J. Personality and Social Psych. 58(2), 330–341.

Davis KD, Kiss ZH, Tasker RR, Dostrovsky JO. Thalamic stimulation–evoked sensations in chronic pain patients and in nonpain (movement disorder) patients. J Neurophysiol. Mar. 1996;75(3): 1026–37.

Davis KD, Kwan CL, Crawley AP, Milkulis DJ. Event–related fMRI of pain: entering a new era in imaging pain. Neuroreport. Sep. 14, 1998;9(13):3019–23.

Davis KD, Kwan CL, Crawley AP, Mikulis DI. Functional MRI study of thalamic and cortical activations evoked by cutaneous heat, cold and tactile stimuli. J Neurophysiol. Sep. 1998;80 (3): 1533–46.

Davis, K.D., Kiss, Z.H., Luo, L., Tasker R.R., Lozanno, A.M., and Dostrovsky, J.O. (1998b). Phantom sensations generated by thalamic microstimulation. Nature. 391(6665), 385–387.

Decavel, C., and Van den Pol, A.N. (1990). GABA: a dominant neurotransmitter in the hypothalamus. J. Comp. Neurol. 302, 1019–1037.

Derbyshire SW, Jones AK, Cerebral responses to a continual tonic pain stimulus measured using positron emission tomoraphy. Pain 76. 1998 pp. 127–135..

Derbyshire SW, Jones AK, Oyulai F, Clark S, Townsend D, Firestone LL. Pain processing during three levels of noxious stimulation produces differential patterns of central activity. Pain. Dec. 1997;73(3):431–45.

Devinsky O, Morrell MJ, Vogt BA. Contributions of anterior cingulate cortex to behaviour. Brain. Feb. 1995,118 (Pt 1):279–306.

DiChiara, G. and Imperato, A. (1988). Drugs abused by humans preferentially increase synaptic dopamine concentrations in the mesolimbic system of freely moving rats. Proceedings of the National Academy of Sciences 85, 5274–5278.

Dill. R.E., and Costa. E. (1977). Behavioural dissociation of the enkephalinergic systems of nucleus accumbens and nucleus caudatus. Neuraphannacology 16(5).323–326.

Drevets, W.C., Videen, T.O., Price, J.L., Preskom, S.H., Carmichael, T., & Raichle, M.E. (1992). A functional anatomical study of unipolar depression. J. Neurosci. 12, 3628–3641.

Edmjnster, W.B., Talvage, T.M., Ledden, P.I., and Weisskoff, R.M. (1999). Improved auditory cortex imaging using clustered volume acquisitions. Hum. Brain Map 7(2), 89– 97.

Ekman, P ., Sorenson, E.R., and Friesen, W.V. (1969). Pan–cultural elements in facial displays of emotion. Science 164, 86–88.

Etcoff, N.L. (1984). Selective attention to facial identity and facial emotion. Neuropsychologia 22(3), 281–295.

Everitt, B.J. (1997). Craving cocaine cues: cognitive neuroscience meets drug addiction research. Trends in Cognitive Sciences 1(1), 1–2.

Everitt, B.J., Moms, K.A., O'Brien, A., and Robbins, T.W. (1991). The basolateral amygdala–ventral striatal system and conditioned place preference: further evidence of limbic–striatal interactions underlying reward–related processes. J. Neurosci. 42, 1–18.

Fields HL, Heinricher MM, Mason P. Neurotransmitters in nociceptive modulatory circuits. Ar∥$1\mu$ Rev Neurosci. 1991;14:219–45.

Fields HL, Malick A, Burstein R. Dorsal horn projection targets of ON and OFF cells in the rostral ventromedial medulla. JNeurophysiol. Oct. 1995;74(4):1742–59.

Fiez. J.A., Raife, E.A., Balota, D.A., Schwarz, J.P., Raichle, M.E., and Petersen, SoB. (1996). A positron emission tomography study of the short –tenn maintenance of verbal information. J. Neurosci. 16(2),808–822.

Fischl, B., Sereno, M.I., Tootell, R.B., and Dale, A.M. (1999). High–resolution intersubject averaging and a coordinate system for the cortical surface. Hum Brain Mapp. 8(4), 272–284.

Franklin, KB. Analgesia and .Abuse Potential: an accidental association or a common substrate? Pharmacol Biochem Behav. Apr. 1998; 59 (4):993–1002.

Franklin, KB. Analgesia and the neural substrate of reward. Neurosci. Biobehav Rev. 1989 Sununer–Fall; 13(2–3): 149–54.

Friston KJ, Holmes AP, Poline JB, Grasby PJ, Williams SC. Frackowiak RS, Turner R. Analysis of fMRI time–series revisited. Neuroimage. Mar. 1995;2(1):45–53.

Friston, K.J., Holmes, A.P., Worskey, K.I. (1999). How many subjects constitute a study? Neuroimage 10, 1–5.

Gaffan, D., and Harrison, S. (Aug. 1987). Amygdalectomy and disconnection in visual learning for auditory secondary reinforcement by monkeys. J. Neurosci. 7, 2285–2292.

Gaffan, E.A., Gaffan, D.. and Harrison, S. (1988). Disconnection of the amygdala from visual association cortex impairs visual reward–association learning in monkeys. J. Neurosci. 8, 3144–3150.

Gallagher, M., & Chiba, A.A. (1996). The amygdala and emotion. Current Opin. Neurobiology 6, 221–227.

Gallagher, M., & Holland, PC (Dec. 1994). The amygdala complex: multiple roles in associative learning an attention. Proc. Natl. Acad. Sci. vol. 91, pp 11771–11776.

Gao DM, Jeaugey L, Pollak P, Benabid AL. Intensity–dependent nociceptive responses from presumed dopaminergic neurons of the substantia nigra, pars compacta in the rat and their modification by lateral habenula inputs. Brain Res. Oct. 8, 1990;529(1–2):315–9.

Gear, R.W., Aley, K.O., and Levine, J.D. (1999). Pain–induced analgesia mediated by mesolimbic reward circuits. Neurosci. 19(16), 7175–7181.

Gebhart, G.F., Sandkuhler, J., Thalhammer, J.a., and Zimmermann M. (1984). Inhibition in spinal cord of nociceptive information by electrical stimulation and morphine microinjection at identical sites in midbrain of the cat. J Neurophysiol. 51(1), 75–89.

George, M.S., Ketter, T.A., Parekh, P.I., Horowitz, B., Herscovitch. P., and Post. R.M. (1995). Brain activity during transient sadness and happiness in healthy women. Amer. J. Psychiatry 152.341–351.

Gibbon, I., R.M. Church, S. Fairhurst, and Kacelnik, A. (1988). Scalar expectancy theory and choice between delayed rewards. Psychol. Rev. 95, 102–114.

Glickman SE, Schiff BB. A biological theory of reinforcement. Psychol Rev. Mar. 1967;74(2):81–109.

Golay X, Kollias S, Stoll G, Meier D, Valavanis A, Boesiger P. A new correlation–based fuzzy logic clustering algorithm for fMRI. Magn Reson Med. Aug. 1998;40(2):249–60.

Gollub, R.L., Breiter, H.C., Kantor, H., Kennedy, D., Gastfriend, D., Mathew, R.T., Makris, N., Guimaraes, A., Riorden, J., Campbell, T., Foley, M., Hyman, S.E., Rosen, B., and Weisskoff, R. (1998). Cocaine decreases cortical cerebral blood flow but does not obscure regional activation in functional magnetic resonance imaging in human subjects. J. Cereb. Blood Flow Metab. 18(7), 724–734.

Gracely RH, Kwitosz DM. The Descriptor Differential Scale: applying psychophysical principles to clinical pain assessment. Pain. Dec. 1988;35(3):279–88.

Guimaraes, A.R., Melcher, J.R., Talavage, T.M., Baker, J.R., Ledden, P., Rosen, B.R., Kiang, N.Y., Fullerton, B.C., and Weisskoff, R.M. (1998). Imaging subcortical auditory activity in humans. Hum Brain Mapp. 6(1):33–41.

Greden, J.F., Genero, N., Price, L., Feinberg, M., Levine, S., Facial Electromyography in Depression, Arch. Gen. Psychiatry, vol. 43, Mar. 1986, pp 269–274.

Gur, R.C., Erwin, R.J., Gur, R.E., Zwil, A.S., Heimberg, C., Kraemer, H.C., Facial emotion discrimination: II. Behavioral findings in depression, Psychiatry research, 42, 241–251, 1992.

Gutstein, H.B., Mansour, A., Watson, Akil, H., and Fields, H.L. (Jun. 1998). Mu and kappa opioid receptors in periaqueductal gray and rostral ventromedial medulla. Neuroreport. 9(8). 1777–1781.

Gysling, K., Wang, R.Y. (1983). Morphine–induced activation of A 10 dopamine neurons in the rat. Brain Res. 277(1), 119–27.

Haber SN, Fudge JL. The primate substantia nigra and VT A: Integrative circuitry and function. Crit Rev Neurobiol. 1997;11(4):323–42.

Hakan, R.L., and Henriksen, (Oct. 1989). Opiate influences on nucleus accumbens neuronal electrophysiology: dopamine and non–dopamine mechanisms. Journal of Neurosci. 9 (10),3538–3546.

Hakan, R.L., and Henriksen, S.I. (1987). Systematic opiate adminstration has heterogeneous effects on activity recorded from nucleus neurons in vivo. Neuroscience Lett. 83, 307–312.

Hamann, S.B., Stefanacci, L., Squire, L.R., Adolphs, R., Tranel, D., Damasio, H., & Damasio. A. (1996). Recognizing facial emotion. Nature 379, 497.

Hatfield, T., Ran, I.–S., Conley, M., Gallagher, M., & Holland, P. (Aug. 15, 1996). Neurotoxic lesions of basolateral, but not central, amygdala interfere with pavlovian second–order conditioning and reinforcer devaluation effects. J. Neurosci. 16 (16),5256–5265.

Haxby, J.V., Horwitz, B., Ungerielder, L.G., Maisog, J.M., Pietrini, P., and Grady, C.L. (Nov. 1994). The functional organization of human extratriate cortex: a PET–rCBF study of selective attention to faces and locations. J. Neurosci. 14(11), 6336–6353.

Heffner, T., Hartman, J., and Seidan, L. (1980). Feeding increases dopamine metabolism in the rat brain. Science 208, 1168–1170.

Heilman, K.M., Bowers, D., Speedie, L., & Coslett, H.B. (Apr. 1983). The comprehension of emotional and nonemotional prosody. Neurobiology 33(2), 241.

Helmar, L., Harlan, R.E., Alheid, G.F., Garcia, M.M., and DeOlmos J. (1997). Substantia innominata: a notion which impedes clinical–anatomical correlations in neuropsychiatric disorders. Neuroscience 76(4),957–1006.

Heimer, L., Alheid, G.F., de Olmos, J.S., Groenewegen, H.J., Haber, S.N., Harlan, R.E., Zahm, D.S. (Summer 1997). The accumbens: beyond the core–shell dichotomy. J. Neuropsychiatry Clin. Neurosci. 9(3), 354–81.

Heinricher MM, Cheng ZF, Fields HL. Evidence for two classes of nociceptive modulating neurons in the peraqueductal gray. J Neurosci. Jan. 1967;7(1):271–8.

Henriques, J.B., & Davidson, R.J. (1991). Left frontal hypoactivation in depression. J. Abnorm. Psych. 100(4), 535–545.

Henriques, J.B., & Davidson, R.J. (1990). Regional brain electrical asymmetries discriminate between previously depressed and healthy control subjects. J. Abnorm. Psych. 99(1), 22–31.

Hernandez, L., and Hoebel, B. (1988). Food reward and cocaine increase extracellular dopamine in the nucleus accumbens as measured by microdialysis. Life Sci. 42, 1705–1712.

Hollerman, J.R., and Schultz, W. (Aug. 1998). Dopamine neurons report an error in the temporal prediction of reward during learning. Nat Neurosci. 1(4), 304–309.

Honey CR, Stoessl AJ, Tsui JK, Schulzer M, Caine DB. Unilateral pallidotomy for reduction of parkinsonian pain. J Neurosurg. Aug. 1999; 91 (2): 198–201.

Hutchison WD, Davis KD, Lozano AM, Tasker RR, Dostrovsky JO. Pain–related neurons in the human cingulate cortex. Nat Neurosci. May 1999;2(5):403–5.

Iadarola MI, Berman KF, Zeffiro TA, Byas–Smith MG, Oracely RR, Max MB, Bennett OJ. Neural activation during acute capsaicin–evoked pain and allodynia assessed with PET. Brain. May 1998;121 (Pt 5):931–47.

Ingvar M. Pain and functional imaging. Philos Trans R Soc Lond B Biol Sci. Jul. 29, 1999, 354: 1347–58.

Irwin, W., Davidson, R.J., Lowe, M, Mock, B.J., Sorenson, J.A., & Turski, P.A. (Jul. 1996). Human amygdala activation detected with echo–planar functional magnetic resonance imaging. NeuroReport 7(11), 1765–1769.

Iversen, s. D., and Mishkin, M. (1970). Preservative interference in monkeys following selective lesions of the inferior prefrontal convexity. Exp. Brain Res. 11, 376–386.

Jaeger, J., Borod, J.C., & Peselow, E. (1986) Facial expression of positive and negative emotions in patients with unipolar depression. J. Affective Dis. 11,43–50.

Jensen TS. Opioids in the brain: supraspinal mechanisms in pain control. Acta Anaesthesiol Scand. Jan. 1997;41(1 Pt 2): 123–32.

Johnson, S. W., and North, R.A. (Feb. 1992). Opioids excite dopamine neurons by hyperalarization of local interneurans. J. Neurosci. 12(2),483–488.

Jones AK, Brown WD, Friston KJ, Qi L y , Frackowiak RS. Cortical and subcortical localization of response to pain in man using positron emission tomography. Proc R Soc Lond B Bioi Sci. Apr. 22, 1991;244(1309):39–44.

Jones, A.K., Qi, L. Y ., Fujiwara, T., Luthra, S.K., Ashburner, I., Bloomfield, P., Cunningham, V J.. Itoh, M., Fukuda, H.,and Jones, T. (1991 a or b). In vivo distribution of opioid receptors in man in relation to the cortical projections of the medial and lateral pain systems measured with positron emission tomography. Neurosci. Lett. 126(I), 25–28.

Jones, B., and Mishkin, M. (1972). Limbic lesion and the problem of stimulus–reinforcement association. Expi. Neurol. 36, 362–377.

Jonides, J ., Smith, E.E., Koeppe, R.A., A wh, E., Minoshima, S., & Mintun, M.A. (Jun. 17, 1993). Spatial working memory in humans as revealed by PET. Nature 363, 623–625.

Kalivas PW, Nakamura M. Neural systems for behavioral activation and reward. Current Opin Neurobiol. Apr. 1999, 9(2): 223–7.

Kalyuzhny, AE, Arvidsson, U, Wu W, Wessendorf MW. (Oct. 15, 1996). $\mu$–Opioid and $\delta$–opioid receptors are expressed in brainstem antinociceptive circuits: studies using immunocytochemistry and retrogate tract–tracing. J Neurosci. 16(20), 6490–503.

Kang W, Wilson SP, Wilson MA. Changes in nociceptive and anxiolytic responses following herpes virus–mediated preproenkephalin overexpression in rat amygdala are naloxone–reversible and transient. Ann NY Acad Sci. Jun. 29, 1999;877:751–5.

Kanwisher, N., McDermott, 1., & Chun, M.M. (Jun. 1997). The fusiform face area: A module in human extrastriate cortex specialized for face perception. 1. Neurosci. 17 (11), 4302–4311.

Kapur, N., Friston, K.J., Young, A., Frith, C.D., & Frackowiak, R.S.J. (1995). Activation of human hippocampal formation during memory for faces: A PET study. Cortex 31, 99–108.

Kern MK, Birn RM, Jaradeh S, Jesmanowicz A, Cox R W, Hyde JS, Shaker R. Identification and characterization of cerebral cortical response to esophageal mucosal acid exposure and distention. Gastroenterology. Dec. 1998;115(6):1353–62.

Killcross, S., Robbins, T.W., and Everitt, B.J. (Jul. 24, 1997). Different types of fear–conditioned behaviour mediated by separate nuclei within amygdala. Nature 388, 377–380.

Kiyatkin, E., and Gratton, A. (1994). Electrochemical monitoring of extracellular dopamine in nucleus accumbens of rats lever–pressing for food Brain Res. 652, 225–234.

Konishi S, Nakajima K, Uchida I, Kameyama M, Nakahara K, Sekihara K, Miyashita Y. Transient activation of inferior prefrontal cortex during cognitive set shifting. Nat Neurosci. May 1998; 1(1):80–4.

Koob G.F, Sanna PP, Bloom FE. Neuroscience of addiction. Neuron. Sep. 1998, 21(3):467–76.

Koob, G.F., and Bloom F.E. (Nov. 1988). Cellular and molecular mechanisms of drug dependence. Science 242, 715–723.

Kosslyn, S:M., Pascual–Leone, A., Felician. O., Camposano, S., Keenan, J.P. Thompson, W .L., Ganis, G., Sukel, K.E.. and Alpert. NoM. (Apr. 1999). The role of area 17 in visual imagery: convergent evidence from PET and rTM5. Science 284(5411).167–170.

Kreek, M.J., and Koob, G.F. (1998). Drug dependence: stress and dysregulation of brain reward pathways. Drug and Alcohol Dependence 51, 23–47.

Krout KE, Jansen AS, Loewy AD. Periaqueductal gray matter projection to the parabrachial nucleus in rat. J Comp Neurol. Nov. 30, 1998;401(4):437–54.

Kwong, K.K., Belliveau, J. W ,. Chester. D.A., Goldberg, I.B.. Weiskoff, R.M., Poncelet, B.P., Kennedy. D.N., Hoppel. B.B., Cohen, M.S., Turner, R., Cheng, H.M.. Brody, T J. and Rosen, B.R. Dynamic magnetic resonance imaging of human brain activity during primary sensory stimulation. Proc. Natl. Acad. Sci. 89, (Jun. 1992) 5675–5679.

Lai SH, Fang M. A novel local PCA–based method for detecting activation signals in fMRI. Magn Reson Imaging. Jul. 1999;17(6):827–36.

Lane, R.D., Reiman. E.M Ahem, G.L. Schwartz, G.E., & Davidson, R.J. (Jul. 1997). Neuroanatomical correlates of happiness. sadness, and disgust. Amer. J. Psychiatry 154, 926–933.

LeDoux, J.E. (1993). Emotional memory: In search of systems and synapses. Ann. N. Y. Acad. Sci. 702, 149–157.

Lee RS, Koob GF, Henriksen SJ. Electrophysiological responses of nucleus accumbens neurons to novelty stimuli and exploratory behavior in the awake, unrestrained rat. Brain Res. Jul. 20, 1998;799(2):317–22.

Lenz, F.A., Gracely, R.H., Romanoski, A.1., Hope, E.J., Rowland, L.H., and Dougherty, P.M. (1995). Stimulation in the human somatosensory thalamus can reproduce both the affective and sensory dimensions of previously experienced pain. Nature Med. 1 (9), 910–913.

Leonard, C.M., Rolls, E.T., Wilson, F.A., & Baylis, G.C. (1985). Neurons in the amygdala of the monkey with responses selective for faces. Behav. Brain Res. 15, 159–176.

London, E.D., Cascella, N.G., Wong, D.F., Phillips, R.L., Danajs, R.F., Links, J.M., Herning, R., Grayson, R., Jaffe, J.H., and Wagner, H.N. (Jun. 1990). Cocaine–induced reduction of glucose utilization in human brain. Arch. Gen. Psychiatry 47, 567–574.

Lynd–Balta, B., and Haber, S.N. (1994). The organization of midbrain projections to the ventral striatum in the primate. Neuroscience 59, (3) 625–640.

Maldonado, R., Saiardi, A., Valverde, O., Samad, T.A., Roques B.P., Borrelli, E. (Aug. 1997) Absence of opiate rewarding effects in mice lacking dopamine D2 receptors. Nature 388 (6642), 586–589.

Manning BH, Mayer DJ. The central nucleus of the amygdala contributes to the production of morphine antinociception in the rat tail–flick test. J Neurosci. Dec. 1995;15(12):8199–213.

Manning BH. A lateralized deficit in morphine antinociception after unilateral inactivation of the central amygdala. J Neurosci. Nov. 15, 1998;18 (22):9453–70.

Mansour, A., Khachaturian, H., Lewis, M.E., Akil, H., and Watson, S.1. (Aug. 1987). Autoradiographic differentiation of mu, delta, and kappa opioid receptors in the forebrain and midbrain. J Neurosci. 7(8), 2445–2464.

Martin G., Nie Z, Siggins, G.R. (1997). $\mu$–opioid receptors modulate NMDA receptor– mediated responses in nucleus accumbens neurons. J Neurosci. 17, 11–22.

Martin WJ, Coffin PO, Attias E, Balinsky M, Tsou K, Walker IM. Anatomical basis for cannabinoid– induced antinociception as revealed by intracerebral microinjections. Brain Res. Mar. 20, 1999;822(1–2):237–42.

Martinol, J.L., Hardy, P., Feline A., Huret. J.D., Mazoyer, B., Attar–Levy, D., Pappata, S., & Syrota, A. (Oct. 1990). Left prefrontal glucose hypometabolism in the depressed state: A confirmation. Amer. J. Psychiatry 147, 13113–1317.

Mathews, R.T., and German, D.C. (1984). Electrophysiological evidence for excitation of rat ventral tegmental area dopamine neurons by morphine. Neuroscience 11 (3), 617–625.

Matthes, H. W., Maldonado, R., Simonin, F., Valverde, O. Slowe, S., Kitchen, I., Befort, K., Dierich, A., Le Meur, M., Dolle, P., Tzavara, E. Hanoune, J., Roques, B.P., and Kieffer BL. (1996). Loss of morphine–induced analgesia, reward effect and withdrawal symptoms in mice lacking the $\mu$–opioid–receptor gene. Nature.383(6603), 819–823.

Maximilian, V.A., Prohovnik, I., and Risberg, I. (1980). Cerebral hemodynamic response to mental activation in normo–and Hypercapnia. Stroke II (4), 342–347.

McCarthy, G., Blamire, A.M., Puce, A., Nobre, A., Bloch, G., Hyder, F., Goldman–Rakic, P., and Shulman, R.G. (1994). Functional magnetic resonance imaging of human prefrontal cortex activation during a spatial working memory task. Proc Natl Acad Sci USA 91, 8690–8694.

McCullough, L., Cousins, M., and Salamone, J. (1993). The role of nucleus accumbens dopamine in responding on a continuous reinforcement operant schedule: a neurochemicalJ and behavioral study. Pharmacol. Biochem. Behav. 46, 581–586.

McFarland, D.J., and Sibly, R.M. (1975). The behavioral final common path. Philos. Trans. R. Soc. Lond. B. Biol. Sci. 270(907), 265–293.

McLellan, A.T., Luborsky, L., and Woody, G.E. (1980). An improved diagnostic evaluation instrument for substance abuse patients: the addiction severity index. Journal of Nervous and Mental Disorders 168, 27–33.

Mellers, B.A., Schwartz, A., Ho, K., and Ritov, I. (1997). Decision affect theory: emotional reactions to the outcomes of risky options. Psychological Sciences 8(6), 423–429.

Mesulam, M.–M. (1990). Large–scale neurocognitive networks and distributed processing for attention,language, and memory. Annals of Neurology 28, 597–613.

Michel, M.E., et al., Binding of a New Opiate Antagonist, Nalmefene, to Rat Brain Membranes, Meth and Find Exptl Clin Pharmacol 1985; 7(4): 175–177.

Mirenowicz, J., and Schultz, W. (1994). Importance of unpredictability for reward responses in primate dopamine neurons. J. Neurophysiol. 72(2), 1024–1027.

Mirenowicz, J., and Schultz, W. (1996). Preferential activation of midbrain dopamine neurons by appetitive rather than aversive stimuli. Nature 379, 449–51.

Mitchell JM, Basbaum AI, Fields HL. A locus and mechanism of action for associative morphine tolerance. Nat Neurosci. Jan. 2000;3(1):47–53.

Morgan MJ, Franklin KB. 6–Hydroxydopamine lesions of the ventral tegmentum abolish D–amphetamine and morphine analgesia in the formalin test but not in the tail flick 'est. Brain Res. Jun. 11, 1990;519(1–2):144–9.

Morris, J.S., Frith, C.D., Perrett, D.I., Rowland, D., Yound, A.W., Calder, A.J., & Dolan, R.J. (1996). A differential neural response in the human amygdala to fearful and happy facial expression. Nature 383, 812–815.

Mouton LJ, VanderHorst VG, Holstege G. Large segmental differences in the spinal projections to the periaqueductal gray in the cat. Neurosci Lett. Nov. 28, 1997;238(1–2): 1–4.

Ngan SC, Hu X. Analysis of functional magnetic resonance imaging data using self–organizing mapping with spatial connectivity. Magn Reson Med. May 1999;41(5):939–46.

Nowycky, M.C., Waiters, J.R., and Roth, R.H. (1978). Dopaminergic neurans: effect of acute and chronic morphine administration on single cell activity and transmitter metabolism, J. Neural Trans. 42, 99–116.

O'Donnell P. Grace AA. Dopaminergic reduction of excitability in nucleus accumbens neurons recorded in vitro. Neuropsychopharmacology. Jul. 1996;15(1):87–97.

Ogawa, S., Lee, T., Nayak, A., and Glynn, P. (1990), Oxygenation–sensitive contrast in magnetic resonance image of rodent brain at high magnetic fields. Magn Reson Med. 14, 68–78.

Ogawa, S., Tank, D.W., Menon, R., Ellermann, J.M., Kim, S.G.., Merkle, H., and Ugurbil., K. (1992). Intrinsic signal changes accompanying sensory stimulation: functional brain mapping using MRI. Proc. Natl. Acad. Sci. USA 89, 5951–5955.

Oldfield, R.C. (1971). The assessment and analysis of handedness: the Edinburgh inventory. Neuropsychologia 9, 97–113.

Orzi, F., Passarelli, F., La Riccia, M., Di Grezia, R., Pontieri, F.E. (1996). Intravenous morphine increases glucose utilization in the shell of the rat nucleus accumbens. Eur. J. Pharmacol. 302(1–3), 49–51.

Pardo, J. V., Pardo, P.J., & Raichle, M.E. (1993). Neural correlates of self–induced dysphoria. Amer. J. Psychiatry 150,713–719.

Paulesu, E., Frith, C.D., and Frackowiak, R.S.J. (1993). The neural correlates of the verbal components of working memory. Nature 362, 342–345.

Pay S, Barasi S. A study of the connections of nociceptive substantia nigra neurones. Pain. Jan. 1982;12(1):75–89.

Peckys, D., and Landwehmeyer, a.B. (1999). Expression of mu, kappa, and delta opioid receptor messenger RNA in the human CNS: a P in situ hybridization study. Neuroscience 88(4), 1093–1135.

Peoples, L.L., and West, M.O. (1996). Phasic firing of single neurons in the rat nucleus accumbens correlated with the timing of intravenous cocaine self–administration. J. Neurosci. 16(10), 3459–3473.

Pettit, H.O., Ettenberg, A., Bloom, F.E., and Koob, G.F. (1984). Destruction of dopamine in the nucleus accumbens selectively attenuates cocaine but not heroin self–administration in rats. Psychopharmacology (Berlin) 84(2), 167–173.

Petrides, M., Alivisatos, B., Meyer, E., and Evans, A.C. (1993). Functional activation of the human frontal cortex during the performance of verbal working memory tasks. Proc. Natl. Acad. Sci. USA 90, 878–882.

Pfaffmann, C., Norgren, R., and Grill, H.J. (1977). Sensory affect and motivation. Ann. NY Acad. Sci. 290, 18–34.

Phillips, A., Atkinson, L., Blackburn, J., and Blaha, C. (1993). Increased extracellular dopamine in the nucleus accumbens of the rat ellicited by a conditional stimulus for food: an electrochemical study. Can. J. Physiol. Pharmacol. 71, 387–393.

Piepponen, T.P., Honkanen, A., Kivastik, T., Zharkovsky, A., Turtia, A., Mikkola, J.A., Ahtee, L. (1999). Involvement of opioid $\mu$1–receptors in opioid–induced acceleration of striatal and limbic dopaminergic transmission. Pharmacol. Biochem. Behav. 63(2), 245–52.

Porrino, L.J., Crane, A.M., and Goldman–Rakic, P.S. (1981). Direct and indirect pathways from the amygdala to the frontal lobe in rhesus monkeys. J. Comp. Neurol. 198, 121–136.

Price DD, Bush FM, Long S, Harkins SA. A comparison of pain measurement characteristics of mechanical visual analogue and simple numerical rating scales. Pain. Feb. 1994;56(2):217–26.

Puce, A., Allison, T., Asgari, M., Gore, J.C., & McCarthy, G. (1996). Differential sensitivity of human visual cortex to faces, letterstrings, and textures: A functional magnetic resonance imaging study. J. Neurosci. 16, 5205–5215.

Puce, A., Allison, T., Gore, J.C., & McCarthy, G. (1995). Face–sensitive regions in human extrastriate cortex studied by functional MRI; Journal of Neurophysiology, vol. 74 (3), 1192–1199.

Radhakishun, F., van Rec, I., and Westerink, B. (1988). Scheduled eating increases dopamine release in the nucleus accumbens of food–deprived rats as assessed with on–line brain dialysis. Neurosci. Lett 85, 351–356.

Rainville, P., Duncan, G.H., Price, D.D., Carrier, B., and Bushnell, M.C. (1997). Pain affect encoded in human anterior cingulate but not somatosensory cortex. Science 277 (5328), 968–971.

Rasia–Filho AA, Londero RG, Achaval M. Functional activities of the amygdala: an overview. J Psychiatry Neurosci. Jan. 2000;25(1): 14–23.

Reese, T .G., Davis, T .L., and Weisskoff, R.M. (1995). Automated shimming at 1.5T using echo planar image frequency maps. J. Magn. Reson. Imaging 5, 739–745.

Reiman, E.M., Lane, R.D., Ahern, G.L., Schwartz, G.E., Davidson, R.J., Friston, K.J., Yun, L.–S., & Chen, K. (1997). Neuroanatomicl correlates of externally and internally generated human emotion. Amer. J. Psychiatry 154, 918–925.

Richardson, N., and Gratton, A. (1996). Behavior–relevant changes in nucleus accumbens dopamine transmission elicited by food reinforcement: an electrochemical study in rat. J. Neurosci. 16, 8160–8169.

Robbins, T .W ., and Everitt, BJ. (1996). Neurobehavioral mechanisms of reward and motivation. Currnt Opinion in Neurobiology 6, 228–236.

Roberts, D.C., Koob, G.F., Klonoff, P., and Fibiger, H.C. (1980). Extinction and recovery of cocaine self–administration following 6–hydroxydopamine lesions of the nucleus accumbens. Pharmacol. Biochem. Behav. 12(5), 781–787.

Robinson, T .E., & K.C. BelTidge. 1993. The neural basis of drug craving: an incentive–sensitization theory of addiction. Brain Research Rev. 18, 247–291.

Rogers RD, Owen AM, Middleton HC, Williams EJ, Pickard JO, Sahakian BJ, Robbins TW. Choosing between small, likely rewards and large, unlikely rewards activates inferior and orbital prefrontal cortex. J Neurosci. Oct. 15, 1999; 19(20):9029–38.

Rompre, P.–P., and Shizgal, P. (1986). Electrophysiological characteristics of neurons in forebrain regions implicated in self–stimulation of the medial forebrain bundle in the rat. Brain Res. 364, 338–349.

Ross, E.D., & Mesulam, M.M. (1979). Dominant language functions of the right hemisphere?; Prosody and emotional gesturing. Arch.Neurology 36, 144–148.

Ryding, E., Eriksson, M.B.E., Rosen, I., and Ingvar, D.H. (1985). Regional cerebral blood flow (rCBF) in man during perception of radiant warmth and heat pain. Pain 22, 353–362.

Saade NE, Atweh SF, Bahuth NB, Jabbur SJ. Augmentation of nociceptive reflexes and chronic deafferentiation pain by chemical lesions of either dopaminergic terminals or midbrain dopaminergic neurons. Brain Res. Mar. 14, 1997;751(1):1–12.

Sackeim, H.A., Prohovnik, I., Moeller, J.R., Brown, R.P., Apter, S., Prudic, J., Devanand, D.P., & Mukherjee, S. (1990). Regional cerebral blood flow in mood disorders. Arch. Gen. Psychiatry 47, 60–70.

Salamone, I.D., Cousins, M.S., and Snyder, B.I. (1997). Behavioral functions of nucleus accumbens dopamine empirical and conceptual problems with the anhedonia hypothesis. Neurosci. Biobehav. Rev. 21:341–59.

Salamone, J., Cousins, M., McCullough, L., Carriero, D., and Berkowitz, R. (1994). Nucleus accumbens dopamine release increases during instrumental lever pressiing for food but not free food consumption. Pharmacol. Biochem. Behav. 49, 25–31.

Sandyk R, Barnford CR, Iacono RP. Pain and sensory symptoms in Parkinson's disease. Int. J Neurosci. Mar. 1988;39(1–2): 15–25.

Schlaepfer, T.E., Strain, E.C., Greenberg, B.D., Preston, K.L., Lancaster, E., Bigelow, G.E., Barta, P.E., and Pearlson, G.D. (1998). Site of opioid action in the human brain: mu and kappa agonists' subjective and cerebral blood flow effects. Am. J. Psychiatry 155(4), 470–473.

Schultz, W., Dayan, P., and Montague, P.R. (1997). A neural substrate of prediciton and reward. Science 275, 1593–1599.

Schultz et al. (1995). In Models of Information Processing in the Basal Ganglia, Houk, J.C., Davis, J.L., and Beiser, D.G. (eds). rvnT Press, Cambridge, MA, 233–248.

Schultz, W., Apicella, P., and Ljungberg, T. (1993). Resposc:s of monkey dopamine neurons to reward an conditioned stimuli during successive steps of learning a delayed response task. I. Neuroscience 13(3), 900–913.

Schultz, W ., and Romo. R. (1990). Dopamine neurons of the monkey midbrain: contigencies of responses to stimuli eliciting immediate behavioral reactions. J. Neurophysiol. 63, 607–624.

Schultz, W. (1986). Responses of midbrain dopamine neurons to behavioral trigger stimuli in the monkey. Journal of Neurophysiology 56, 1439–1461.

Schulz, W. (1997). Dopamine neurons and their role in reward mechanisms. Curr .Opin. Neurobiol. 7, 191–197.

Schultz, W., Apicella, P., Scamati, E., and Ljungberg, T. (1992). Neuronal activity in monkey ventral striatum related (to the expectation of reward. I. Neurosci. 12, 4595–4610.

Seidman, L.J., Breiter, H.C., Goodman, J.M., Goldstein, J.M., Woodruff, P. W.R., O'Craven, K., Savoy, R., Tsuang, M.T., & Rosen, B.R. (1998). A functional magnetic resonance imaging study of auditory vigilance with low and high infonnation .processing demands. Neuropsycholgy 12, 505–518.

Self LA, Moms J, Beam I, Frackowiak RS, Friston KJ, Dolan RI. Activation of reward circuitry in human opiate addicts. Eur J Neurosci. Mar. 1999; 11(3): 1042–8.

Sergent, J., Ohta, S., & MacDonald, B. (1992). Functional neuroanatomy of face and object processing. Brain 115, 15–36.

Serratrice O, Michel B. Pain in Parkinson's disease patients. Rev Rhum Engl Ed. Jun. 1999;66(6):331–8.

Shi, C., Davis, M. Pain Pathways involved in fear conditioning measured with fear–potentiated startle: lesion studies, The Journal of Neuroscience, Jan. 1, 1990, 19(1): 420–430.

Shizgal P. Neural basis of utility estimation. Current Opin Neurobiol. Apr. 1997,7(2): 198–206.

Shizgal, P., Schindler, D., and Rompre, R.–P. (1989). Forebrain neurons driven by rewarding stimulation of the medial forebrain bundle in the rat: comparison of psychophysical and electrophysiological estimates of refractory periods. Brain Res. 499, 234–248.

Sikes, R.W., and Vogt, B.A. (1992). Nociceptive neurons in area 24 of rabbit cingulate cortex. I Neurophysiol. 68(5): 1720–1732.

Silfverskiold, P .,& Risberg, J. (1989). Regional cerebral blood flow in depression and mania. Arch. Gen. Psychiatry 46, 253–259.

Spiegler, 8.J., Mishkin, M. (1981). Evidence for the sequential participation of inferior temporal cortex and amygdala in the acquisition of stimulus–reward associations. Behav. Brdin Res. 3, 303–317.

Spinoza, B. The Ethics—Part III: On the origin and nature of the emotions. In: The Ethics. Elwes, R.H.M. (Ed). 1883 Princeton Univ. Press, Princeton, New Jersey pp1–132.

Stein, E.A., Pankiewicz, J., Harsch, H.H., Cho, 1.K., Fuller, S.A., Hoffmann, R.G., Hawkins, M., Rao, S.M., Bandettini, P.A., and Bloom, A.S. (1998). Nicotine–induced limbic cortical activation in the human brain: a functional MRI study. Am. J. Psychiatry 155(8), 1009–1015.

Stern, C.E., and Passingham, R.E. (1996). The nucleus accumbens in monkeys (*Macaca fascicularis*): II Emotion and motivation. Behav. Brain Res. 75, 179–193.

Sutton, J.P., and Breiter, H.C. (1994). Neural scale invariance: an integrative model with implications for neuropathology. World Conference on Neural Networks 4, 667–672.

Sutton, S.K., and Davidson, R.J. (1997). Prefrontal brain symmetry: a biological substrate of the behavioral approach and inhibition systems. Psychological Science 8(3), 204–210.

Svoboda, K.R., Adams, C.E., and Lupica, C.R. (1999). Opioid receptor subtype expression defines morphologically distinct classes of hippocampal interneurons. J. Neurosci. 19(1), 85–95.

Talbot, I.D., Marrett, S., Evans, A.C., Meyer, E., Bushnell, M.C., and Duncan, G.H. (1991). Multiple representations of pain in human cerebral cortex. Science 251, 1355–1358.

Talairach, I., Toumoux, P. (1988). Co–planar Stereotaxic Atlas of the Human Brain Thieme Medical Publishers, New York, 2 pgs.

Thut, G., Schultz, W., Roelcke, U., Nienhusmeier, M., Missimer, I., Maguire, R.P., and Leenders, K.L. (1997). Activation of the human brain by monetary reward. NeuroReport 8, 1225–1228.

Toile TR KaufmalU1 T, Siessmeler T, Lautenbacher S, Berthele A, Munz F. Zieglgansberger W, Willoch F, Schwaiger M, Conrad B, Bartenstein P. Region–specific encoding of sensory and affective components of pain in the human brain: a positon emission tomography correlation analysis. Ann Neurol. Jan. 1999;45(1):40–7.

Tootell RB, Hadjikhani N. Attention –brains at work! Nat Neurosci. Mar. 2000,3(3):206–208.

Tootell, R.B., Dale, A.M., Sereno, M.I., and Malach, R. (1996). New images from human visual cortex. Trends Neurosci. 19(11), 481–489.

Tootell, R.B.H., Reppas, J.B., Kwong, K.K., Malach, R., Born, R.T Brady, TJ., Rosen, B.R., and Belliveau, J. W. (1995). Functional analysis of human MT and related visual cortical areas using magnetic resonance imaging. J. Neurosci. 15, 3215–3230.

Treede RD, Meyer RA, Raja SN, Campbell IN. Evidence for two different heat transduction mechanisms in nociceptive primary afferents innvervating monkey skin. J Physiol (Lond). Mar. 15, 1995;483 (Pt 3):747–58.

Tremblay L, Schultz w. Relative reward preference in primate orbitofrontal cortex. Nature. Apr. 22, 1999;398(6729):704–8.

Tseng, L.F. and Wang, Q. (1992). Forebrain sites differentially sensitive to β–endorphin and morphine for analgesia and release of Met–enkephalin in the pentobarbital– anesthesized rat. J. Pharmacol. Ex.p. Ther. 261(3), 1028–1036.

Turken AU, Swick D. Response selection in the human anterior cingulate cortex. Nat Neurosci. Oct. 1999;2(10):920–4.

Urban MG, Zahn PK, Oebhart OF. Descending facillatory influences from the rostral medial medulla mediate secondary, but not primary hyperalgesia in the rat. Neuroscience. May 1999;90(2):349–52.

Uytdenhoef, P., Portelange, P., Jacquy, J., Charles, G., Linowski, P., & Mendlewicz, J. (1983). Regional cerebnll blood flow and lateralized hemispheric dysfunction in depression. Brit. J. Psychiatry 143, 128–132.

Vaccarino, F.I. Bloom, F.E., and Koob, G.F. (1985). Blockade of nucleus accumbens opiate receptors attenuates the intravenous heroin reward in the rat. Psychopharmacology 86, 37 –42.

Vogt, B.A., Wiley, R.a., and Jensen, E.L (1995). Localization of mu and delta opioid receptors to anterior cingulate afferents and projection neurons and input/output model of mu regulation. Exp. Neural. 135(2), 83–92.

Vokow, N.D., Wang, G.J., Fischman, M. W., Foltin, R. W., Fowler, J.S., Aburnrad. N.N., Vitkun, S., Logan, J., aatley, $.1., Pappas, N., Hitzemann, R., and Shea, C.E. (1997). Relationship between subjective effects of cocaine and dopaminergic transporter occupancy. Nature 386, 827–830.

Wang, H., aracy, K.N., and Pickel, V.M. (1999). $\mu$–opioid and NMDA–type glutamate receptors are often colocalized in spiny neurons within patches of the caudate–putamen nucleus. J. Comp. Neurol. 412(1), 132–146.

Watanabe, M. (1996). Reward expectancy in primate prefrontal neurons. Nature 382, 629–632.

Watkins LR, Wiertelak EP, McGorry M, Martinez J, Schwartz B, Sisk D, Maier SF. Neurocircuitry of conditioned inhibition of analgesia: effects of amygdala, dorsal raphe, ventral medullary , and spinal cord lesions on anti-analgesia in the rat. Behav Neurosci. Apr. 1998; 112(2):360–78.

Whalen, P J., Rauch, S.L., Etcoff, N .L., McInemey, S.C., Lee, M.B., and Jenike, M.A. (1998). Masked presentations of emotional facial expressions modulate amygdala activity without explicit knowledge. J. Neurosci. 18, 411–418.

Wise RA. Addictive drugs and brain stimulation reward. Annu Rev Neurosci. 1996; 19:319–40.

Woodruff, G.N., McCarthy, P.S., and Walker, R.J. (1976). Studies on the pharmacology of neurons in the nucleus accumbens of the rat. Brain Res. 115, 233–242.

Woods, R.P., Cherry, S.R., and MaZ2.iotta, J.C. (1992). Rapid automated algorithm for aligning and reslicing PET images. J. Comput. Assist. Tomogr. 16, 620–633.

Wu MT, Hsieh JC, Xiong J, Yang CF, Pan HB, Chen YC, Tsai G, Rosen BR, Kwong KK. Central nervous pathway for acupuncture stimulation: localization of processing with functional MR imaging of the brain–preliminary experience. Radiology. Jul. 1999;212(1):133–41.

Yaksh, T.L. (1997). Pharmacology and mechanisms of opiod analgesic activity. Acta. Anaesthesiol. Scand. 41(1 Pt 2), 94–111.

Yaari, A., Eisenberg, E., Adler, R,. Chronic pain in holocaust survivors, Journal of Pain and Symptom Management, vol. 17, No. 3, Mar. 1999, 181o–187.

Yoshida, M., Yokoo, H., Mizoguchi, K., Kawahara, H., Tsuda, A.,, Nishikawa, T. Tanaka, M., Eating and drinking cause increased dopamine release in the nucleus accumbens and ventral tegmental area in the rat: measurement by in vivo microdialysis, Neuroscience Letters, 139 (192) 73–76, May 1992.

Yu. L.C., and Han, J.S. (1989). Involvement of arcuate nucleus of hypothalamus in the descending pathway from nucleus accumbens to periaqueductal grey subserving an antiinociceptive effect. Int. J. Neurosci. 48(1–2), 71–78.

Zubieta, I.–K., Dannals, R.F., and Frost, 1.1. (1999). Gender and age influences on human brain mu–opioid receptor binding measured by PET. Am. I. Psychiatry 156(6),842–848.

Zubieta, I.–K., Oorelick, D.A., Stauffer, R., Ravert, H.T., Dannals, R.F., and Frost, J.J. (1996). Increased mu opiod receptor binding detected by PET in cocaine–dependent men is associated with cocaine craving. Nat. Med. 2(II), 1225–1229.

Becerra et al. "Early Activation of Reward/Aversive Circuitry Following Noxious Thermal Stimuli: Dissociation of Motivation–Emotion Circuitry from Sensory–Discriminative Circuitry" (Published as "Reward Circuitry Activation by Noxious Thermal Stimuli") Neuron. 2001 32:927–46.

* cited by examiner

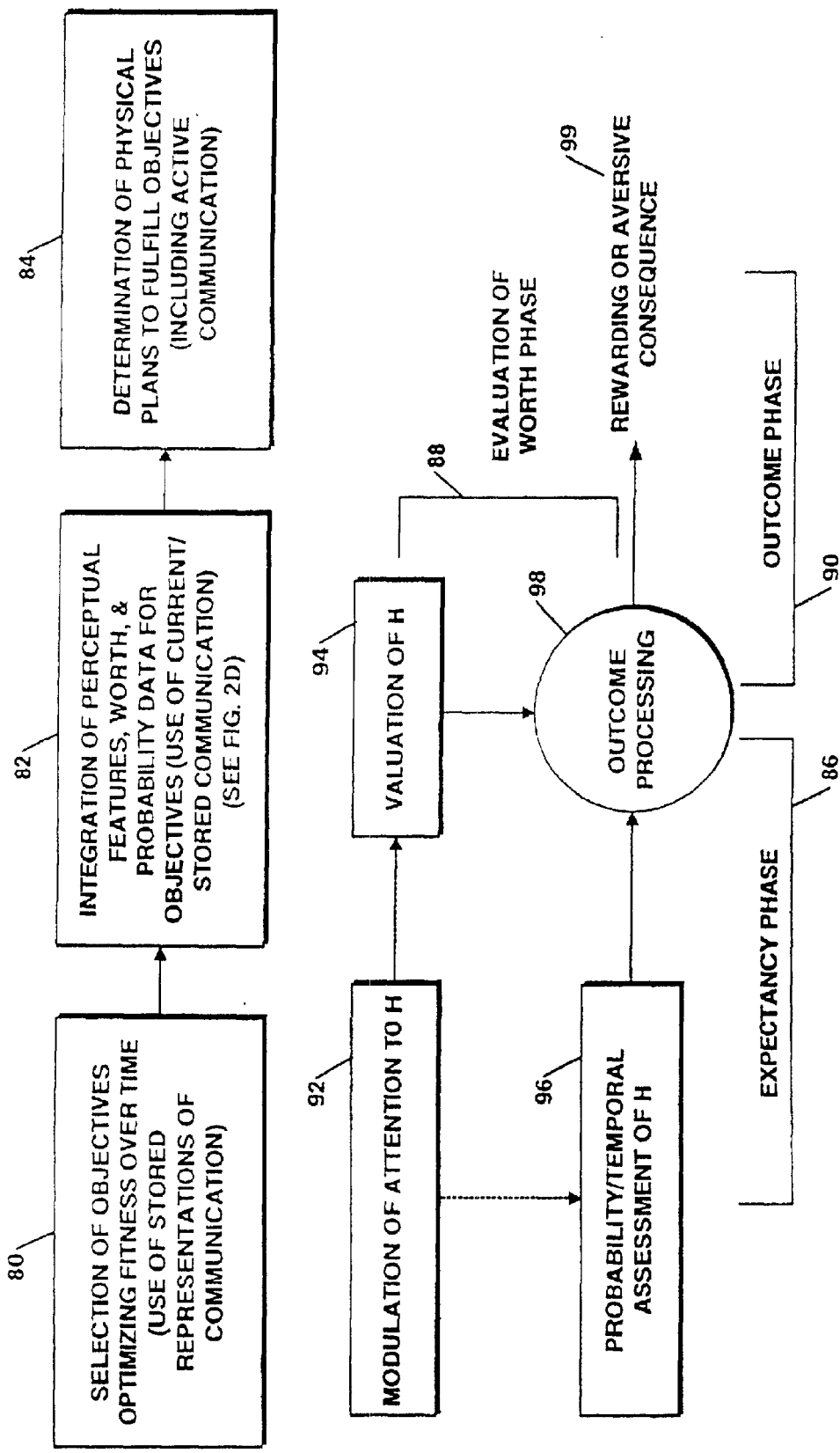

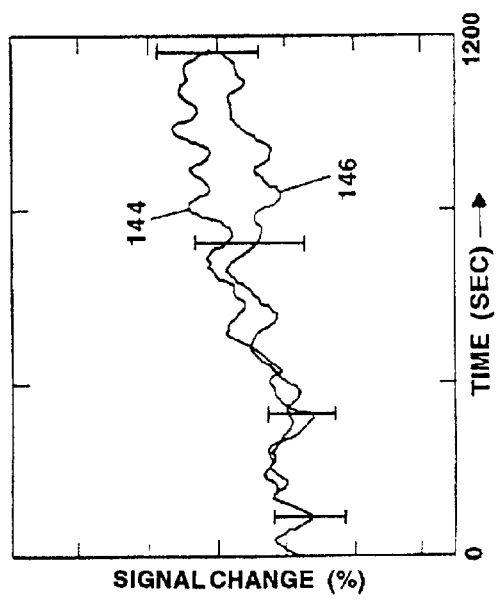
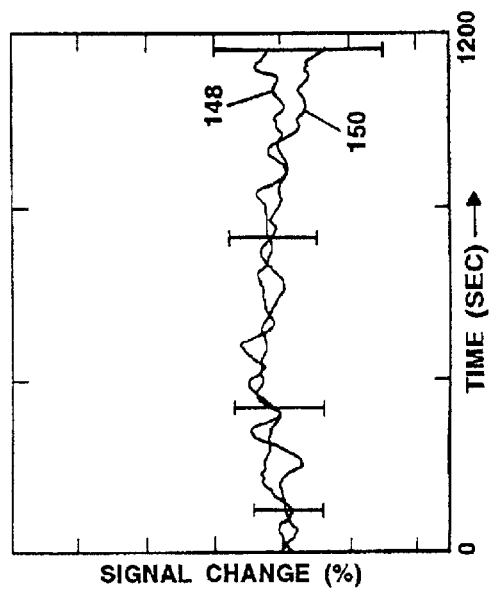
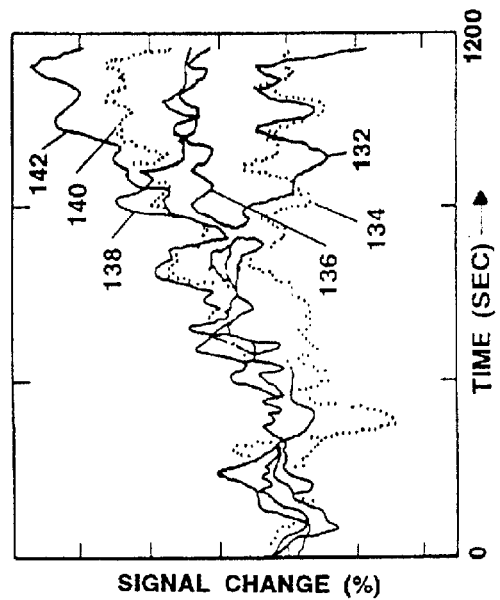
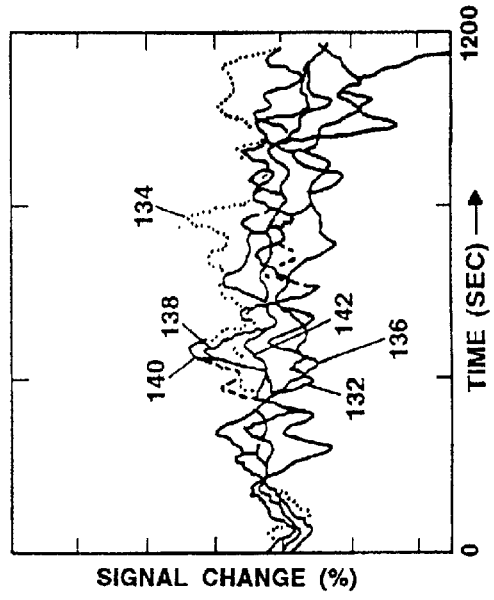
Figure 3A
Figure 3B
Figure 3C
Figure 3D

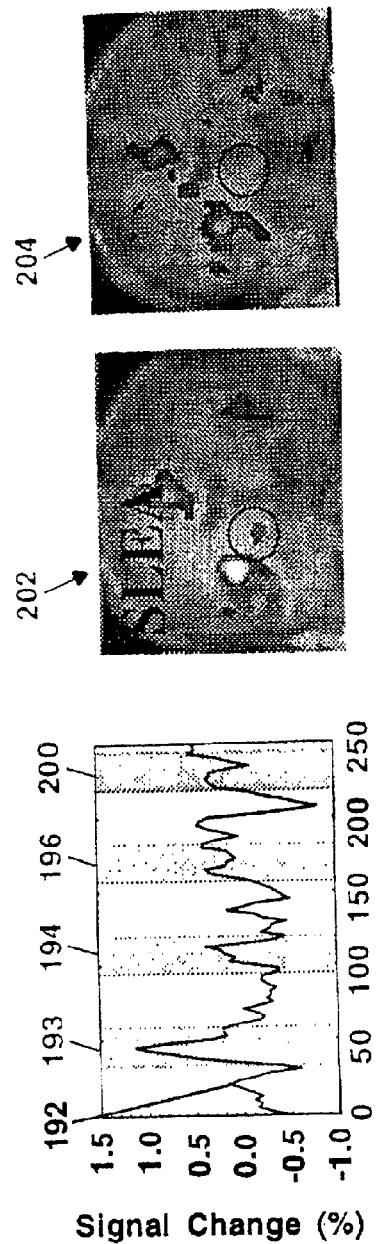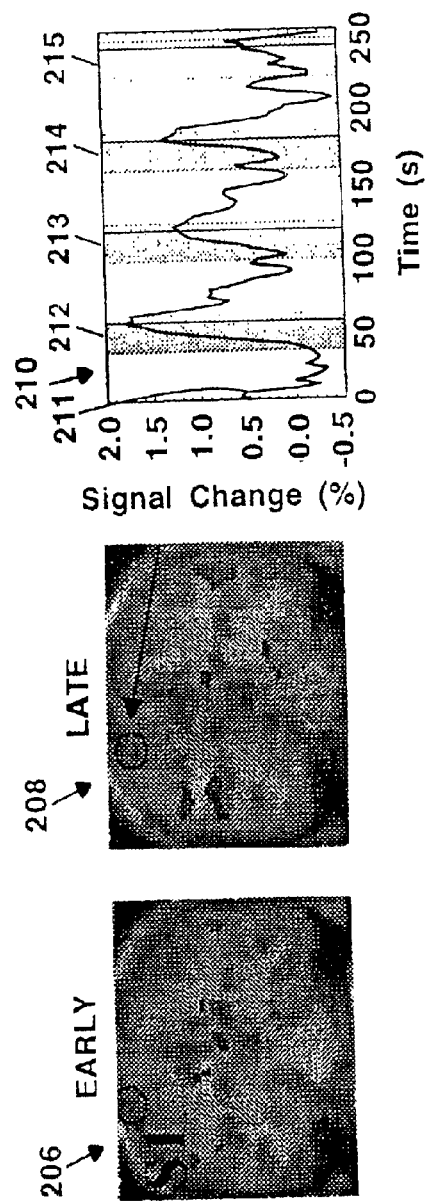
Figure 3J  Figure 3K  Figure 3L
Figure 3M  Figure 3N  Figure 3O

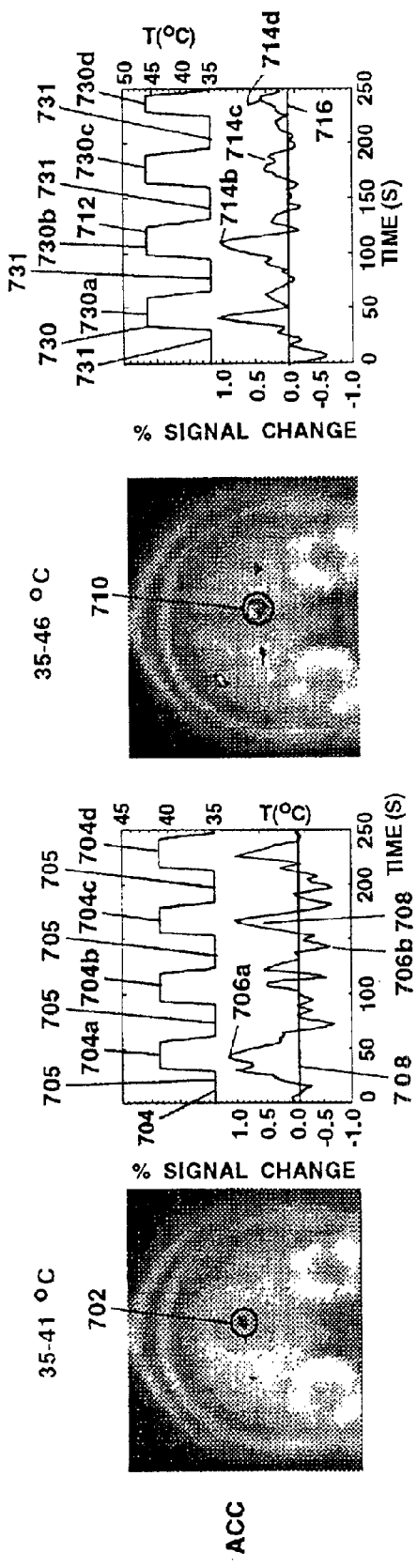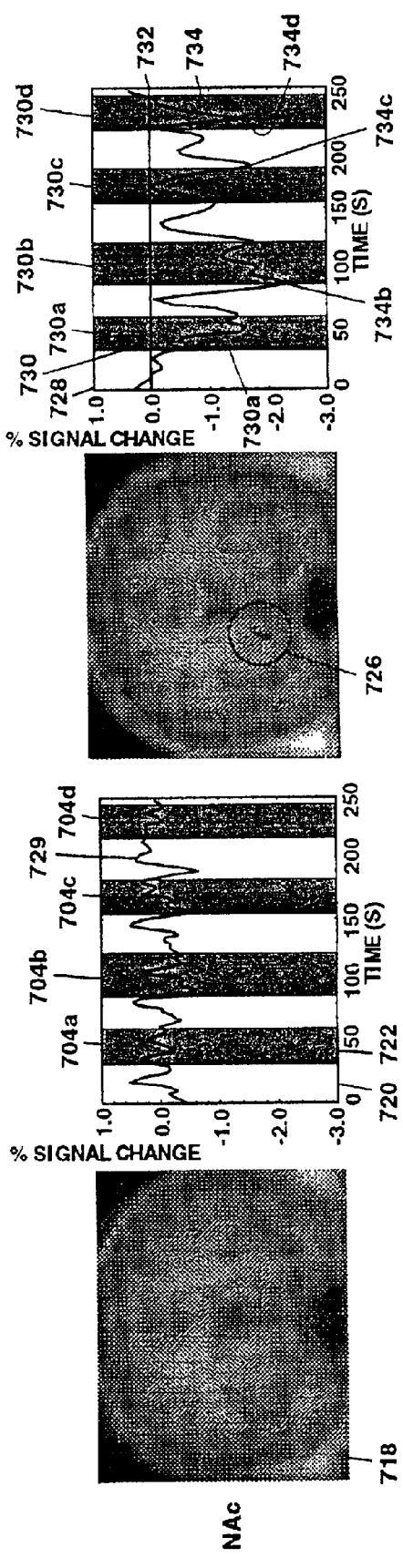
Figure 7A, Figure 7B, Figure 7C, Figure 7D, Figure 7E, Figure 7F, Figure 7G, Figure 7H

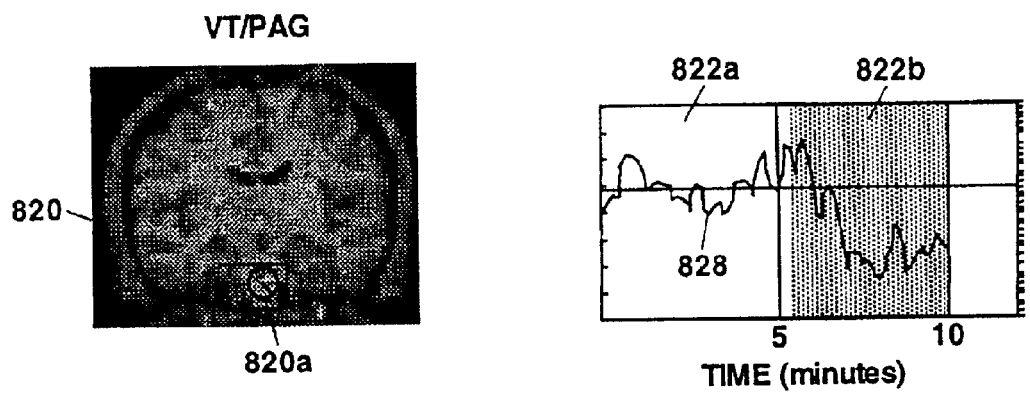
Figure 10E
Figure 10F
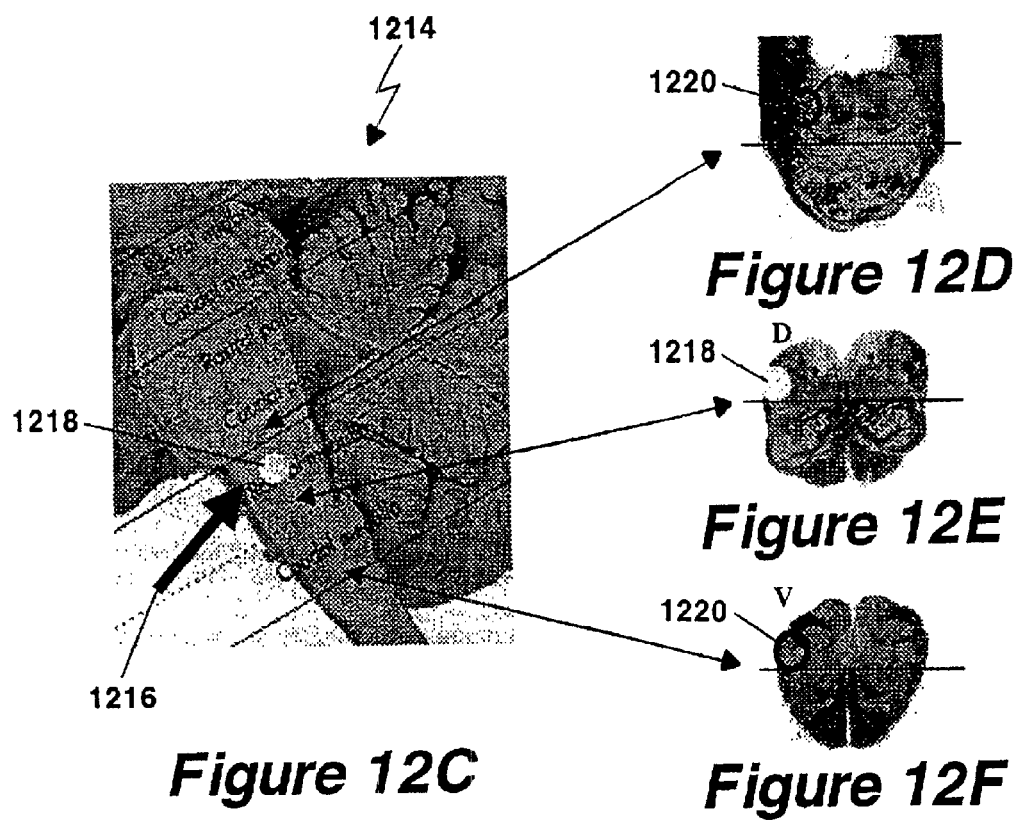
Figure 12C
Figure 12D
Figure 12E
Figure 12F

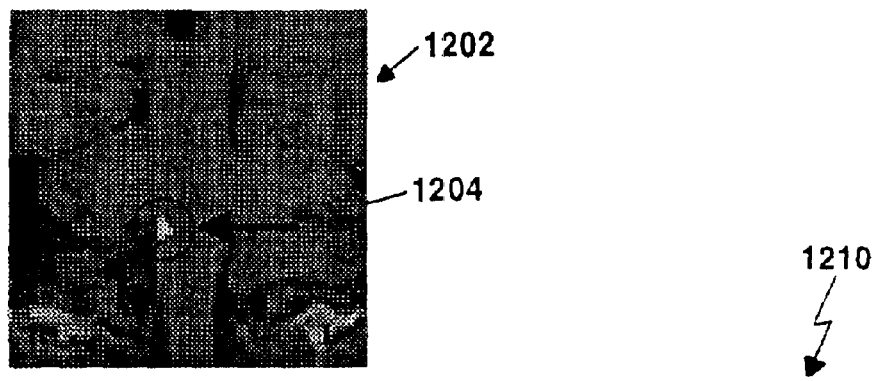
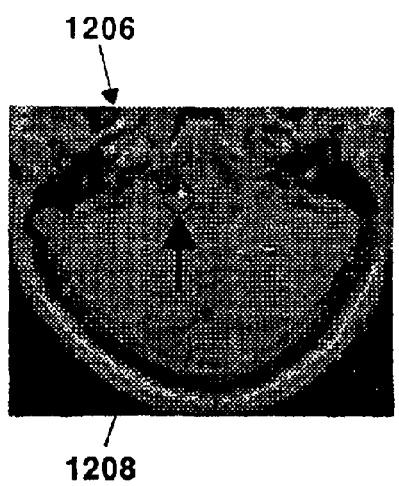
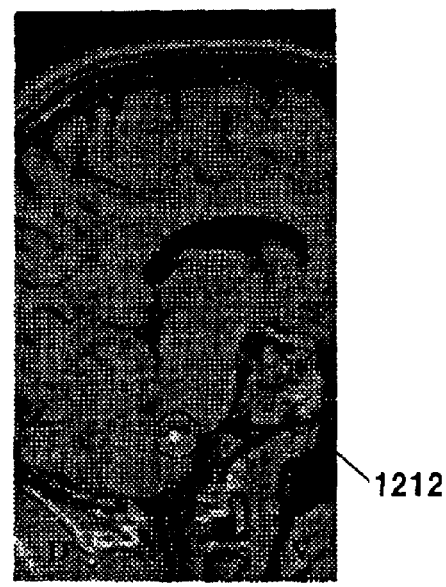
Figure 12
Figure 12A
Figure 12B

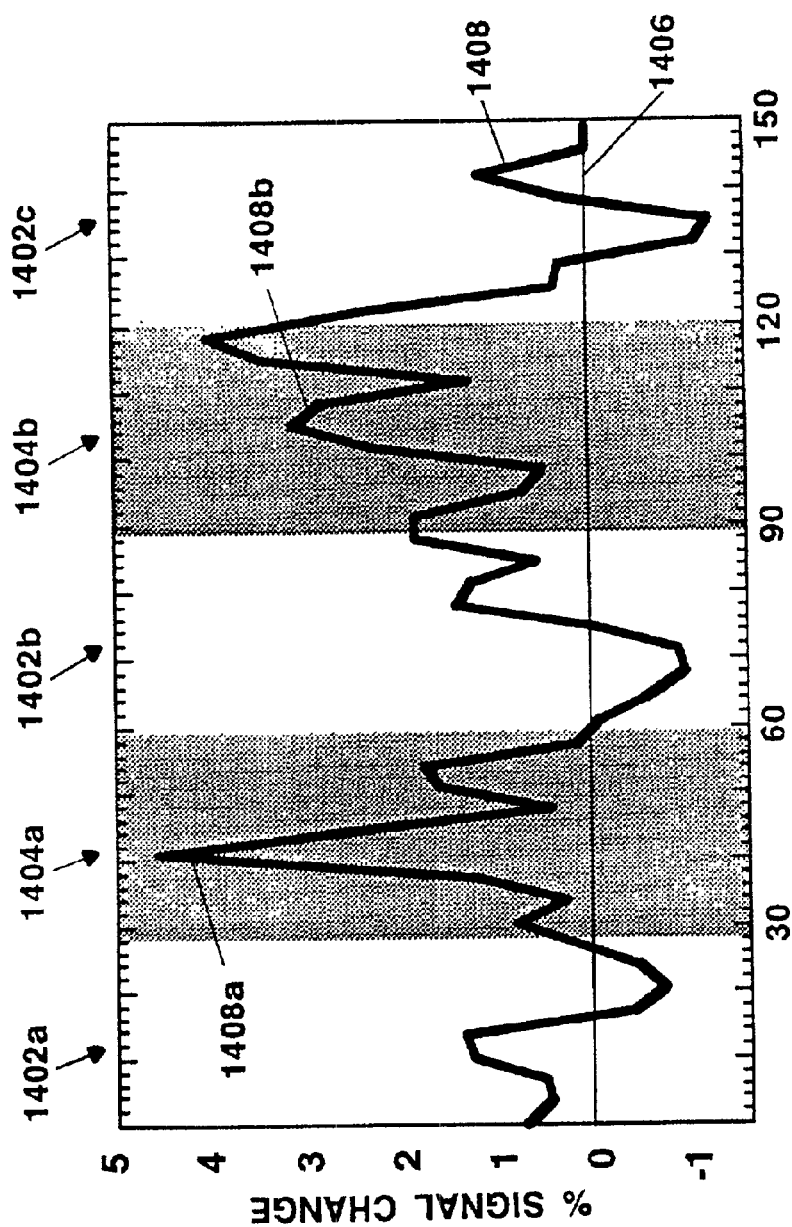
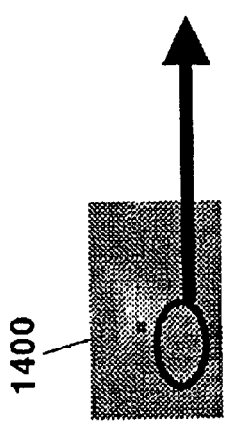
Figure 14A
Figure 14B

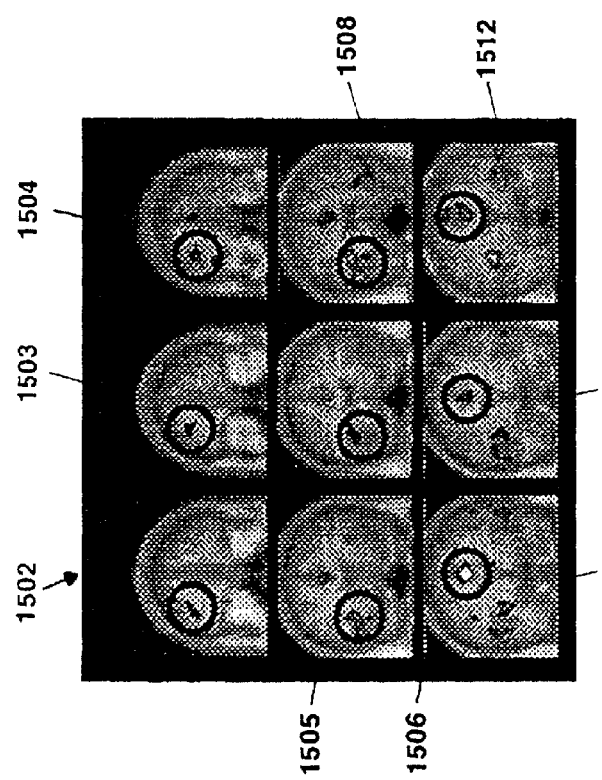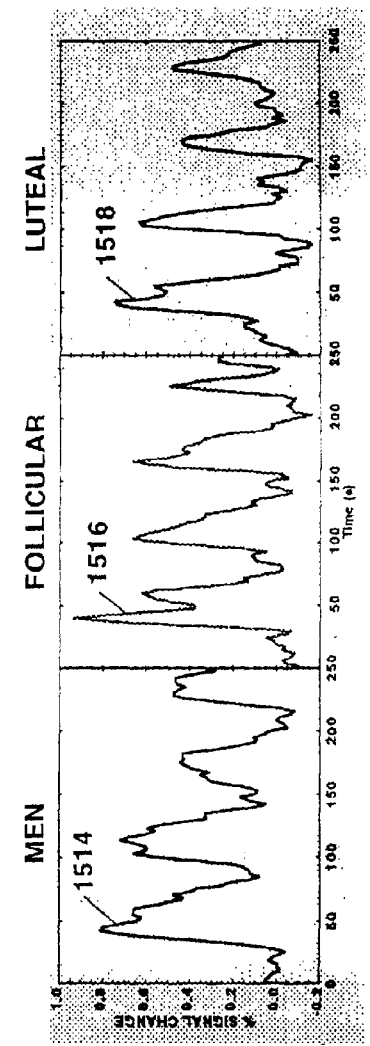
Figure 15
Figure 15A  Figure 15B  Figure 15C

METHOD AND APPARATUS FOR OBJECTIVELY MEASURING PAIN, PAIN TREATMENT AND OTHER RELATED TECHNIQUES

RELATED APPLICATIONS

This application claims the benefit of U.S. Provisional Application No. 60/193,300 filed on Mar. 30, 2000 and U.S. Provisional Application No. 60/228,950 filed on Aug. 28, 2000. This application is also a continuation-in-part of U.S. application Ser. No. 09/729,665 filed on Dec. 4, 2000, which claims the benefit of U.S. Provisional Application No. 60/168,660 filed on Dec. 2, 1999, U.S. Provisional Application No. 60/193,300 filed on Mar. 30, 2000 and U.S. Provisional Application No. 60/228,950 filed on Aug. 28, 2000 all of which are hereby incorporated herein by reference in their entireties.

GOVERNMENT RIGHTS

None

FIELD OF THE INVENTION

This invention relates to non-invasive measurement methods and systems and more particularly to a method and apparatus for measuring indices of brain activity during acute and chronic pain, and the ability to measure treatment effects on acute or chronic pain. It is also a novel method for determining quantitative indices from neuroimaging signals.

BACKGROUND OF THE INVENTION

As is known in the art, magnetic resonance imaging (MRI) (also referred to as nuclear magnetic resonance or NMR) and other non-invasive techniques such as functional magnetic resonance imaging (fMRI), magnetic resonance spectroscopy (MRS), electroencephgraphy (EEG), magnetoencephalography (MEG), positron emission tomography (PET), optical imaging (OR), single photon emission computer tomography (SPECT), functional computerized tomography (fCT) have been proposed to be able to directly examine a combination of brain (cortical and subcortical), brainstem and spinal cord regions in humans for the evaluation of acute and chronic pain states, analgesic responses, therapies including pharmacological or gene products, and placebo responses.

To date, this goal has not been accomplished. The major hurdle to this proposed goal has been the inability to define an objective set of indices that characterize the pain state, its progression over time and its alteration through intervention.

Pain is a complex response that has been functionally categorized into sensory, adaptive, and affective components. The sensory aspect includes information about stimulus location and intensity while the adaptive component may be considered to be the activation of endogenous pain modulation and motor planning for escape responses. The affective component appears to include evaluation of pain unpleasantness and stimulus threat as well as negative emotions triggered by memory and context of the painful stimulus. Extensive electrophysiological research in animals has defined likely neuroanatomical substrates for some of the sensory attributes of pain, such as localization and intensity, and some of the adaptive responses, such as descending analgesia. Other regions activated by painful stimuli have also been identified which may be involved in the affective response, however the neural substrates for the motivational and emotional response to pain remain a topic of debate.

Ronald Melzack and Kenneth Casey state "To consider only the sensory features of pain, and ignore its motivational and affective properties, is to look at only part of the problem, not even the most important part at that". In Donald Price's treatise on the Psychology of Pain, he defines pain as a somatic perception containing: (1) a bodily sensation with qualities like those reported during tissue-damaging stimulation; (2) an experienced threat associated with this sensation and (3) a feeling of unpleasantness or other negative emotion based on this experienced threat.

To date, although there are clear affective, motivational and emotional components of pain that can be evaluated subjectively, a clear delineation of the neural circuitry involved in the motivational and emotional aspects of pain are only beginning to be evaluated in animal models. A typical current formulation of CNS systems involved in the evaluation of pain intensity (algosity) and unpleasantness ("classic pain circuitry") is presented in "Pain An Unpleasant Topic," Pain 1999 Suppl. 6 §61–69, H. L. Fields.

Despite hypotheses about what was constitutes "classic pain circuitry", the issue of which brain regions process sensory information vs. those that mediate affective responses remains an area of active discussion. Indeed, it is unclear whether unpleasantness is a sensation or an emotion. Another approach for determining which neuroanatomical regions mediate emotional processes regarding pain stimuli might focus on those regions known to be active for motivational processes which underlie emotion. When animals organize behavior in response to aversive or rewarding stimuli, they respond to multiple informational dimensions of these goal-objects or events. These informational dimensions include rate, delay, incidence, intensity and amount and location of the stimulus. A number of brain regions have been consistently implicated in the organization of responses to aversive and rewarding stimuli in animals. More recently, these regions have been specifically implicated in reward processes in humans. These regions, which include the nucleus accumbens (NAc), the sublenticular extended amygdala of the basal forebrain (SLEA), the amygdala, the ventral tegmentum (VT) and the orbital gyrus (GOb), have been shown to be activated in studies of drug-associated reward, in general, these regions are thought to be important for information processing in the service of emotional and motivational states. Traditionally, these regions have been considered in the domain of rewarding rather than aversive stimuli, though, it has been previously postulated that pain and reward are at opposite ends of the same behavioral spectrum.

Motivational states (including aversive states such as pain) which lead to goal-directed behavior depend on a complex informatics system comprised of a set of subprocesses for the moment-by-moment modulation of behavior. The informatics subprocesses can be grouped into three general categories for (1) perceptual processing of goal-objects and other putative rewards, (2) valuation of goal-object worth, and (3) approximation of temporal information and conditional probabilities about the potential reward. The amygdala appears to be a central component of the brain circuitry mediating the first informatics subprocess, while other regions such as the sublenticular extended amygdala (SLEA) of the basal forebrain, and the nucleus accumbens (NAc) appear to be central to the second and third subprocesses respectively. In regard to reward function, input from the dopaminergic neurons of the ventral tegmentum (VT) to the amygdala, SLEA, and NAc is an important feature of this extended system. To date objective indices of function in these regions have not been directly connected to the perception, evaluation, and integration of painful stimuli.

Recent neuroimaging studies have sought to define the principal CNS structures involved in the perception, evaluation and integration of painful stimuli. These studies have contributed to our understanding of the complex nature of the CNS response to pain but have not clearly separated circuitry involved in reward/aversion and emotion from circuitry involved with sensory processing. Direct interrogation of any brain circuitry to objectively define the pain state has hithertofore not been accomplished.

One means for evaluating the brain circuitry mediating acute and chronic pain involves "invasive" approaches. These approaches, have been predominantly restricted to animal research and methods such as placing electrodes into the brain of an animal for electrical recordings, or sacrificing the animal to collect brain tissue for cell culture, immunohistochemistry or other molecular biological techniques.

It would, be desirable to provide a technique and system to non-invasively interrogate the brain of an individual human/animal regarding acute and chronic pain. It would be further desirable to be able to objectively assess pain in humans or animals, or the effects of therapeutic interventions on acute and chronic pain.

SUMMARY OF THE INVENTION

In accordance with the present invention, a system includes a non-invasive measurement apparatus for obtaining signals of central nervous system (CNS) activity, a localization processor, coupled to the non-invasive measurement system, for localizing signals to specific anatomical and functional brain regions, a correlator for correlating an experimental process to brain activity and a processor for interpreting the result of the correlation to a specific application.

With this particular arrangement, a system for measuring indices of brain activity during motivational and emotional function is provided. It should be appreciated that the non-invasive measurement apparatus may be provided as one which can implement fMRI, PET, IR, SPECT, fCT, MRS, MEG and EEG or other techniques to non-invasively measure indices of brain activity during motivational and emotional function. The CNS signal processor and the correlation processor cooperate to determine indices of brain activity during motivational and emotional function. Once CNS signals are obtained, the signals are localized to examine the function in a particular region of the brain. The particular manner in which such the signals are localized are dependent upon a variety of factors including but not limited to the technique or techniques (including equipment) used to extract the signals. Once signals are extracted, the correlation processor correlates empirical data with the measured signals and interprets the results of the correlation to a specific application. It should be appreciated that although the CNS apparatus and correlation processors are described as separate and distinct pieces of equipment, in practice the functions performed by these pieces of equipment may be performed by a single processor or by more than one processor.

In accordance with a further aspect of the present invention, a method for measuring indices of brain activity during motivational and emotional function includes the steps of non-invasively acquiring central nervous system (CNS) signals, statistically analyzing and then localizing the CNS signals to specific anatomical and functional brain regions, evaluating the CNS signals with regard to patterns of activity within and between functional brain regions, and interpreting the results of the correlation to a specific application. With this particular arrangement, a technique for measuring indices of brain activity during motivational and emotional function is provided. In one embodiment, the CNS signals are acquired (e.g. via an MRI, PET or other non-invasive measurement system) while the subject undergoes one or more experimental paradigms focused on one or more motivation/emotion processes. In other embodiments, the CNS signals are acquired while the subject is exposed to certain stimulus (e.g. the subject views photographs of people or food or consumer products) or while the subject performs particular tasks (e.g. presses a bar to get a particular result). Alternatively, the subject could perform some combination of the above tasks.

Data associated with the experimental/paradigm is correlated with patterns of activity and other measures.

In the step of interpreting the results of the correlation to a specific application, the subject's brain response to a known stimulus in a particular application is measured. For example, if a subject is being tested to determine whether or how much they like a particular product, the amount and/or intensity of activity in certain regions of the subject's brain is compared with signals from the subject's brain (or from a database of known brain region responses) in response to stimuli considered to elicit from a subject responses with a limited variance (e.g., extreme liking vs. extreme aversion). Based upon this information, a determination can be made as to whether or how much the subject liked the particular product. The comparison can be based on one or more of spatial, temporal, integration-derivative characteristics, moment analysis, laterality, synchrony, volume, differential power function, power spectrum analysis and matrix values. In one embodiment for example, brain responses in the amygdala region of the brain is evaluated for habituation to aversion stimuli. If it does not habituate at or below a population normed average then individuals who are being tested with the diagnosis of obsessive compulsive disorder will not be referred for behavioral therapy since a common component of behavioral therapy is the ability to habituate or be de-conditioned to aversive stimuli.

BRIEF DESCRIPTION OF THE DRAWINGS

The foregoing features of the invention as well as the invention itself may be more fully understood from the following detailed description of the drawings, in which:

FIG. 2C is a generalized schema which illustrates three phases of motivational function;

FIG. 2D is a schema dissecting one of the three phases of motivational function into its subcomponents;

FIG. 3A is a plot of signal strength from the left nucleus accumbens vs. time for morphine infusions;

FIG. 3B is a plot of signal strength from the left nucleus accumbens vs. time for morphine infusions; FIG. 3C is a plot of signal strength from the left and right nucleus accumbens vs. time for morphine infusions;

FIG. 3D is a plot of signal strength from the left and right nucleus accumbens vs. time for saline infusions;

FIG. 3J is a plot of signal change vs. time for the SLEA;

FIG. 3K is a diagram of a portion of a brain showing early phase activation of the SLEA brain region in response to an aversive thermal stimulus;

FIG. 3L is a diagram of a portion of a brain showing no late phase activation of the SLEA brain region to an aversive thermal stimulus;

FIG. 3M is a diagram of an early phase activation map of the primary somatosensory cortex (SI) in response to an aversive thermal stimulus;

FIG. 3N is a diagram of a late phase an activation map of the primary somatosensory cortex (SI) in response to a an aversive thermal stimulus;

FIG. 3O is a plot of signal change vs. time of a signal in the primary somatosensory cortex (SI) of a brain;

FIG. 7A is a diagram of a portion of a brain showing activation of the aCG brain region in response to a thermal stimulus;

FIG. 7B is a plot of signal change vs. time of a signal in aCG brain region in response to a thermal stimulus;

FIG. 7C is a diagram of a portion of a brain showing activation of the aCG brain region in response to a painful thermal stimulus;

FIG. 7D is a plot of signal change vs. time of a signal in aCG brain region in response to a painful thermal stimulus;

FIG. 7E is a diagram of a portion of a brain showing activation of the NAc brain region in response to a thermal stimulus;

FIG. 7F is a plot of signal change vs. time of a signal in NAc brain region in response to a thermal stimulus;

FIG. 7G is a diagram of a portion of a brain showing activation of the NAc brain region in response to a painful thermal stimulus;

FIG. 7H is a plot of signal change vs. time of a signal in the NAc brain region in response to a painful thermal stimulus;

FIG. 10E is a diagram of a portion of a brain showing activation of the VT/PAG brain region in response to a thermal stimulus during the intravenous administration of naloxone;

FIG. 10F is a plot of signal change vs. image number of a time course of a signal in VT/PAG brain region in response to a thermal stimulus before and during the intravenous administration of naloxone;

FIGS. 12A–12F are a series of figures which illustrate activation in the brainstem region spV following noxious heat (46° C.) applied to the skin of the face;

FIG. 14A is a diagram of a portion of a brain showing activation of the NAc brain region of subjects during brush-induced allodynia in a subject with chronic pain;

FIG. 14B is a plot of signal change vs. time of a signal in the NAc brain region of subjects during brush-induced allodynia in a subject with chronic pain;

FIG. 15 is a set of statistical maps showing brain activation for men (left column), women in the mid-follicular stage (middle column), and women in the mid-luteal phase (right column) for the perforated cortex (top row), insula (middle row), and aCG (bottom row);

FIG. 15A is a plot of signal change vs. time for the mean hemodynamic response for all significantly activated voxels in the brain for men;

FIG. 15B is a plot of signal change vs. time for the mean hemodynamic response for all significantly activated voxels in the brain for women in the mid-follicular stay of their menstrual cycle;

FIG. 15C is a plot of signal change vs. time for the mean hemodynamic response for all significantly activated voxels in the brain for women in the mid-luteal stage of their menstrual stage;

DESCRIPTION OF THE PREFERRED EMBODIMENTS

Before proceeding with a description of the invention, some terminology is explained. As used therein below, the term "central nervous system" or "CNS" as referred to in the descriptions below includes both the brainstem and spinal cord regions. Reference is also made herein to noninvasively obtaining signals of a CNS. Such references refer to recording CNS signals noninvasively. It should be appreciated that in some applications it may be desirable or necessary to inject a substance (e.g. a dye or other substance) into a subject prior to recording the CNS signals. The signal responses, however, are still measured in a noninvasive manner.

Figure 1:
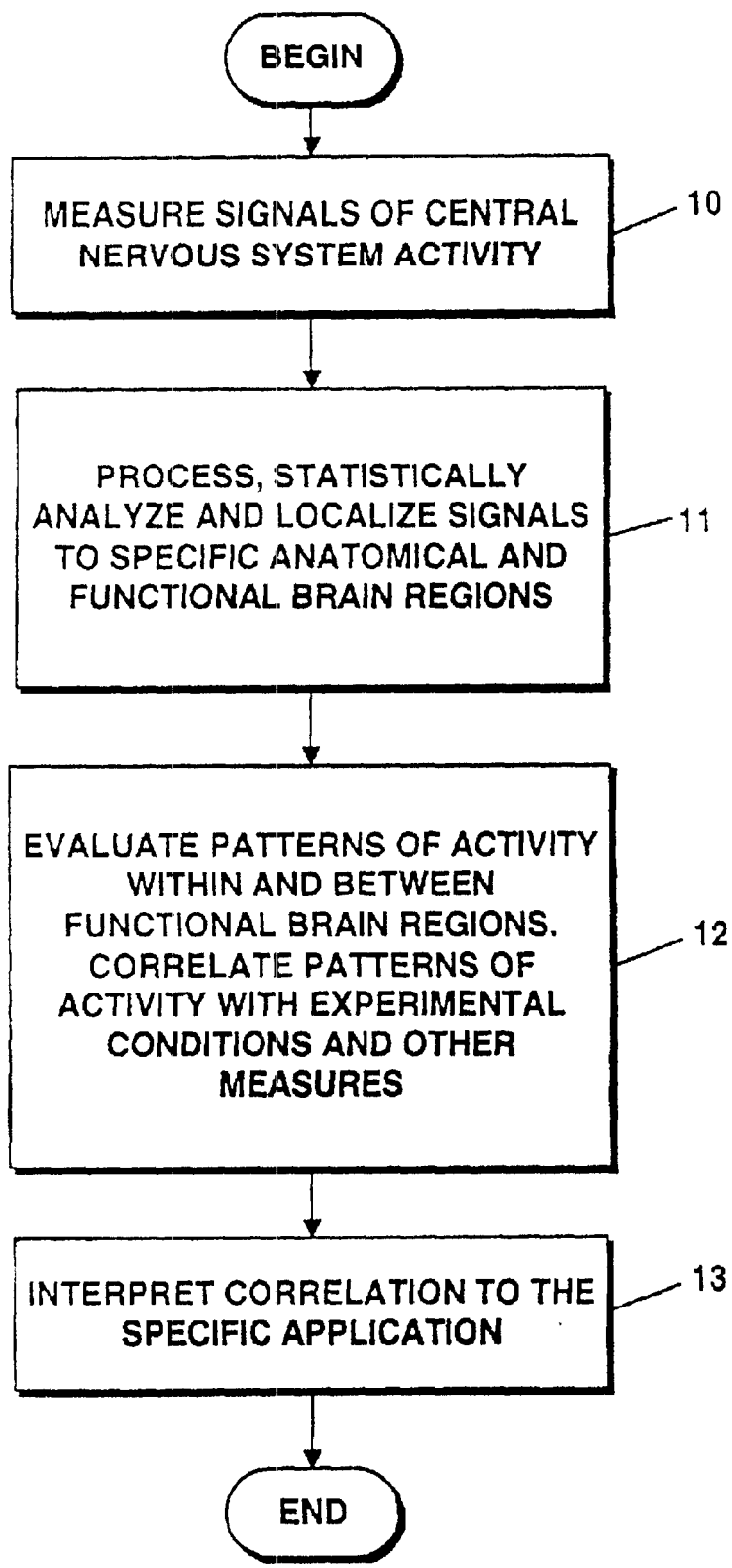
FIG. 1 is a flow diagram showing a general method for measuring indices of central nervous system activity during motivational and emotional function and determining indices of brain activity during motivational and emotional function.

Referring now to FIG. 1, a flow diagram shows the processing to determine indices of Central Nervous System (CNS) activity during motivational and emotional function. Such processing may be performed by a processing apparatus which may, for example, be provided as part of non-invasive measurement system such as that to be described below in conjunction with FIG. 4.

In the flow diagram of FIGS. 1 and 5A–5C, the rectangular elements in the flow diagrams are herein denoted "processing blocks" and represent computer software instructions or groups of instructions.

Alternatively, the processing blocks represent steps performed by functionally equivalent circuits such as a digital signal processor circuit or an application specific integrated circuit (ASIC). It should be appreciated that some of the steps described in the flow diagram may be implemented via computer software while others may be implemented in a different manner e.g. via an empirical procedure. The flow diagrams do not depict the syntax of any particular programming language. Rather, the flow diagrams illustrates the functional information one of ordinary skill in the art requires to fabricate circuits or to generate computer software to perform the processing required of the particular apparatus. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention.

Turning now to FIG. 1, processing begins in step 10 in which after positioning subjects to be tested (e.g. persons who are under going a lie detection test) and instructing the subjects to remain as still as possible, CNS signals are acquired. A measuring apparatus which non-invasively obtains the CNS signals is used. In one embodiment, the subject to be tested is placed in a brain scanner of an MRI, fMRI, MEG, fCT, OI, SPECT, or PET system of the type to be described below in conjunction with FIG. 4.

The CNS signals can be acquired while the subject undergoes an experimental paradigm focused on one or more "motivation/emotion" processes. Alternatively, the CNS signals can be acquired while the subject is exposed to certain stimuli (e.g. the subject views photographs of people or food or consumer products) or while the subject performs particular tasks (e.g. presses a bar to get a particular result). Alternatively still, the subject can perform two or more of the above tasks while the CNS signals are obtained.

Processing then proceeds to step 11 where the non-invasively obtained CNS signals are statistically analyzed and then localized to specific anatomical and functional brain regions. The details of the processes for statistically analyzing the CNS signals and localizing the signals to specific brain regions are described below in conjunction with FIGS. 3–30 and 5A–5C.

Processing next proceeds to processing step 12 where the CNS signals obtained in step 10 are evaluated with regard to patterns of activity within and between functional brain regions. Data associated with the experimental paradigm is correlated with patterns of activity and other measures.

In process step 13, an interpretation of the correlation obtained in step 12 to a specific application is then made. In this step, the subject's response to a known response for a particular application is made. For example, if a subject is being tested to determine whether or how much they like a particular product, the amount and/or intensity of responses in certain regions of the subject's brain is compared with predetermined responses from the subject's brain (or from a database of signals corresponding to known brain region responses) in response to stimuli which elicits a response from the subject considered to be statistically normal. By comparing the response generated by the subject when exposed to the particular product with the premeasured response, a variation from the subjects normal response can be found. Based upon this information, a determination can be made as to whether or how much the subject liked the particular product. In another embodiment, brain responses in the amygdala region of the brain are evaluated for habituation to aversion stimuli. If the amygdala region does not habituate at or below a population normed average then individuals who are being tested with the diagnosis of obsessive compulsive disorder will not be referred for behavioral therapy since a common component of behavioral therapy is the ability to habituate or be de-conditioned to aversive stimuli.

It should be appreciated that the responses are measured in particular regions of the subject's brain. The particular brain regions in which the responses should be measured depend, at least in part, upon the type of determination trying to be made. For example, if one is trying to determine whether a subject likes a particular object, then the response in a first plurality of brain regions are examined. If, on the other hand, one is trying to determine whether a subject is being truthful, then the response in a second plurality of brain regions are examined.

Figure 2A:
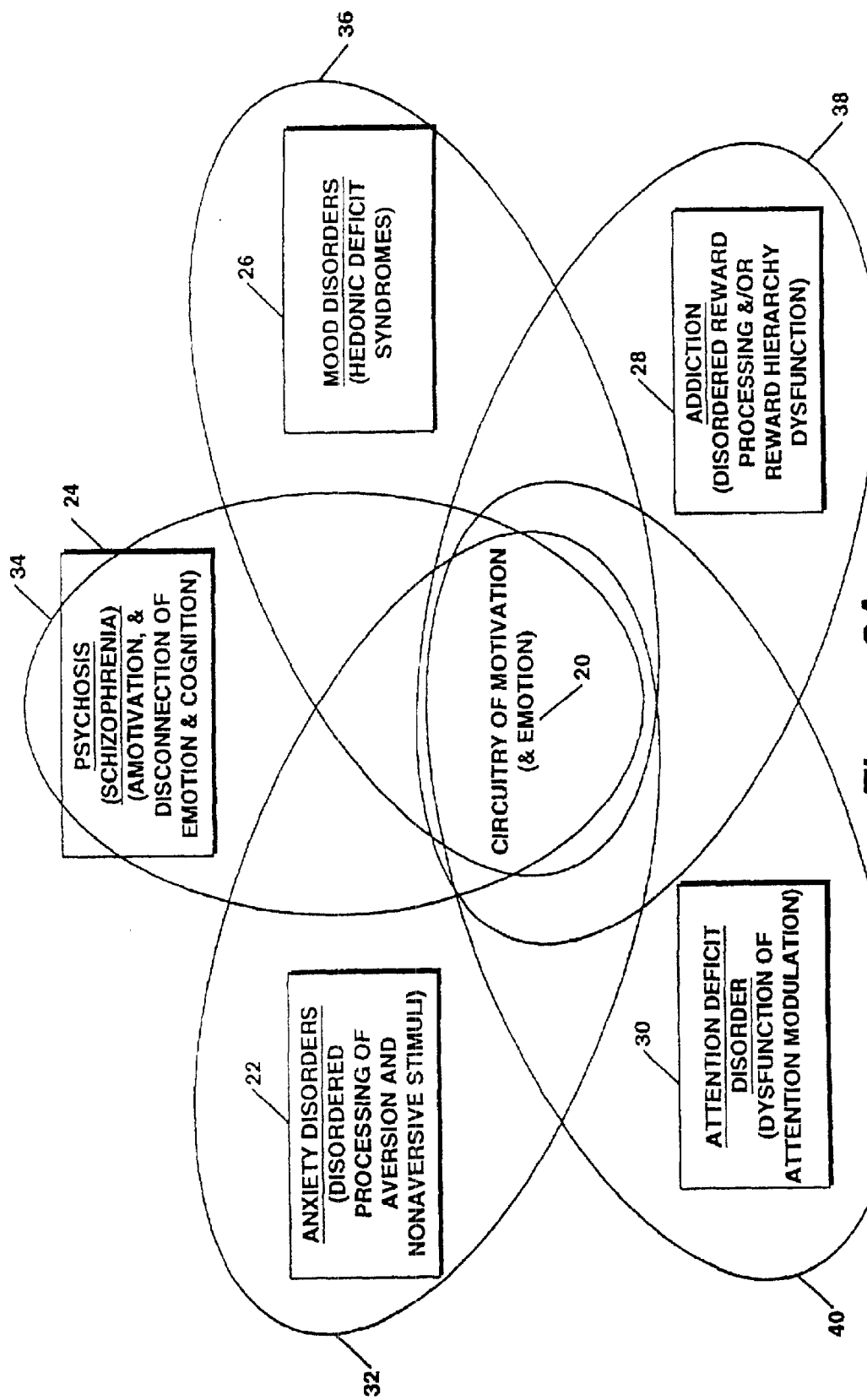
FIG. 2A is a schema of brain functional illness and its relationship to motivation/emotion function.

FIG. 2A is a schema of brain functional illness and its relationship to motivation/emotion function. That is, FIG.

2A illustrates the linkage of functional illness to motivation and emotion. Psychiatric illnesses, pain disorders, and illnesses producing neuropsychiatric dysfunction are examples of brain functional illnesses. At the core of all psychiatric illness, is some dysfunction of motivation/emotion. This has been most closely evaluated for substance abuse/addiction. The schema of FIG. 2A shows that relationships between circuitry of motivation 20 and a plurality of different categories of disorders designated by reference numbers 22–30 exists. Oval shaped reference lines 32–40 indicate that relationships exist between each of the disorder categories 32–40 and the circuitry of motivation and emotion 20. The details of the circuitry of motivation and emotion 20 are described in conjunction with FIGS. 3–5C below.

FIG. 2A illustrates the linkage between psychiatric disease and dysfunction of all or components of the circuitry of motivation or emotion. Thus, whatever the cause of the dysfunction, this cause can be identified in the circuit 20. The circuitry of motivation 20 is related via a relationship 22 to anxiety disorders 24. The precise relationship 32 is reported to include altered function of amagdala subnuclei shown in FIG. 3, though the full details remain a topic of current research. The circuitry of motivation 20 is also related via relationship 34 to psychosis 24. In this case the precise relationship is reported to involve altered function of the ventral tegmentum and prefrontal cortex illustrated in FIG. 3, and potentially the thalamus. Again, research continues to seek the details of relationship 34.

The circuitry of motivation 20 is further related via relationship 38 to addiction 28. Extensive research implicates the nucleus accumbuns, amygdala subnuclei, SLEA, ventral tegmentum, and orbital cortex with the development and progression of addictive disorders.

The circuitry of motivation 20 is related via relationship 36 to mood disorders 26. Currently, motivation circuitry such as the amygdala subnuclei and prefrontal cortex have been connected to hedonic defect syndromes.

Lastly, the circuitry of motivation 20 is related via relationship 40 to attention deficit disorder 30. Motivation circuitry implicated in disorders of attentional dysfunction include the ventral tegmentum and prefrontal cortex.

Figure 2B:
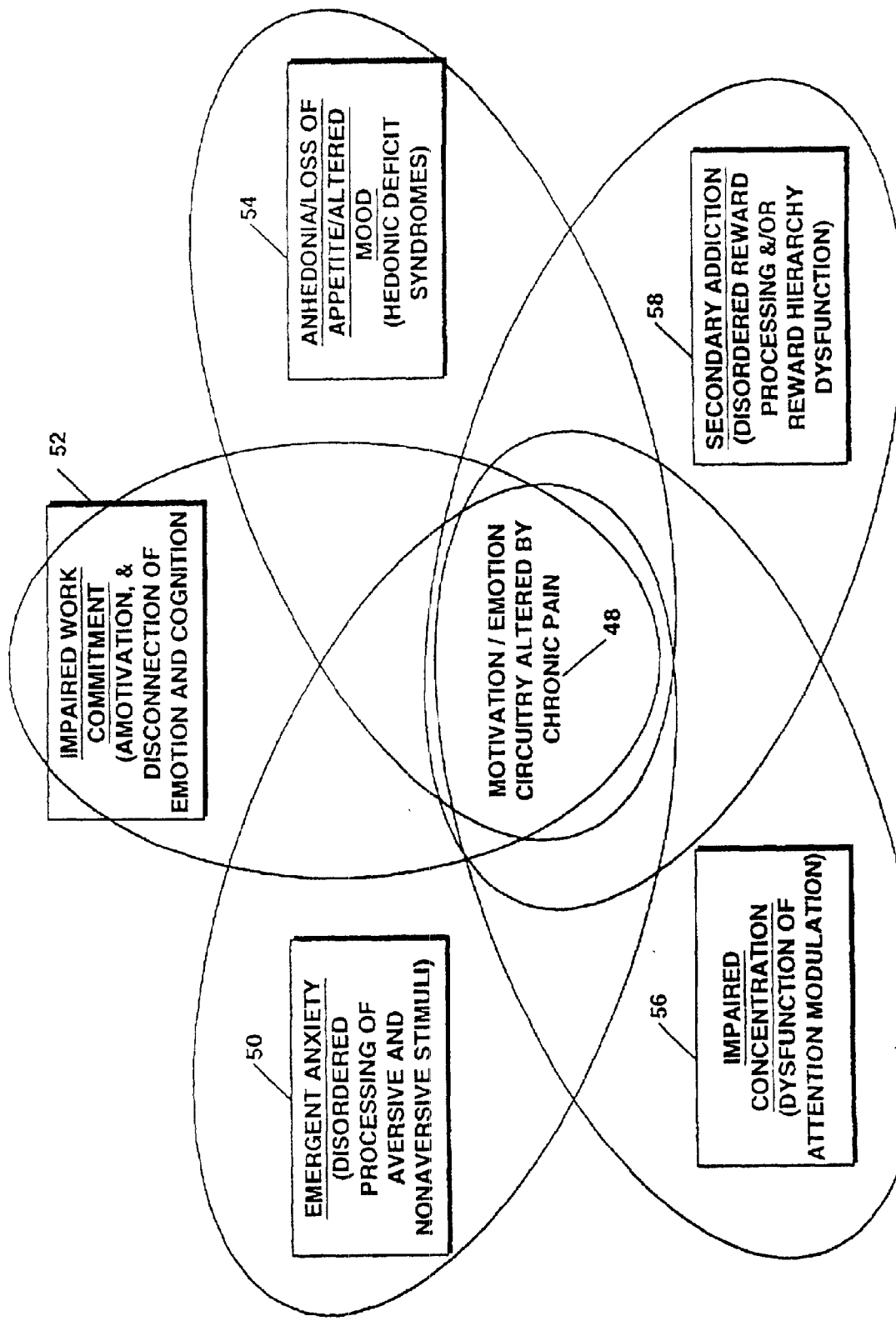
FIG. 2B is a schema detailing functional illnesses that can be the sequelae of chronic pain.

Referring now to FIG. 2B, a chart or schema 46 illustrates the relationship between circuitry of motivation altered by chronic pain 48 and a plurality of different behavioral states 50–58. Reference lines 62–70 indicate that relationships exist between each of the behavioral states 50–58 and the circuitry of motivation and emotion 48. It should be understood that pain is not traditionally considered a psychiatric disorder. Rather, pain is considered to have a number of functional sequelae. Thus, FIG. 2B is a schema detailing possible functional sequelae of chronic pain. Long term behavioral manifestations of pain include a constellation of symptoms aside from pain intensity, which closely parallel symptoms related to disordered motivation and emotion function observed with psychiatric illness. Thus, a close similarity exists between FIGS. 2A and 2B.

Referring now to FIG. 2C a conventional schema 79 of motivational function illustrates that motivated behavior necessitates at least three fundamental operations 80, 82, 84. Operation 80 includes selection of short-term and long-term objectives focused on attaining rewarding outcomes while avoiding aversive outcomes, operation 82 involves processing of perceptual features regarding the rate, delay, incidence, intensity, (i.e., worth), amount, and category of these potential outcomes to plan behavior, and operation 84 includes the actual determination of physical plans involving musculature or organ function to obtain these outcomes.

A simplistic rendition of subsystems needed for pulling H (where H corresponds to information as conceived and defined by Shannon & Weaver which is hereby incorporated herein by reference in its entirety) from the environment regarding potential rewards and aversive outcomes might segregate a subsystem for modulation of attention to putative goal-object features, a subsystem for probability assessment, and a subsystem for valuation. In congruence with prospect theory, probability computations would be processed in parallel with computations assessing value to determine the reward outcome as shown in FIG. 2D.

FIG. 2D illustrates three phases: (a) an expectancy phase 86; (b) an evaluation of worth phase 88; and (c) an outcome phase 90. If one considers variables needed to determine worth, one fundamental variable is the "rareness" of the goal-object in the environment, while a second is the value of the goal-object to the organism for reducing an existing "deficit state". The former variable of "rareness" depends on a probability assessment for its computation, and thus is an important input to any function of worth evaluation.

The integration of perceptual features regarding the rate, delay, incidence, intensity, amount, and category of these potential outcomes as shown in block 82 can be represented as shown in blocks 92–98 of FIG. 2D. In block 86, modulation of attention to H refers to the increased attention a subject gives to the source of information "H." This increased attention leads to an evaluation of goal-object features for "valuation of H" as shown in block 94.

Figure 3:
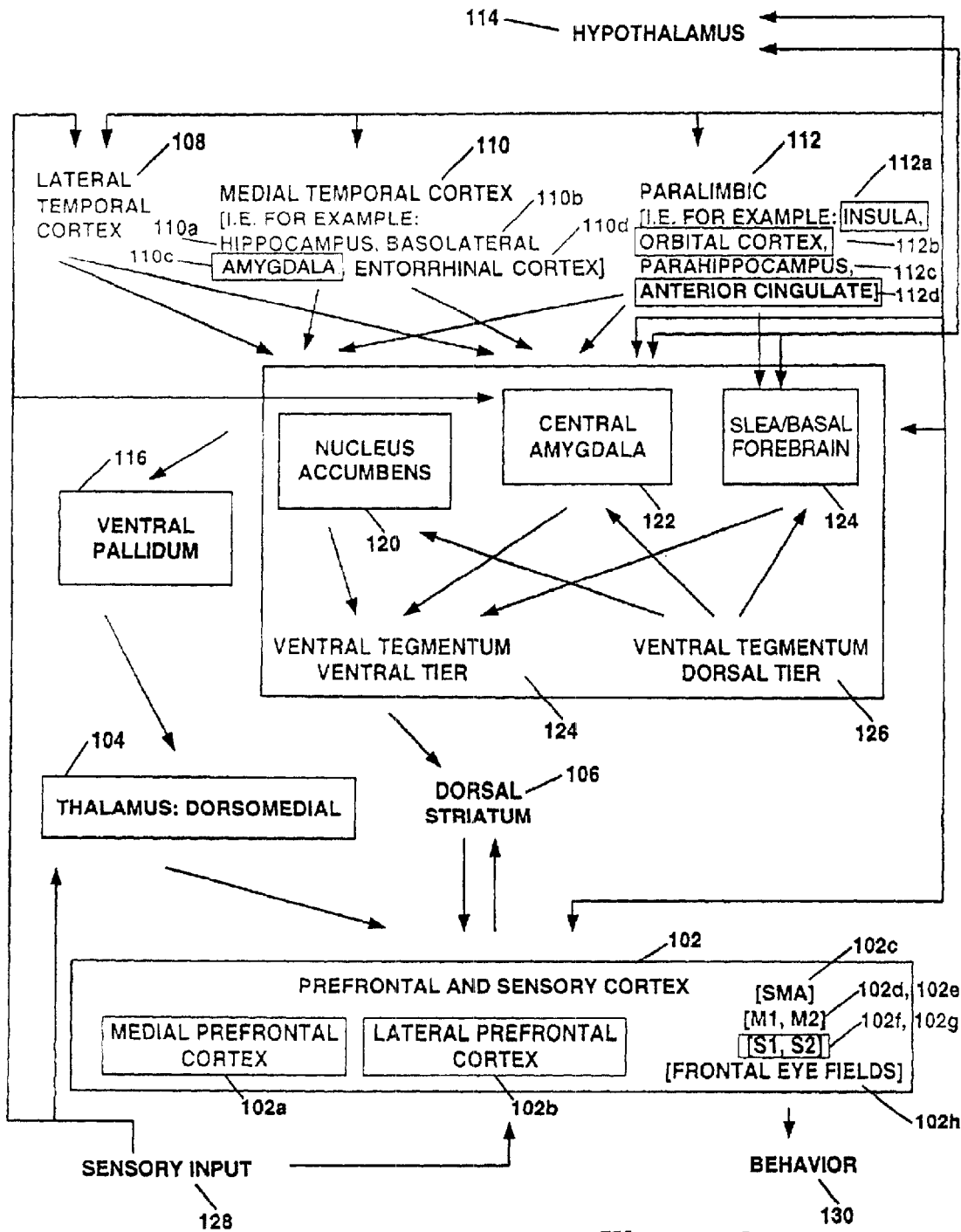
FIG. 3 is a block diagram of brain circuitry of reward and aversive function and illustrates brain anatomy of reward and aversive function that is implicated in motivated behavior.

FIG. 3 is a block diagram of brain circuitry 100 corresponding to brain circuitry of reward and aversive function (i.e. here collectively referred to as reward/aversion circuitry). That is, FIG. 3 shows the route by which the brain receives external/internal information and how that information propagates to various regions of the brain to produce motivated behavior. It should thus be appreciated that circuitry 100 illustrates brain regions of reward/aversive function that is implicated in motivated behavior.

The brain circuitry 100 includes a prefrontal and sensory cortex 102. The prefrontal cortex includes medial prefrontal cortex 102a and lateral prefrontal cortex 102b. The region 102 also includes the primary sensory and motor components 102c–102h. These components include the primary somatosensory cortex (S1) 102f, the secondary somatosensory cortex (S2) 102g, the primary motor cortices (M1) 102d, and secondary motor cortices (M2) 102e. Motor behavior involves regions such as M1 and M2, along with supplementary motor cortex (SMA) 102c. The frontal eye fields (102h) modulate motor aspects of eye control relating to directing the reception of visual signals from the environment to the brain.

Brain circuitry 100 also includes the thalamus region 104, the dorsal striatum region 106 and the lateral and medial temporal cortex regions 108, 110. The medial temporal cortex region 110 includes, for example, the hippocampus 110a, the basolateral amygdala 110b, and the entorhinal cortex 110. Also included as part of the brain circuitry 100 are paralimbic regions 112, which include, for example, the insula 112a, the orbital cortex 112b, the parahippocampus 112c and the anterior cingulate 112d. Current perspectives of reward circuitry also include the hypothalamus 114, the ventral pallidum 116 and a plurality of regions collectively designated 118.

The regions collectively designated 118 comprises the nucleus accumbums (NAc) 120, the central amygdala 122, the sublenticular extended amygdala of the basal forebrain SLEA/basal forebrain or SLEA/BF) 124, the ventral tegmentum (ventral tier) 126 and the ventral tegmentum (dorsal tier) 126.

The regions 118 collectively represent a number of regions having significant involvement in motivational and emotional processing. It should be appreciated that other components such as the basolateral amygdala 110c are also important but not included in the regions designated by reference number 118. Other regions that are further important to this type of processing include the hypothalamus (114), the orbitofrontal cortex (112b), the insula (112a) and the anterior cingulate cortex (112d). Further regions are also important but listed separately such as the ventral pallidum (116), the thalamus (104), the dorsal striatum (106), the hippocampus (110a), the medial prefrontal cortex (102a), and the lateral prefrontal cortex (102b). Not listed in this figure but also involved in processing sensory information for its emotional implications is the cerebellum.

The functional contribution of each of these major regions are discussed below. It should be noted that what follows is a gross simplification and does not convey the complexity nor the diversity of the functions that these regions have been implicated with and may in the future be connected to. Further note that there is currently a debate regarding the modular vs. non-modular function of these brain regions, i.e., can a specific function be attributed to each region in isolation. Accordingly what is listed below is information which provides one of ordinary skill in the art with the understanding that this function may be mediated by the connection of this region with many other regions (i.e., the function mediated by a distributed set of regions, of which the identified region is a fundamental component).

As a brain region the NAc 120 has previously been implicated in the processing of rewarding/addicting stimuli, and is thought to have a number of functions with regard to probability assessments and reward evaluation. It has also has been implicated in the moment by moment modulation of behavior (e.g., initiation of behavior). Signals measured from the NAc are shown and described below in conjunction with FIGS. 3A–3D.

The SLEA/BF has been implicated in reward evaluation, based on its likely role in brain stimulation reward effects. It is thought to be important for estimating the intensity of a reward value. It and other sections of the basal forebrain appear to be important for the processing of emotional stimuli in general, and it has been implicated in drug addiction.

Like the NAc, the amygdala has been implicated in both processing of emotional information along with processing of pain and analgesia information. The amygdala has been implicated in both the orienting to and the memory of motivationally salient stimuli across the entire spectrum from aversion to reward. It may be important for the processing of signals with social salience in real time. In this context it is often referred to with regard to fear. A number of its anatomical connections to primary sensory cortices, suggest that it is important for the modulation of attention to motivationally salient stimuli.

With respect to the VT/PAG, doparminnergic projections are present from the VT to the SLEA, the orbitofrontal cortex, the amygdala, and the NAc. Indeed dopaminergic projections go to most subcortical and prefrontal sites. In FIG. 3, the fundamental importance of the VT/PAG projection (124, 126) is focussed on the NAc (120), central Amygdala (122), and SLEA/BF (124), though it also projects to regions 110, 112, 116, 102a and 102b. The VT has been implicated in reward prediction processes, motor functions and a number of learning processes around motivational events in general. The PAG has also been impli-cated as a modulator of pain stimuli, for example, and may therefore be a region that signals early information on rewarding or aversive stimuli.

The GOb component of the prefrontal cortex has been implicated in a number of cognitive, memory, and planning functions around emotional stimuli or regarding rewarding or aversive outcomes in animal and human studies. This section of the prefrontal cortex has also been implicated in modulating pain. It has afferent and efferent connections with a number of subcortical structures (118). The GOb is involved in a number of different reward processes including those of expectancy determination and reward valuation. Patients with lesions in this region tend to have impulse control problems.

The hypothalamus (114) is involved in the monitoring and maintenance of homeostatic systems (e.g., endocrine control, satiety, thermoregulation, thirst monitoring, reproductive control, and pain processing). It also has been both implicated in the evaluation of the relevance for rewarding and aversive stimuli in order to maintain homeostatic equilibrium. The hypothalamus is highly important for meeting the objectives which optimize fitness over time and meet the requirements necessary for survival.

The cingulate cortex (112d) has been interpreted to be involved in attention and planning, the processing of pain unpleasantness, the processing of reward events and emotions in general, and the evaluation of emotional conflict. The cingulate cortex is an extensive region of brain cortex and appears to have emotional and cognitive subdivisions, to name a few.

The insula (112a) has been implicated in number of functions including the processing of emotional stimuli, the processing of somatosensory functions (e.g., pain), and the processing of visceral function.

The thalamus (104) is composed of a number of subnuclei which have been implicated in a diverse range or functions. Fundamental among these functions appears to be that of being an informational relay of sensory and other information between the external and internal environment. It has also been directly implicated in both rewarding and aversive processes, and damage to the structure may result in dysfunction such as chronic pain.

The hippocampus (110a) has been extensively implicated in functions for encoding and retrieval of information. Lesions to this structure lead to severe impairment in the ability to form new memories. Motivated behavior is heavily dependent on such memories: for instance, how a particular behavior in the past led to obtaining a goal object which would reduce a particular deficit state such as thirst.

The ventral palladium (116) is one of the primary output sources of the NAc and has a number of projection sites including the dorsomedial nucleus of the thalamus (109). Via this connection, it is one of the major relays between the NAc and the rest of the brain, in particular prefrontal cortical regions (102). It has been strongly implicated in reward functions and is a site thought to be important for the development of addiction.

The medial prefrontal cortex (102a) of the brain has been strongly implicated in reward functions and has been found to be one of the few brain sites into which cocaine self-administration can be initiated in animals.

In response to reward and aversion situations, certain regions of the brain circuitry 100 play a role in processing reward/aversive information to plan behavioral responses as discussed above. These regions are designated reward/aversion regions of the brain. The activation of such reward/ aversion regions can be observed during positive and negative reinforcement using neuroimaging technology. These reward/aversion regions produce specific functional contributions to motivated behavior. For example, contributions made by regions such as the include assessment of probability (i.e. expectancy).

Central to performing valuation, probability assessment, and other information processing tasks needed for planning behavior in response to reward and aversion situations are a number of core brain regions including the nucleus accumbens (NAc) 120, the sublenticular extended amygdala of the basal forebrain (SLEA/BF) 124, amygdala (multiple nuclei) 110c, 122, the ventral tegmentum/periaqueductal gray (VT/PAG) 124, 126, the hypothalamus 114 and the orbirtal gyrus (GOb). The GOb is designated as the orbital cortex 112b in FIG. 3. Also important to reward and aversion information processing are regions such as the insula 112a, anterior cingulate 112d, thalamus 104, ventral pallidum 116, medial prefrontal cortex 102a, and cerebellum (not shown in FIG. 3). The cerebellum is associated with integrating motor and autonomic behavior. It appears to have specific roles in reward and emotion, including the detection of errors in information processing or the implementations of motor behaviors.

As shown on FIG. 3, when a subject receives or senses an input 128, the sensory input is generally processed by multiple components of the brain circuitry simultaneously. The arrows in FIG. 3 indicate known afferent and/or efferent projections between those regions. While FIG. 3 provides a simplistic overview of the connections along which information processing occurs, it is important to note that processing may occur simultaneously between regions or sequentially across brain regions.

Each of these interactions cause the regions to produce specific functional contributions to motivated behavior which is manifested as indicated at 130.

Referring now to FIG. 3, in one experiment, core brain regions implicated in reward/aversive function were observed to activate in cocaine addicts after cocaine administration. In that experiment, the cocaine was administered after a brief abstinence from the drug in a randomized double-blind fashion relative to saline. Significant signal change was observed for the NAc 120 and SLEA 124 following cocaine with distinct time courses that correlated with subjective reports made by the subjects. Subjective reports of rush and craving from cocaine were correlated with distinct sets of brain regions activated. In particular, the NAc 120 and amygdala 110c, 122 were correlated with the motivational state of craving, while areas such as the SLEA/BF 118 and VT 124, 126 were correlated with the rush produced by cocaine.

The curves shown in FIGS. 3A–3C illustrate that activation of reward regions such as the NAc 20 can be observed after low dose morphine in healthy volunteers (as opposed to addicts). FIGS. 3A–3D illustrate signal changes in the NAc 120 observed in individuals over a period of time to saline vs. morphine. FIGS. 3A–3D thus demonstrate the power of neuroimaging to interrogate reward/aversion circuitry in individuals even with mild euphoria such as that produced by very low doses of morphine.

Turning now to FIGS. 3A and 3B, curves 132–142 correspond to time-course data (curves measured from the left NAc in five subjects for both morphine and saline infusions (FIGS. 3A, 3B respectively). Percent signal change in FIGS. 3A and 3B are normalized relative to each subjects pre-infusion baseline, but not detrended. The curves are plotted as percent signal change. The average signal change for the five subjects is shown as lines 136, 142, and the average infusion interval, given cardiac-gating of the acquisition begins at 300 seconds and ends at 780 seconds. The time-course data was sampled from each individual using a region of interest from the aggregate statistical map with each voxel localized in NAc meeting probability a threshold of $p<0.05$.

FIGS. 3A, 3B show that individual signals can be readily obtained in these small motivationally relevant regions. It also shows that there is a congruence of positive signal for a rewarding stimulus for this particular region.

Referring now to FIGS. 3C and 3D, individual time-course data after morphine and after saline is averaged separately for the right (curve 146—morphine: curve 148—saline) and left (curve 144—morphine: 150—saline) NAc. Error bars are included for the MRI data acquired as the 20' time-point, the 70' time-point, the 150' time-point, and the 250' time-point. Time is represented in seconds using a conversion of repetition time (TR)=6 RR intervals=6 seconds. These graphs show that there were bilateral NAc changes to this particular rewarding stimulus, which is not always the case as noted in the summary figure for multiple reward experiments. (Table II)

Figure 3F:
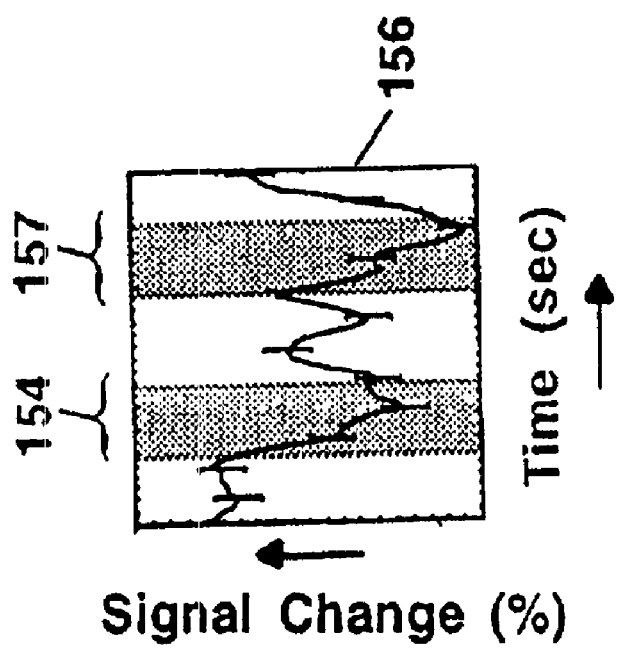
FIG. 3F is a plot of signal strength change in the right nucleus accumbens vs. time.
Figure 3E:
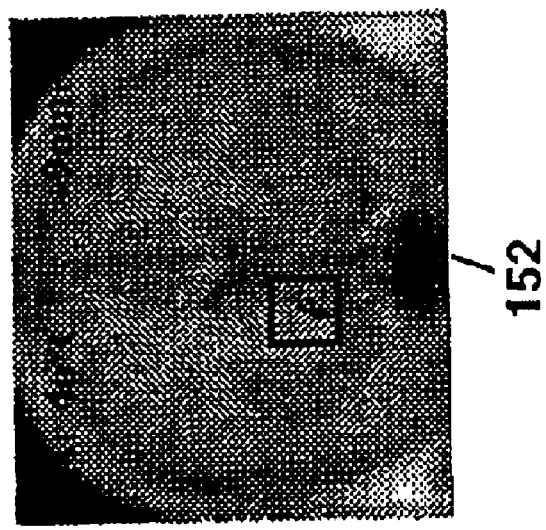
FIG. 3E, is a statistical activation map of significant signal change in the right nucleus accumbens dulling a painful stimulus.

Referring now to FIG. 3E, the statistical activation map for significant signal change in the right nucleus NAc (152), averaged for six subjects is shown. Reference numbers 154, 157 denote time interval during which a 46° C. stimulus is applied to a hand of a subject.

Referring now to FIG. 3F, curve 156 corresponds to the average time course (i.e., % signal change vs. time) of the activation shown in FIG. 3E. Note the correlation between the change in signal and the duration of the painful thermal stimuli (46° C.) shown as regions 154, 157. The time periods designated 154 and 157 correspond to periods in which painful thermal stimulus is applied to the subject. It should be noted that the signal goes down during these periods of time. After period 154 the signal 156 returns toward baseline during the inter-stimulus interval (i.e., between offset of 154 and onset of 157) and goes negative again during the second application of the thermal stimulus which takes place during time period 157. The decrease in signal during periods 154, 157 is highly significant because it shows that an aversive stimulus is negatively valenced (i.e. an aversive stimulus results in a signal change opposite to that of rewarding stimuli-e.g. cocaine, morphine monetary reward, beauty).

Figure 3G:
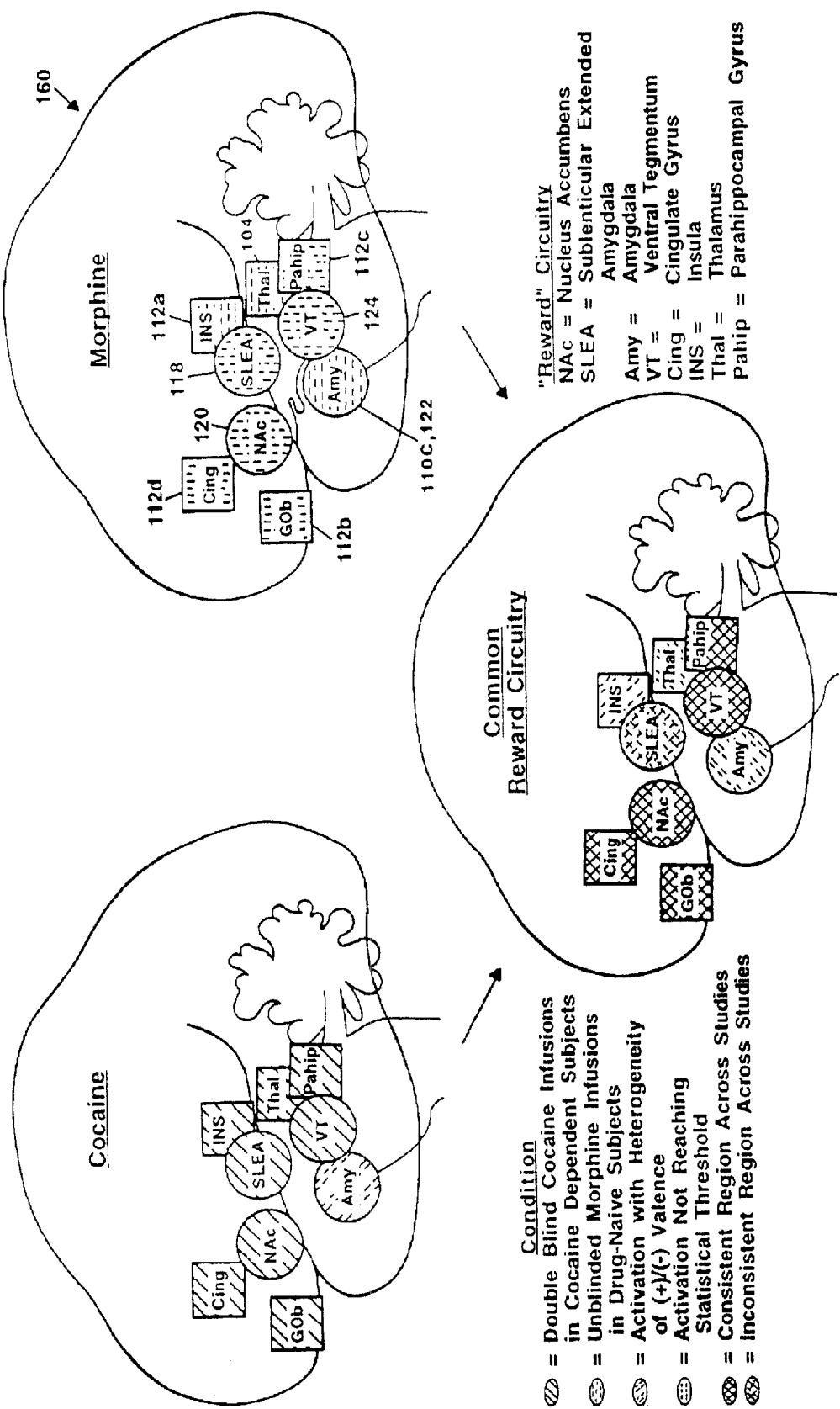
FIG. 3G is a block diagram of limbic and paralimbic brain regions observed in drug studies.

Referring now to FIG. 3G, reward and aversion regions activated for cocaine in addicts, and morphine in healthy volunteers, are juxtaposed to demonstrate the commonality of this circuitry. FIG. 3G thus corresponds to a summary schematic of limbic and paralimbic brain regions observed with double blind cocaine infusions in cocaine dependent subjects, and unblinded low-dose morphine infusions in drug-naive subjects.

Regions activated to a significant degree in the morphine and cocaine studies and not associated with heterogeneity of activation valence (i.e., positive vs. negative signal changes), are summarized in the brain schematic at the bottom of the image. Regions symbolized by a circle are sub-cortical regions traditionally associated with reward function in animal studies, while regions symbolized with squares are those associated in humans with emotion function in general. The commonality of activation across two distinct categories of drugs, in the NAc (120), SLEA (118), VT (124), and amygdala (110c 122) along with regions such as the cingulate cortex (112d) and orbital cortex—GOb (112b), suggests that a broad set of brain regions may be involved with generalized reward functions. Other regions included in the figure are the insula (112a), the thalamus (104) which is involved in sensory and motor integration and transmission and the parahippocampal gyrus (112c) which is involved in processing facial and location features. This composite figure strongly argues that there is a generalized circuit of reward/aversion that responds to divergently different categories of drug.

In another experiment, a game of chance (similar to gambling) was used. In this experiment, a wheel of fortune (i.e. a "spinner") having a spinning arrow on it was used. The arrow lands to signal the reception of a reward or "outcome" (money). This gives an example of the type of experiment that can be done for almost any demographic group. In such an experiment, expectancy (predicted chance of winning) and outcome (actual winning or dollars earned) processes are segregated in time.

In the experiment, subjects have the opportunity to lose money as well as win money since spinners are randomly presented in this experiment. The overall sequence of potential winnings and losses resembles a random walk process like that of a stock index. This follows the psychology of prospect theory, which is the basis of behavioral finance and decision making with regard to saving and spending money. An experiment was preformed to map the hemodynamic changes that anticipate and accompany monetary losses and gains under varying conditions of controlled expectation and counterfactual comparison. The paradigm involved subjects viewing stimuli projected onto a mirror within the bore of the magnet. The display consisted of either a fixation point or one of three disks ("spinners"). Each spinner was divided into 3 equal sectors. The "good" spinner could yield $10, $2.50, or $0.0 outcomes, the "bad" spinner could yield −$6.00, −$1.50, or $0.0 outcomes, and the "intermediate" spinner could yield $2.50, $0.0, or −$1.50.

Details of activation in different regions in terms of expectancies (prospects) and outcomes (winnings or losses) are shown in Table I below. As observed in Table I, multiple regions show differential patterns of signal change to good, bad and intermediate prospects. Each region of interest (ROI) in Table I below is defined a priori. A priori ROI's are anatomically defined prior to the experiment. Other regions not expected to activate can be determined to be significant if they meet conventional post-hoc statistical thresholds. A focus of activation is a group of pixels showing significant activation compared with baseline that are found in a region of gray matter of the brain.

Table I summarizes the anatomic location of regions of interest (ROIs), deviations of BOLD signals from baseline, and ANOVA results. "Coordinates" denotes the Talairach coordinates using the atlas of Talairach and Tournoux (1988) of the voxel with the strongest p-value at the center of each of the 16 ROIs. Coordinates are expressed in mm from the anterior commissure: R/L, right (+)/left (−); A/P, anterior (+)/posterior (−); S/I, superior (+)/inferior (−). "Change from Baseline" identifies ROIs in which the 95% confidence interval around the BOLD signal cleared zero. For the "Prospect" column, the spinner responsible for the deviation from zero is indicated by a "G", "I" or "B", for the good, intermediate and bad spinners, respectively. For the Outcomes column, numerals refer to the trial type as follows: 1, 2, and 3 represent the $10.00, $2.50, and $0.00 outcomes, respectively, on the good spinner. For the intermediate spinner, 4, 5, and 6 represent the $2.50, $0.00, and −$1.50 outcomes, respectively, and 7, 8, and 9 represent the $0.00, −$1.50, and −$6.00 outcomes, respectively, on the bad spinner. "Time points Clearing Baselines" lists how many time points reliably cleared the baseline for prospect and for outcome data. In both the "Prospects" and the "Outcomes" columns, (+) refers to positive deviations from zero, and (−) refers to negative deviations from zero. The. "ANOVA" column lists the ROIs for which significant main effects or interactions were found. ROIs with nonsignificant results are designated by a dash ("−") For the expectancy phase, ROIs with a significant main effect of spinner are indicated by "SP", and ROIs with a significant interaction of spinner and time point are indicated by "SP*TP". Similarly, ROIs with significant main effects of trial type during the outcome phase are designated by "BI", whereas ROIs with significant interaction of trial type and time point are indicated by "BI*TP".

TABLE I

| Anatomy | ROI# | Coordinates R/L | A/P | S/I | Change from Baseline Prospects | Outcomes | ANOVA Prospects | Outcomes |
|---|---|---|---|---|---|---|---|---|
| Frontal Lobe | | | | | | | | |
| GOb | 1 | −25 | 47 | −18 | B | 2, 8 | SP*TP | BI |
| GOb | 2 | 15 | 34 | −21 | G, I | 1 | — | — |
| GOb | 3 | −12 | 66 | −6 | — | — | — | — |
| GOb | 4 | 18 | 19 | −25 | — | 1, 9 | — | BI |
| GOb | 5 | 6 | 59 | −12 | G | 3 | — | BI |
| GOb | 6 | 25 | 59 | −18 | G | 2, 8 | — | BI*TP |
| GOb | 7 | −34 | 38 | −18 | B | 2 | — | — |
| GOb | 8 | −12 | 31 | −21 | G | 6 | — | BI |
| GOb | 9 | 28 | 44 | −12 | G, B | — | — | — |
| GOb | 10 | −25 | 13 | −9 | B | 2, 3, 7 | SP | BI, BI*TP |
| Temporal Lobe | | | | | | | | |

TABLE I-continued

| | | | | | Change from Baseline | | ANOVA | |
|---|---|---|---|---|---|---|---|---|
| Anatomy | ROI# | R/L | A/P | S/I | Prospects | Outcomes | Prospects | Outcomes |
| Medial | | | | | | | | |
| Amygdala | 11 | −18 | 3 | −15 | B | 5 | SP*TP | BI |
| Amygdala | 12 | 21 | −3 | −21 | — | 9 | — | BI |
| Subcortical Gray | | | | | | | | |
| NAc | 13 | 12 | 16 | −6 | G, I, B | 1–3, 6, 7, 9 | SP | BI, BI*TP |
| SLEA | 14 | 18 | 0 | −6 | G, I, B | 1–3, 6–9 | SP | BI |
| Hypothalamus | 15 | 9 | −3 | −6 | G, I, B | 3, 6, 9 | SP, SP*TP | BI |
| Brainstem | | | | | | | | |
| VT | 16 | 12 | −18 | −12 | G, I, B | 3 | — | BI |

It has also been shown that the clustering of regions involved in expectancy and outcome assessment in different hemispheres of the brain exists. As can be seen from the prospect column and coordinates columns, it is notable that there appears to be a right hemisphere predominance (note positive values in the R/L column), for deep brain structures (e.g., NAc, SLEA) with regard to positive stimuli, while there is a left hemisphere dominance for negative stimuli in regions such as the amygdala and GOb ROI numbers 1, 7, 10. Data such as this show that right or left brain activation of reward/aversion may be important for interpreting the signal changes.

As noted above, many brain regions showing expectancy effects also show outcome effects.

Figure 3H:
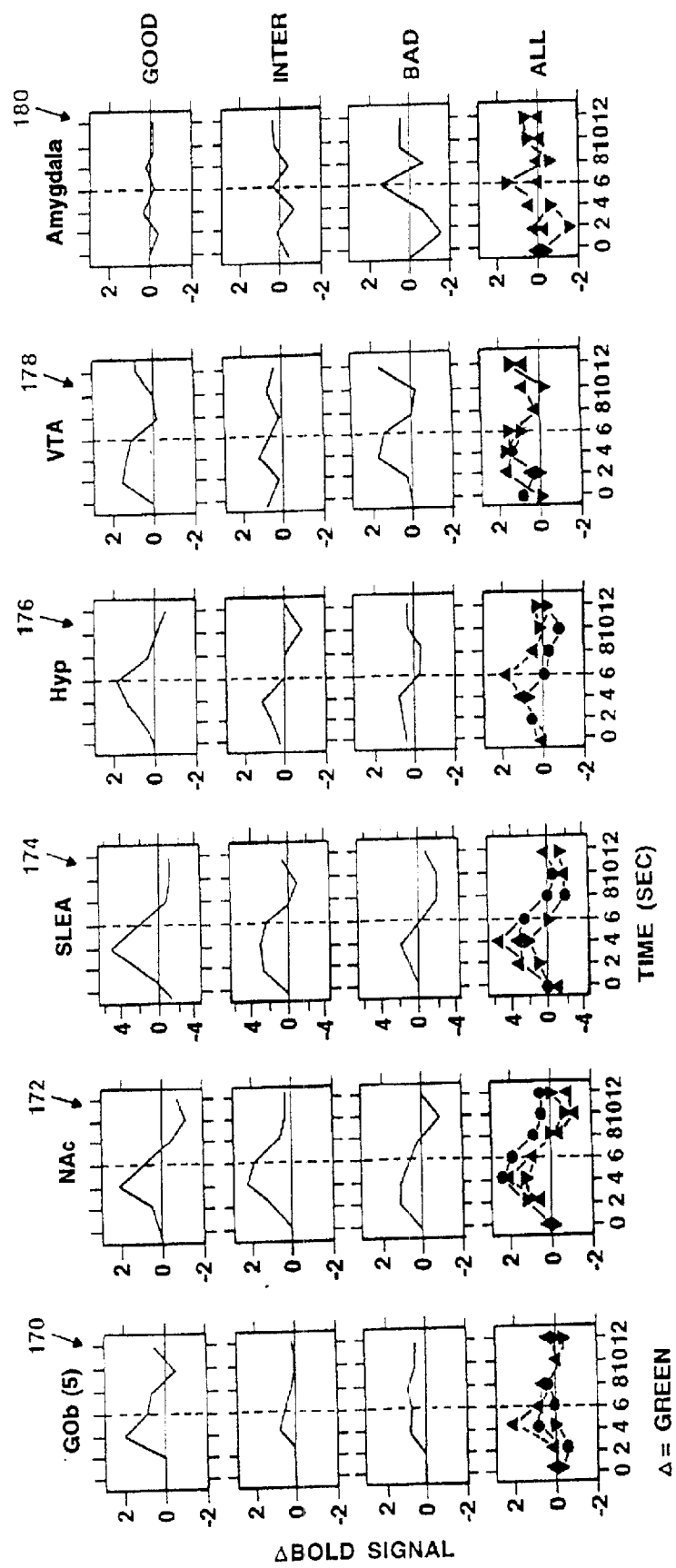
FIG. 3H, is a series of plots showing absolute fMRI signals reflecting expectancy responses for six regions of interest in reward regions vs. time.

Referring now to FIG. 3H, absolute fMRI signals are displayed for six regions of interest in reward/aversion regions. Signals were zeroed relative to an eight second pre-stimulus epoch. The time-courses for the good (▲), intermediate (●), and bad (▼) spinners are displayed. The dashed lines segregate the expectancy and outcome phases of the experiment. The bottom graphs illustrate the good, intermediate, and bad spinner time-courses together, using the same coding as in the columns of signals above them. In FIG. 3H, the first five columns show signals representing activity in the GOb(5) 170, NAc 172, SLEA 174, hypothalamus 176 ("Hyp" in the FIG. 3H), and VT 178, all of these regions show strong good spinner effects during the expectancy phase of the experiment. In the last column in FIG. 3H, the signal from the left amygdala 180 region shows minimal effects, during the good and intermediate spinners, and strong biphasic effects during the bad spinner. Namely, the bad spinner produces a signal that becomes negative and then positive during the time it is spinning. For all six regions, differential responses to discrete expectancy conditions are shown. The expectancy response of the NAc, SLEA hypothalamus, VT and GOb occurs in temporal link to the spinner being initially presented, & spinning. It reflects the assessment of contingent probabilities around potential gains and losses shown on the spinner. A discrete expectancy is one of good, intermediate, or bad outcomes. This is the first demonstration of controlled expectancy effects in humans and further shows that the waveforms in each of these regions were significantly different. This data provides evidence that probability functions are computed by distributed sets of reward regions.

Figure 3I:
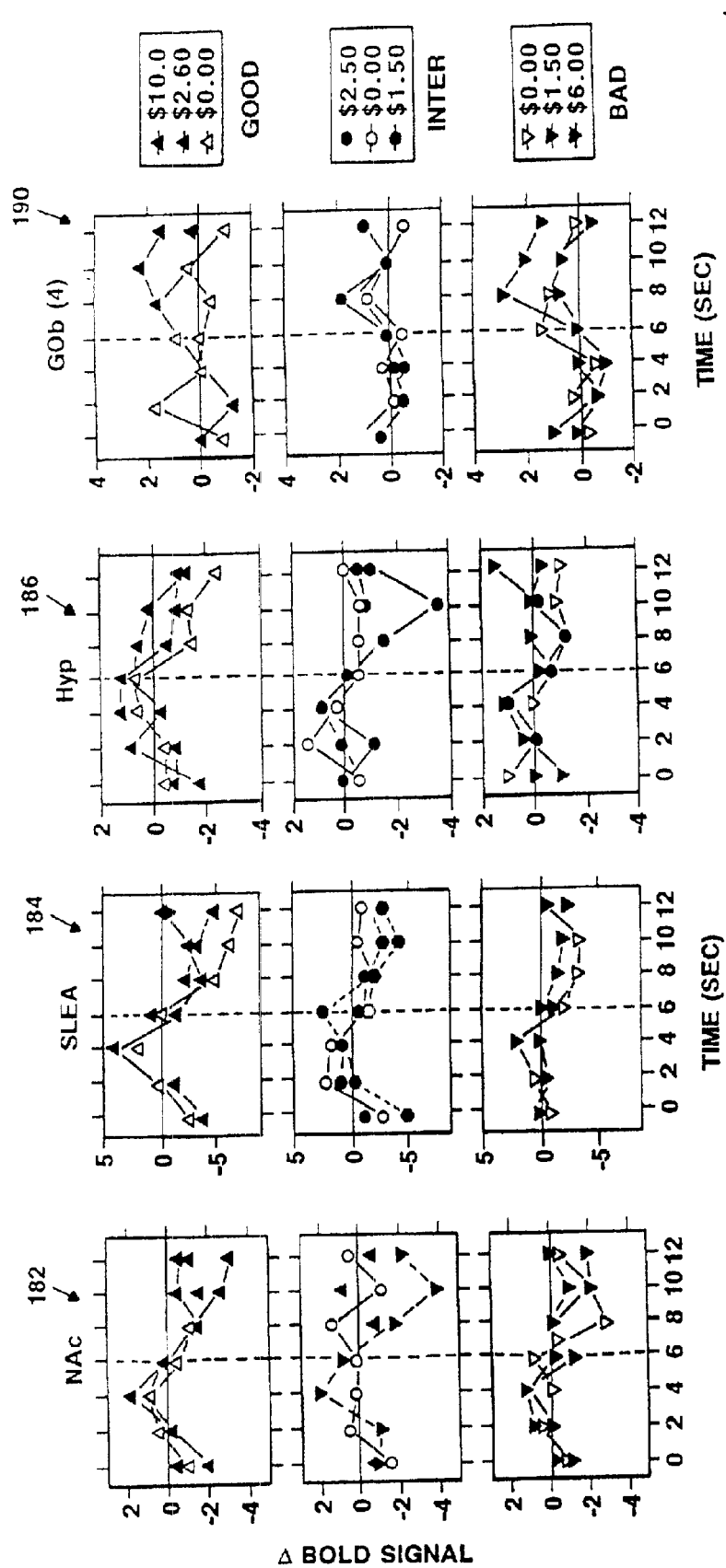
FIG. 3I, is a series of plots showing absolute fMRI signals for four regions of interest in reward regions vs. time for three different outcomes on each spinner.

Referring now to FIG. 3I, the robust time-courses for bin effects in four ROIs 182–190 are illustrated. Bins (monetary outcomes, for example $10, $2.50 and $0.00) on the good spinner are shown in the top row of graphs, while bins for the intermediate spinner are shown in the middle row, and bins for the bad spinner are shown in the bottom row. A bin effect corresponds to the response to each spinner landing on one of three possible outcomes. The eight seconds of data acquired before the outcome phase of the experiment are used to zero the data. The three columns of data from the NAc 182, SLEA 184, and Hyp 186 in are grouped to illustrate regions that show differential effects for predominant gains as outcomes in the context of good expectancy. It should be noted that these three ROIs 182, 184, 186 show differential effects for the outcomes on the good spinner and demonstrate strict ordering on the basis of outcome magnitude. That is, on the good spinner, outcomes of $0.00, $2.50 and $10.00 are possible, and discrete ordering of the results are observed depending on the outcome. Similar orderings are not observed for outcomes in the context of intermediate and bad expectancies. These orderings are salient for supporting the notion that a distributed set of human brain regions represents stimulus worth in a parametric fashion. The GOb 190 is presented to illustrate a very different profile of outcome responses. Namely, this ROI appears to respond to extremes, such as the $10.00 outcome in the context of good expectancy, and the −$6.00 outcome in the context of bad expectancy. Differential responses to discrete monetary outcomes in a number of reward regions demonstrate that magnitude differences in the valuation of rewarding stimuli can be distinguished. This shows that reward functions are not just "on" "off" phenomena but produce a gradation of response across the continuum of reinforcement (i.e., between reward and aversion). These data indicate that the brain can discriminate nuances in value across the continuum between reward and punishment, and between pleasure and pain. Such observations show that a mechanism exists for determining what an organism values, and the relationship of this valuation to valuation of other objects, events, or internal states.

FIGS. 3J–3O illustrate early and late activation in different brain regions.

Referring now to FIG. 3J, curve 192 corresponds to a time course of the signal (signal change vs. time) for activation in the SLEA following a 46° C. stimulus. It should be noted that there is a large initial change in the signal 192 during the first epoch 193 of the thermal stimulus and not during subsequent thermal epochs 194, 196, 200. Curve 192 illustrates that early and profound activation in one area of the reward/aversion (SLEA) compared with late activation illustrated by curve 211 (FIG. 3O) in SI (somatosensory cortex).

Referring now to FIGS. 3K and 3L, these figures shows activation in the SLEA during the early 202 phase and no activation in the region during the late phase 204 of a 46° C. stimulus. Other activations in the figure represent known regions including the right and left insula (112—in FIG. 3) and the cingulate gyrus (112d—in FIG. 3).

Referring now to FIGS. 3M and 3N, the figures show relatively little activation in the primary somatosensory cortex (S1) 206 and designated as 102f in FIG. 3 during the early phase of the stimulus while there is significant activation of the S1 region 208 during the late phase of the stimulus. Other areas of activation include the insula (112—in FIG. 3).

Referring now to FIG. 3O, curve 211 corresponding to a time course of the signal in the primary somatosensory cortex 208 (and designated as 102F in FIG. 3) extends across multiple time periods or epochs 212–215. It should be noted that activation exists within region 208 in each of the time periods 212–215 during which the thermal stimulus is applied.

It should be appreciated that FIGS. 3J–3O show why regions such as the SLEA, which has been heavily implicated in goal-object valuation, (i.e., how rewarding or aversive is a stimulus) respond to an aversive stimulus ahead of systems involved with primary somatosensory perception. The SLEA time course is orthogonal to typical time-courses of subjective ratings of pain. Namely, it's signal returns to baseline at the time subjects are rating maximal pain intensity from a pulsalite thermal stimulus. The SLEA response this occurs before subjects make conscious ratings that they are feeling pain. This is an example of how neuroimaging can be used to potentially differentiate conscious from non-conscious processes with relevance to motivation.

It should also be appreciated that distinct patterns of reward/aversive circuitry function can be observed after presentation of different valences of stimuli (particularly with regard to the left amygdala) (i.e., fearful vs. happy or neutral faces) to different subjects. It is important to note, for example, that both happy and fearful signal habituates rapidly over the course of an experiment. This indicates that the brain adapts to novel emotional information quickly and that the techniques of the present invention can be used to observe this function.

It has also been observed that right amygdala activation occurs after a different category of aversive stimulus (i.e., sad faces). Thus, it should be appreciated that components of the reward/aversion may respond in different degrees to various motivational and emotional stimuli. It should also be appreciated that demographic differences in subjects can lead to different activation in different groups of subjects (e.g. male vs. female) to the same stimulus. For example, NAc and amygdala activation to fearful faces are different in groups of men and women.

Demographic differences in subjects can lead to different activation in different groups of subjects (e.g. male vs. female) to the same stimulus. For example, distinct differences in activation of reward/aversion regions between men and women, particularly for the mid-luteal phase of the menstrual cycle have been found.

Also, drug expectancy effects can be observed prior to the infusion of cocaine vs. saline. For example, NAc activation can be observed prior to and shortly after cocaine infusions, but before the onset of any pharmacological effects. These effects result from probability assessments regarding the potential of receiving a drug reward (i.e. a previously experienced reward). This demonstrates that subsystems of motivational circuitry function can be interrogated in isolation of other subsystems. In addition, subjects did not intend to signal their expectancy of drug, yet the neuroimaging technology recorded it.

Table II provides a summary of activation across multiple studies using different categories of reward/aversion. Table II shows that a common circuitry processes reward information, regardless of the category of the reward stimulus, whether drug, money or social stimulus (e.g. cocaine, morphine, monetary reward beautiful faces). Regions designated x in the Table II are activated. The observation that this is a generalized circuitry means that any type of object can be assessed regarding its rewarding/aversive properties to see how it falls along the continuum of reward and aversion (see FIGS. 3H, 3I regarding evaluating how it falls along the continuum of reward). Of further importance, the areas of brain activation that are common across these categories of reward were also observed to be activated during the perception of an aversive stimulus (see FIGS. 3E, 3F, and 3H, 3I). This commonality does not imply that all these regions work in the same way for rewarding and aversive stimuli (i.e. not all regions are activated at the same time—they are all activated differentially). For example, negatively valenced signal is observed in the NAc to a painful stimulus, while positively valenced signal is observed in the NAc for a drug reward such as morphine. Other regions may provide different levels of activation or different timing with respect to activation depending on the valence of the stimulus along the reward-aversion continuum.

Table II is divided into two main sections, one on expectancy, and one regarding reward/aversion outcomes. The left section on expectancy shows that across two studies with monetary reward and cocaine reward, expectancy effects lead to activation in a number of common areas, namely the GOb and bilateral NAc. These effects are different than the outcome effects in terms of signal intensity and waveform. Across a number of experiments-two experiments with cocaine infusions, one experiment with morphine, one experiment with monetary reward, and one experiment with a social reward (beautiful faces)-common foci of activation were observed in the right GOb, NAc, SLEA, and potentially the VT. The X's in the columns of Table II are superscripted to indicate more than one foci of activation in that region (i.e., $X^2$=2 foci of activation, $X^3$–3 foci of activation). Brackets around an X indicate that the statistical significance of the findings were just subthreshold for the experiment in question. It should be noted that there are two columns for the cocaine experiments, representing two completely separate cocaine experiments. The two columns for the beauty study represent positive vs. aversive outcomes. In this study it was found that young men looking at beautiful male faces, devalued the images, indicating they were non-rewarding, while valuing the beautiful female faces, indicating that they, in contrast, were rewarding. It should be noted that the beauty experiment is not the only one with aversive and rewarding outcomes. For example a monetary reward experiment discussed below also had very explicit rewards vs. losses. The strongest results regarding aversive outcomes, though, are the pain studies, which show activation in the same right GOb, NAc, and SLEA regions that are common across category of reward.

TABLE II

| Expectancy Region | | Monetary Reward | Cocaine Expectancy | Outcomes Region | | Cocaine (1) | Cocaine (2) | Morphine | Monetary Reward | Beauty (+) | Beauty (-) |
|---|---|---|---|---|---|---|---|---|---|---|---|
| Gob | R | $X^2$ | $X^2$ | Gob | R | X | X | (X) | $X^3$ | $(X^2)$ | |
|  | L | X | X |  | L | X | X |  | $X^3$ |  | |
| NAC | R | X | X | NAc | R | X | X | $X^3$ | X | X | (X) |
|  | L | X |  |  | L | X |  | X |  |  | X |
| SLEA | R |  |  | SLEA | R | (X) | X | $X^2$ | X | (X) | |
|  | L |  |  |  | L | X |  |  |  |  | X |
| Amygdala | R |  |  | Amygdala | R | (X) | X |  | X |  | |
|  | L | X |  |  | L | X |  |  | X |  | (X) |
| VT | R |  |  | VT | R | X | X |  | X |  | |
|  | L |  |  |  | L | X | X | X |  | (X) | |

Figure 4:
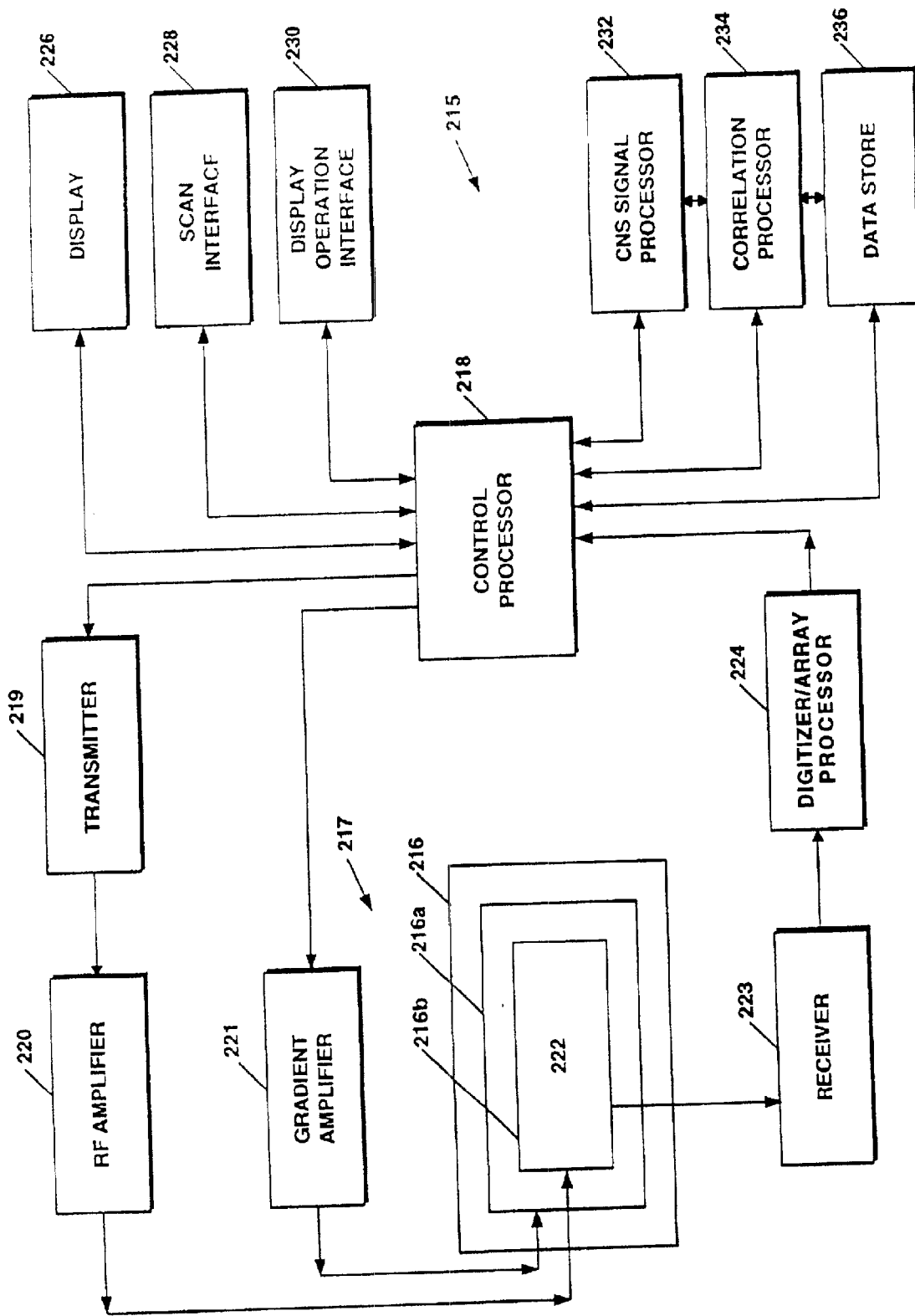
FIG. 4 is a block diagram of a noninvasive measurement apparatus and system for measuring indices of brain activity during motivational and emotional function.

Referring now to FIG. 4, a noninvasive measurement apparatus and system for measuring indices of brain activity during motivational and emotional function is shown. In this particular example a magnetic resonance imaging (MRI) system 216 that may be programmed to non-invasively aid in the determination of indices of brain activity during motivational and emotional function in accordance with the present invention is shown. Its should be appreciated however that other techniques including but not limited to fMRI, PET, OI, SPECT, CT, fCT, MRS, MEG and EEG may also be used to non-invasively measure indices of brain activity during motivational and emotional function.

MRI system 215 includes a magnet 216 having gradient coils 216a and RF coils 216b disposed thereabout in a particular manner to provide a magnet system 217. In response to control signals provided from a controller processor 218, a transmitter 219 provides a signal to the RF coil 216b through an RF power amplifier 220. A gradient amplifier 221 provides a current to the gradient coils 216a also in response to signals provided by the control processor 218.

For generating a uniform, steady magnetic field required for MRI, the magnet system 217 may be provided having a resistance or superconducting coils and which are driven by a generator. The magnetic fields are generated in an examination or scanning space or region 222 in which the object to be examined is disposed. For example, if the object is a person or patient to be examined, the person or portion of the person to be examined is disposed in the region 222.

The transmitter/amplifier combination 219, 220 drives the coil 216b. After activation of the transmitter coil 216b, spin resonance signals are generated in the object situated in the examination space 222, which signals are detected and are collected by a receiver 223. Depending upon the measuring technique to be executed, the same coil can be used as the transmitter coil and the receiver coil or use can be made of separate coils for transmission and reception. The detected resonance signals are sampled, digitized in a Digitzer/Aray proceser 224. Digitizer/Array processor 224 converts the analog signals to a stream of digital bits which represent the measured data and provides the bit stream to the control processor 218.

A display 226 coupled to the control processor 218 is provided for the display of the reconstructed image. The display 226 may be provided for example as a monitor, a terminal, such as a CRT or flat panel display.

A user provides scan and display operation commands and parameters to the control processor 218 through a scan interface 228 and a display operation interface 230 each of which provide means for a user to interface with and control the operating parameters of the MRI system 215 in a manner well known to those of ordinary skill in the art.

The control processor 218 also has coupled thereto a CNS signal processor 232, a correlation processor 234 and a data store 236. It should be appreciated that each of the components depicted in FIG. 4, except for the CNS signal processor 232 and the correlation processor 234 are standard equipment in commercially available magnetic resonance imaging systems.

It should also be appreciated that the MRI system must be capable of acquiring the data which can be used by CNS signal processor 232 and the correlation processor 234. In some embodiments, the CNS signal processor 232 and the correlation processor 234 may be provided as a general purpose processors or computers programmed in accordance with the techniques described herein to determine indices of brain activity during motivational and emotional function. For example, in some applications it may be desirable to provide a single processor or computer which is appropriately programmed to perform the functions of control processor 216, the CNS signal processor 232 and the correlation processor 234. In other embodiments, the CNS signal processor 232 and the correlation processor 234 may be provided as specially designed processors (e.g. digital signal processors) or other specially designed circuits. In any event the CNS signal processor 232 and the correlation processor 234 are unique in that they are programmed or otherwise designed to determine indices of brain activity during motivational and emotional function in accordance with the present invention as described herein.

The CNS signal processor 232 and the correlation processor 234 cooperate to determine indices of brain activity during motivational and emotional function. One particular technique for determining indices of brain activity during motivational and emotional function is described below in conjunction with FIGS. 5A–5C. Suffice it here to say that once CNS signals are obtained (e.g. via a non-invasive technique including but not limited to MRI, fMRI, PET, etc. . . . ), the signals are localized to examine the function in a particular region of the brain. The particular manner in which such the signals are localized are dependent upon a variety of factors including but not limited to the technique or techniques (including equipment) used to extract the signals.

Once signals are extracted, the correlation processor 234 correlates empirical data with the measured signals. The correlation processor 234 then interprets the results of the correlation to a specific application. The CNS signal processor 232 and the correlation processor 234 perform many of the functions described in phases 502–509 below in conjunction with FIGS. 5A–5C which describe the Motivational/Emotional Mapping Process (MEMP) classification.

It should be appreciated that although processors 232, 234 are here shown as separate and distinct processors, in practice the functions described herein may involve the use of both processors 232, 234. Moreover, in practice all functions described herein can be performed by different processors (e.g. processors 218, 232, 234) or may be performed by a single processor or by more than three processors. Thus, processors 232, 234 may cooperate as interdigitated processors. Processor 232 may be involved in performing all or portions of steps 502–507 (FIG. 5A) while processor 234 may be involved in performing all or portions of steps 502, 503, 508a, 508b.

Figure 5A:
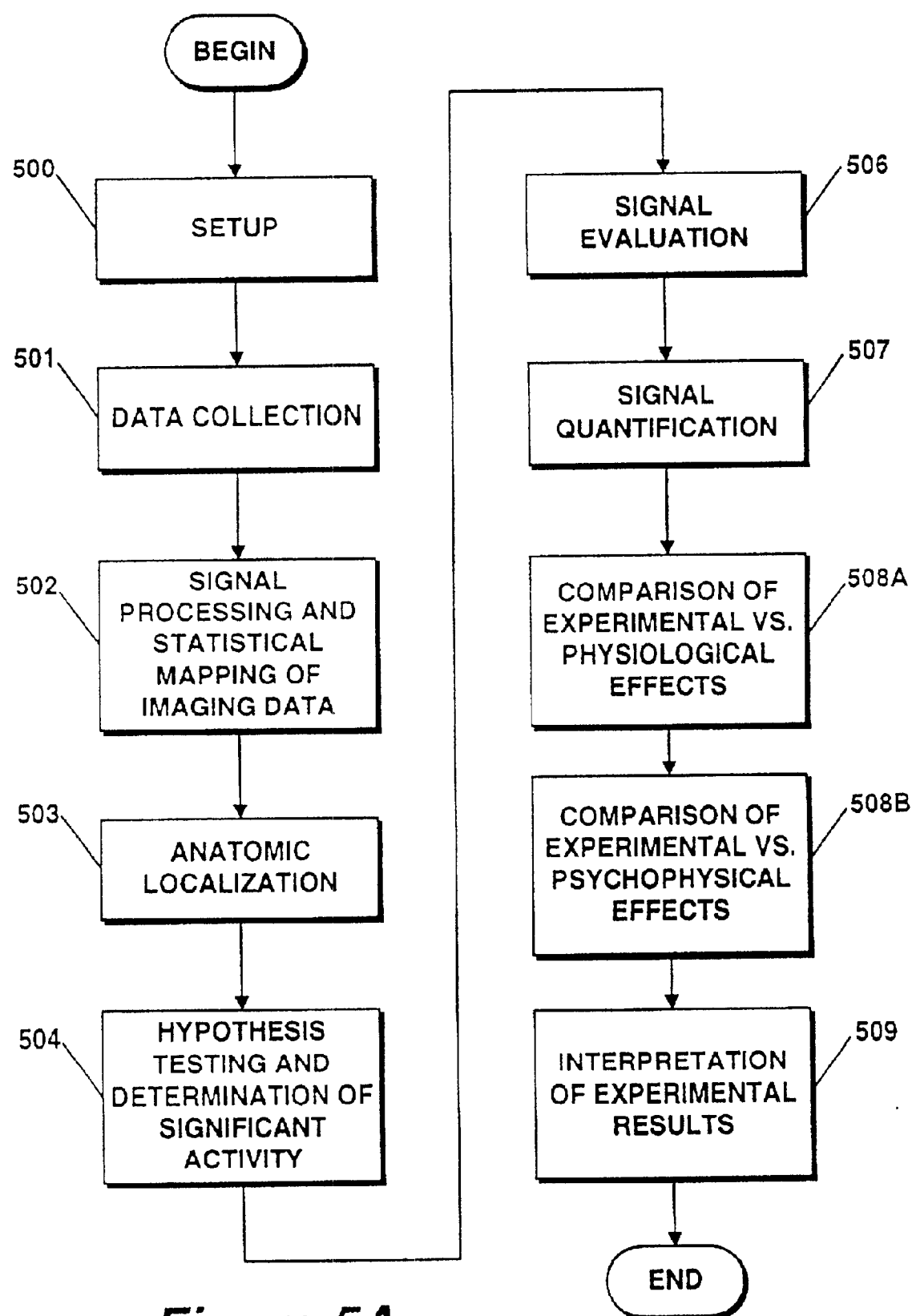
FIG. 5A is a flow diagram illustrating the general phases of a motivational/emotional mapping process (MEMP) According to the present invention.
Figure 5B:
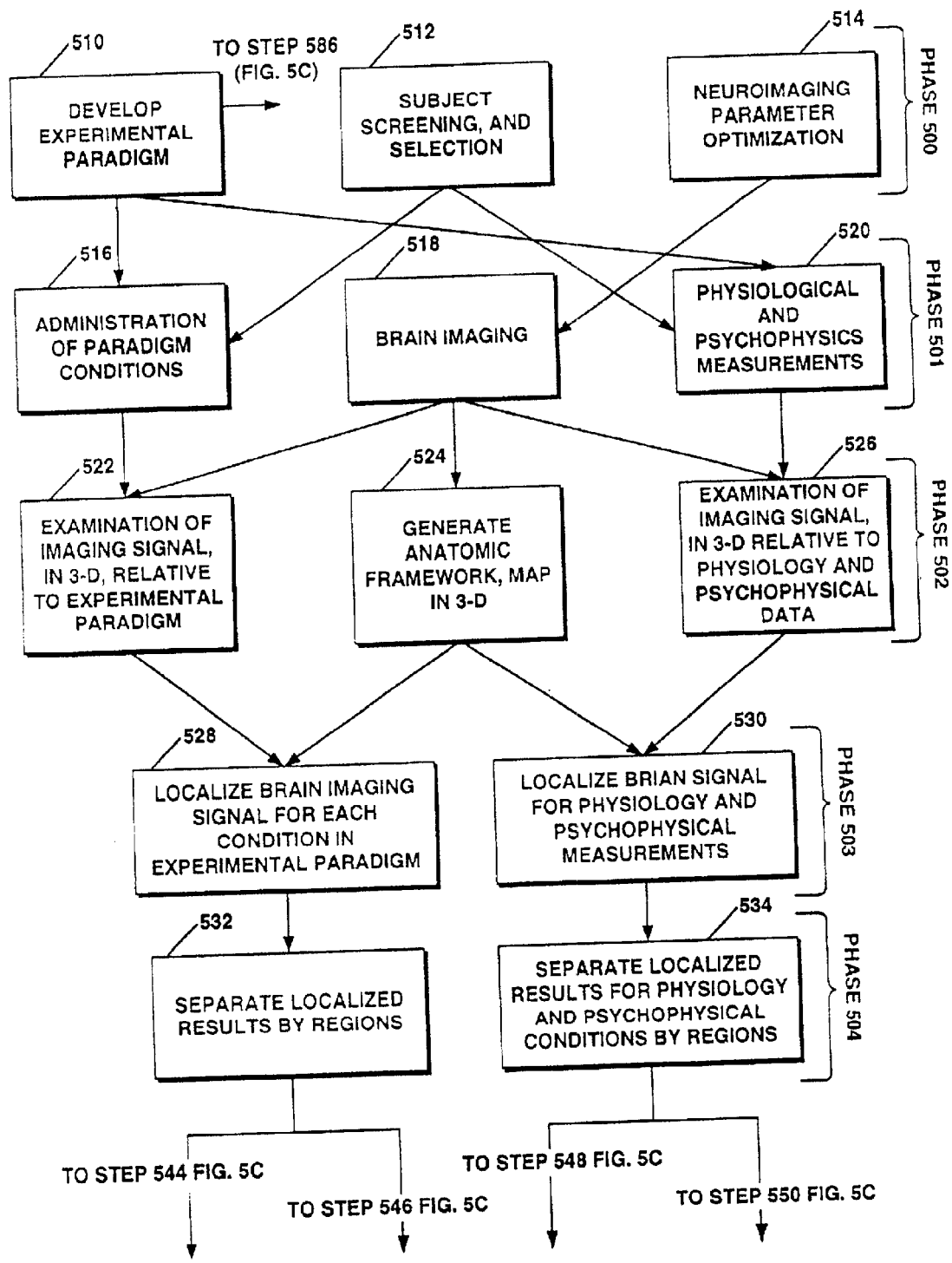
FIGS. 5B–5D are a series of flow diagrams illustrating a MEMP schema for mapping motivational/emotional response.

The remaining components of FIG. 4 perform the functions described in phase 501 of FIG. 5A and step 518 of FIG. 5B.

Referring now to FIG. 5A, general phases used in a Motivational/Emotion Mapping Process (MEMP) are illustrated. This process can be partially implemented using a CNS measurement system, such as system 215 described above in conjunction with FIG. 4. In a setup phase 500, the experimental paradigm is developed, subjects are screened and selected, and neuroimaging parameters are optimized. The experimental paradigms are developed by considering a variety of factors including but not limited to part experiments, knowledge of a particular characteristic of participants, knowledge of what region in being interrogated.

In phase 501, brain imaging data is collected along with physiological and psychophysical data. Preferably a non-invasive measurement system such as the MRI system 215 of FIG. 4 is used to image the brain. It should be appreciated, however, that there are several other techniques known in the art to obtain brain imaging with sufficient resolution (approximately 5×5×5 mm) for the MEMP.

In a signal processing and statistical mapping of imaging data phase 502, signal processing involves the normalization of data across subjects and experimental conditions, and transformation of data into a uniform space for averaging, or anatomically precise sampling of signals. Standard signal processing techniques of fMRI include, but are not limited to motion correction, signal intensity scaling, detrending, spatial filtering, temporal filtering, and morphing of the functional imaging data into a uniform space such as that of Talairach and Tournoux. Statistical mapping involves evaluating fMRI 3D data across time for significant changes relating to experimental conditions or any other variables such as subject physiology or psychophysical responses. Although here four dimensions (f MRI 3D and time) are used, those of ordinary skill in the art will appreciate that N dimensions can also be used. Statistical evaluation involves some degree of location and scale estimation along with techniques for computing general effects and pairwise differences between experimental conditions. The type and sequence of signal processing and statistical mapping of imaging data may vary across the technique of imaging used (including but not limited to MRI, fMRI, PET, EEG, MEG, etc.).

In an anatomic localization phase 503, anatomic templates for precise localization of fMRI signal changes are prepared. Anatomic scans, acquired either at the time of functional neuroimaging with the experiments or at another time, are transformed into the same uniform space as the functional brain data. For example, this may involve a Talairach transformation (i.e., brain anatomy from individuals is normalized into a standardized 3D reference system) or cortical flattening. Alternatively, the anatomic and functional data may be registered into the same coordinate system so that they have an aligned set of 3D axis and the anatomic data can be segmented and parcellated into precise anatomic locations for later superposition on the functional data. Segmentation and parcellation is a reproducible method using a standard format for locating and defining the boundaries of brain regions. The quantified volume of each brain region is one output of the process. Anatomic and functional data are ultimately co-registered so that fMRI functional data can be evaluated for each individual on their native anatomy. Such techniques may be the primary means of anatomic localization of significant signal changes, or be a supplement to use, of uniform anatomic spaces such as that of Talairach and Tournoux for primary anatomic analysis.

In a hypothesis testing and determination of significant activity phase 504, targeted anatomic regions having significant signal changes relating to experimental conditions, physiology, and psychophysical measures are evaluated. Experimental conditions include variables built into the experimental paradigm, variables built around the group or groups of subjects being scanned and potentially compared, variables involving any administered drugs or compounds, and variables involving repeated administration of the paradigm, or comparison of this paradigm to another paradigm. Hypothesis testing involves correction for the multiple comparisons between experimental conditions being made. Determination of significant activity throughout the entire brain, or throughout the entire set of acquired functional data, will also be performed using a correction for this larger set of comparisons. Hypothesis testing and determination of significant change will also be performed for comparisons generated by the physiology and psychophysics data.

In a signal evaluation phase 506, signal features relative to the experiment are evaluated. Evaluation of signal features involves quantification of indices including but not limited to Talairach coordinates and subregions or subnuculei, Tp and, rate of signal change, first, second and third moments, right side activation (i.e. measure of activation of a structure in the right hemisphere—denoted R), left side activation (i.e. measure of activation of a structure in the left hemisphere—denoted L), fractional laterality (i.e. an index of how lateral an index is computed as $(R-L/R+L)$, correlation factor (R), volume, exponent of power function, amplitudes of harmonics and subharmonics, amplitude changes between plateaus (computed via integration of an fMRI signal of a region) and maximum rate of change and time to achieve the maximum rate of change (computed by taking a derivative of an fMRI signal in a region).

This evaluation of signal features is important for understanding how a signal in a specified anatomic region may be significantly different between experimental conditions, or across physiological changes or changes in psychophysics responses. The evaluation of signal features is not limited to the four categories mentioned above. These four categories in particular, are mentioned because they allow one to evaluate patterns of signal within specified anatomic regions. These patterns within one anatomic region can also be compared to patterns within other anatomic regions. Sets of regions with similar signal features can then be "clustered" together for discussing the dynamics of activation across multiple brain regions.

In a signal quantification phase 507, a calculation of specific indices which can be compared across experimental conditions across brain regions, and sometimes across separable experimental paradigms is made. Quantities which are included in the computation of the indices will be discussed below in conjunction with FIGS. 11–11J. The primary use of quantified indices of an fMRI signal is that sets of these indices become very precise descriptors of signal events in anatomic regions. These sets of indices (e.g., characteristics of the waveform such as the time-to-peak measure) can be used to categorize large numbers of brain regions by experimental condition. These categorizations of multiple regions quantify a "pattern" of activation which can be evaluated across multiple experimental conditions, or can be used to compare experimental condition effects to physiological effects or to psychophysics-relevant effects. These patterns can also be used to compare individual subjects, or follow them over time. Quantified signal indices compliment but do not replace the signal features described in step 506 above.

In a comparison of experimental vs. physiological effects phase 508a, patterns of significant signal change in hypothesized brain regions and elsewhere in the brain are compared and contrasted between experimental conditions and effects related to physiology. Similarly, signal features and quantified signal indices are compared and contrasted between experimental conditions and physiology. This is done to determine what experimental effects are truly independent of mainly global effects produced by body physiological changes.

In a comparison of experimental vs. psychophysical effects phase 508b, patterns of significant change, signal features and quantified signal indices in hypothesized brain regions, and elsewhere in the brain are compared and contrasted between experimental conditions and effects associated with the psychophysical responses. This is done to determine which experimental condition effects and psychophysical response effects are (dependently) linked, and which are independent.

In an interpretation of experimental results phase 509, experimental condition effects and psychophysical response effects which are independent and dependent on each other are evaluated with regard to known functions of the targeted (hypothesized) brain regions and other brain regions. Interpretation of experimental paradigm results in individual subjects or groups of subjects is performed against a background of established brain response features and quantified indices for particular paradigm conditions $\{a_1 \rightarrow a_n\}$, which reflect (or were designed to interrogate) specific motivational or emotional functions. Thus, components of motivation function from blocks 80, 82, or 84 (in FIG. 2C), such as expectancy phase 86 through outcome phase 96, which reflect subfunctions of block 82, are connected to experimental paradigm conditions or psychophysical responses. This connection of experimental paradigm and psychophysics results to motivation and emotion functions is then used to answer the query leading to the initial formulation of the experiment.

Figure 5C:
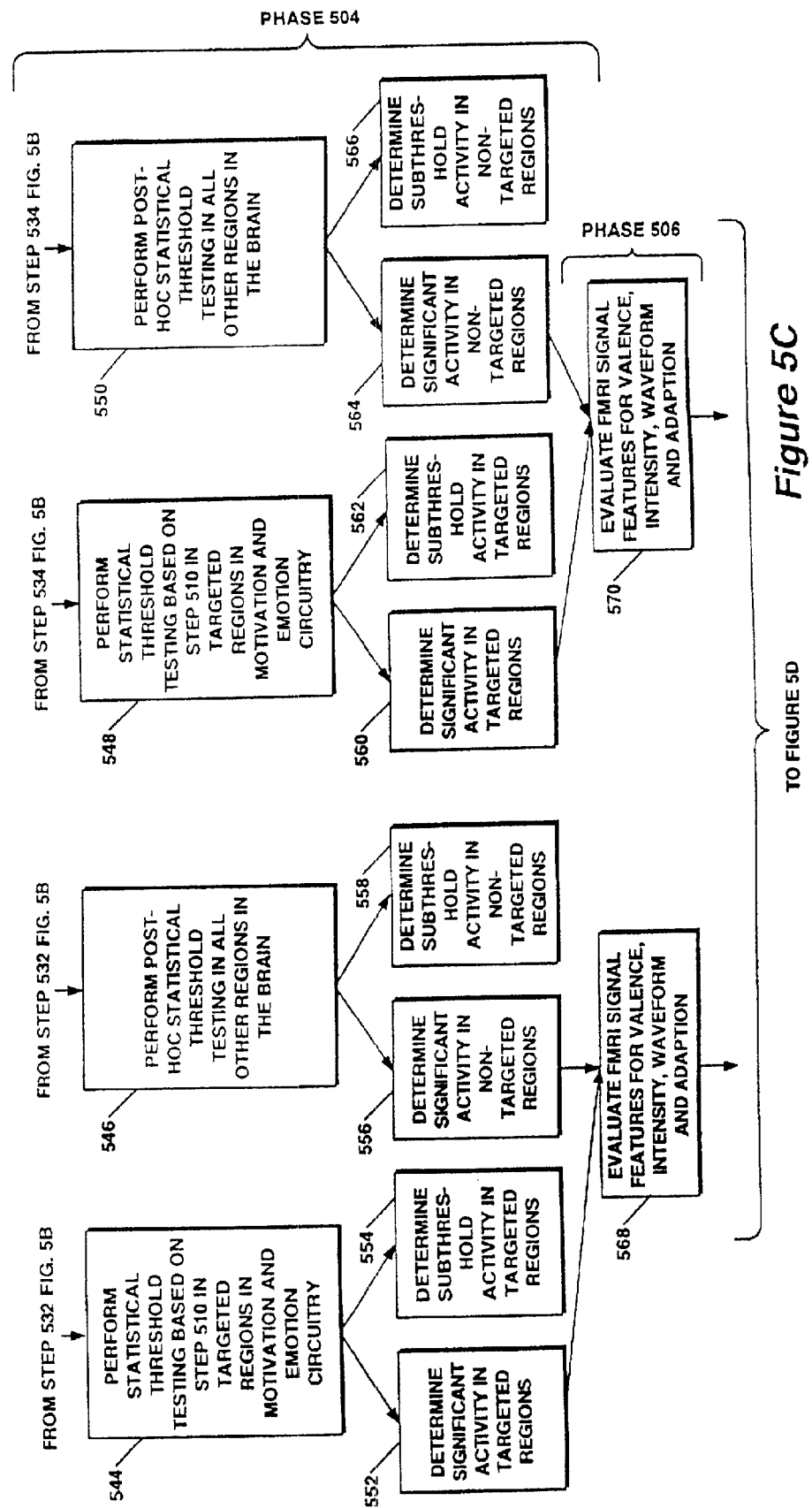
Figure 5D:
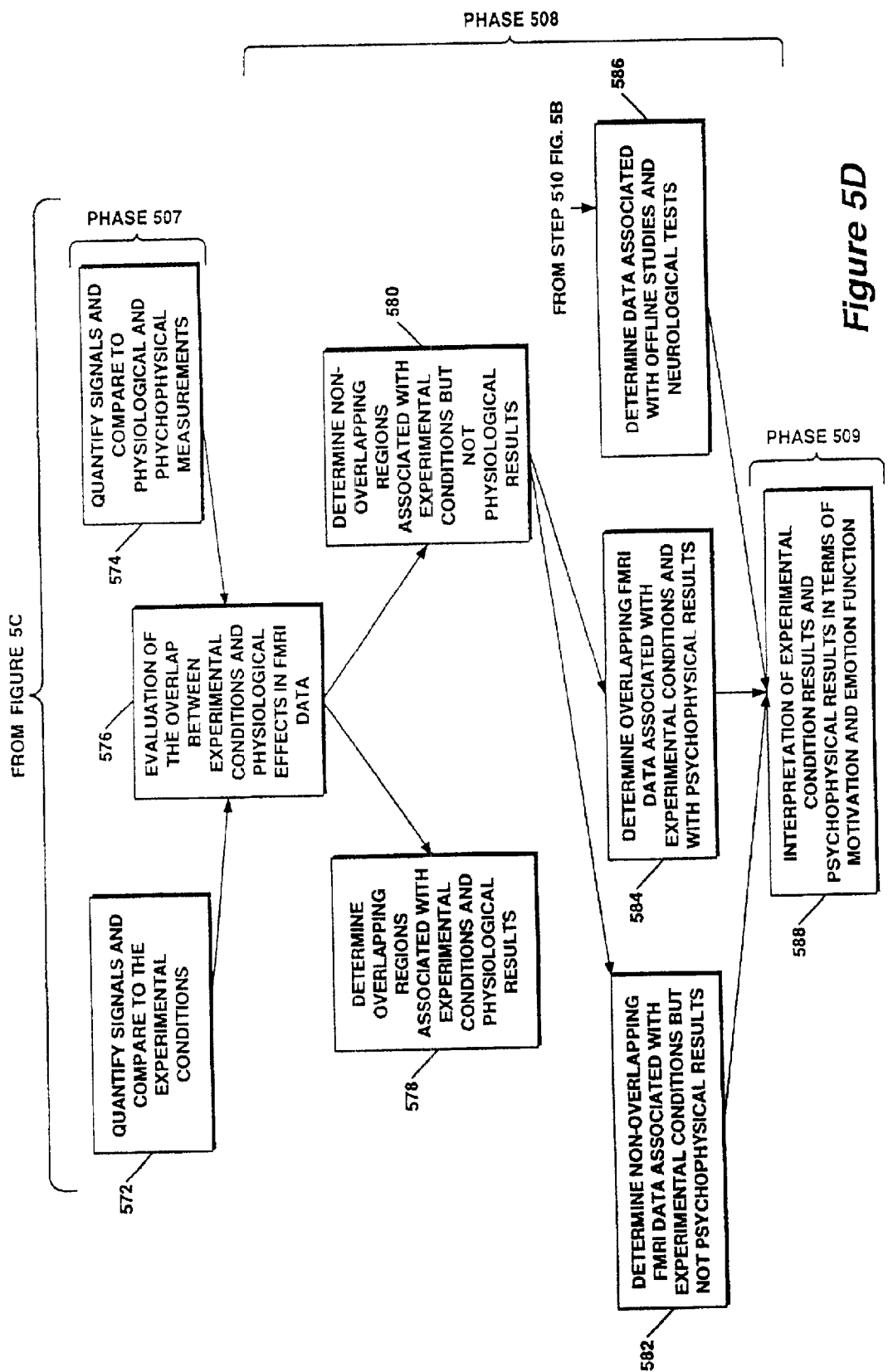

Referring now to FIGS. 5B–5D, the steps in the Motivational/Emotion Mapping Process (MEMP) are illustrated. The process described in conjunction with FIGS. 5B–5D corresponds to both the process used to determine the circuitry as well as the process used to arrive at a conclusion (e.g. "the subject likes the product" or "the subject is lying"). The process begins as shown in step 510 in which an experimental paradigm is developed targeting motivational/emotional function from one of the three general processes needed for motivated behavior. These processes are (1) determination of objectives for survival and optimization of fitness, (2) extracting information from the environment regarding potential goal objects, events or internal states, of relevance to motivational function and meeting the above objectives; and (3) definition of behavior to obtain the goal objects and thus meet the objectives for survival. The experimental paradigm involves a number of discrete conditions which are to be independently measured or compared and are referred to herein below as conditions $\{a_1 \rightarrow a_n\}$. It is important to note that experimental conditions include variables built around the group or groups of subjects being scanned and potentially compared, variables involving any administered drugs or compounds, and variables involving repeated administration of one paradigm or comparison of this paradigm to another paradigm. The experimental paradigm may be integrated with parallel physiological measures (e.g., heart rate (HR), blood pressure (BP), temperature, skin galvanic response SGR, etc.) and/or with parallel psychophysics measures (e.g., analog rating scales of pain or pleasure, response times etc.)

The types of experiments which can be developed in step 510, can be quite diverse. Examples of experiments which can be split into conditions $\{a_1 \rightarrow a_n\}$ are provided by a representative cocaine vs. saline infusions study, a monetary reward study and a beauty bar-press procedure.

For example, the cocaine vs. saline infusions experiments were split into pre-vs. post-infusion conditions. Namely, condition $a_1$=pre-cocaine infusion, condition $a_2$=post-cocaine infusion, condition $a_3$=pre-saline infusion, and condition $a_4$=post-saline infusion.

For the monetary experiment, there were nine experimental conditions depending on the combination of expectancy and outcome conditions for a wheel of fortune. Namely, given three possible outcomes on each spinner, and three spinners, there were three total expectancy/outcome combinations.

In the beauty bar-press procedure, subjects bar-press to keep a picture up longer, bar-press to get rid of a picture quicker, or do nothing. The time interval before each of these 3 conditions represents $a_1$, $a_2$, and $a_3$. These experiments result in a set of experimental conditions $\{a_1 \rightarrow a_n\}$ which are separable either in time, or by correlation with physiological or psychophysical measures.

Experiments developed in step 510 incorporate principles from neurobiology, clinical pharmacology, cognitive neuroscience, decision theory, neurocomputation and medicine including psychiatry and neurology. The experiments are hypothesis driven. Regions can be specified a priori on the basis of the current neuroscience and medical literature at the time. Experiments incorporate a number of conditions whose comparison make it possible to attribute function to targeted brain regions. Examples of such experiments can be seen in double-blind cocaine infusions, thermal stimulation experiments to evaluate pain processing and monetary reward experiments (described below in more detail). Step 510 includes the development any off-line testing if required.

In step 512, subjects are selected and screened for study. The subjects may be human, or animal, depending on the experimental question behind the experiment developed in step 510.

In step 514, neuroimaging parameters are optimized and tested. The optimized parameters are integrated into the experimental paradigm $\{a_1 \rightarrow a_n\}$. The integration of any potential infusion with radioligand, nucleotide, or contrast material into the sequence of scans planned for experimental conditions $\{a_1 \rightarrow a_n\}$ occurs in step 514.

A number of regions can be targeted, for example the subcortical gray matter structures. An attempt is made to reduce potential artifacts affecting signal from deep gray matter structures by optimizing machine parameters. For example, to see the nucleus accumbens or amygdala, one might acquire signals using nearly isotropic voxel dimensions and reduced echo times. In addition, shimming methods known in the art can be used to enhance the homogeneity of the mean magnetic field via use of second or higher order shims.

In step 516, paradigm conditions $\{a_1 \to a_n\}$ are administered in temporal linkage with step 518.

In step 518, brain imaging results in signal acquisition in time and space using optimized machine parameters (including potential infusion with radioligand or contrast agent).

In step 520, physiological and psychophysics parameters are measured in linkage with brain imaging from step 518. Non-invasive physiological parameters (measured outside or inside the functional brain imaging unit) include any/all measure/s of physiological function such as heart rate (HR), blood pressure (BP) including systolic, diastolic and mean using a cuff, skin galvanic response (SGR), skin blood flow as measured by laser Doppler, respiratory rate (RR), electrocardiogram (EKG), pupilometry, electroencephalography (EEG) etc.

Invasive physiologic parameters can include blood pressure (via arterial line), blood oxygenation levels or any similar pulmonary measure using blood sampling, hormonal levels as measured by repeated blood sampling and subsequent assays, drug levels or levels of any injected compound which may be part of the experiment, etc.

Psychophysical parameters include any subjective response (which may be recorded by voice) or a device (such as a mouse) used in the magnet by the subject to respond to questions presented to them inside or outside the magnet. Examples include visual analogue scores, hedonic measures, reaction times, experiment guided responses (e.g., true/false), or other means of communicating internal states etc.

Note, most of the physiological parameters can be measured in animals and humans. However, psychological parameters are mostly specific to humans.

In step 522, an examination of the imaging signal in 3-D relative to the experimental paradigm is made. As an example of the many signal processing and statistical mapping techniques available for fMRI data, two basic approaches to fMRI data analysis will be described. In the first approach, the system targets a set of anatomically defined regions of interest (i.e., NAc, amygdala, SLEA, VT/PAG for a reward/aversion study), and evaluates signals from these regions using two statistical mapping techniques. A second approach evaluates signals throughout the entire brain, including the extended set of regions implicated in reward/aversion functions, such as the GOb, medial prefrontal cortex, aCG, and insula. This post-hoc analysis evaluates averaged data with a similar set of statistical methods as for targeted reward regions, but could also be focussed on individual data. The examination of the imaging signals, occurs in 3-D, relative to experimental paradigm. It should be appreciated that some of the MEMP steps could become automated or semi-automated.

Prior to statistical mapping, initial signal processing involves motion correction which uses the automated image registration or some similar type of motion correction (AIR) algorithm or similar programs which are applied to individual data sets. After motion correction, all individual images are evaluated for residual motion artifacts. Functional MRI data may be intensity scaled and linearly detrended. Spatial filtering may be preformed using a Hanning filter with a 1.5 voxel radius, and then mean signal intensity is removed on a voxel by voxel basis.

During analysis of the targeted reward regions, all individual structural and functional data sets can be transformed into a uniform anatomic space such as Talairach space or a group specific anatomic space to allow statistically significant findings to be aggregated across subjects. In contrast, for voxel-by-voxel analysis, whole brain structural and functional data are transformed into a uniform anatomic space such as Talairach space or a group specific anatomic space prior to averaging across subjects. The averaged functional data is then statistically evaluated as described below in conjunction with steps 522 through 566.

In parallel to the analysis of functional data using parametric statistical mapping (and multiple correlation mapping described below), as shown in Phases 502, 503 the structural scans for each individual have the targeted brain regions segmented (e.g., NAc, SLEA, amygdala, and VT). These segmentation volumes can then be transformed into a universal anatomic space such as Talairach space, or a group specific space. Each activation cluster identified on the group average data is evaluated to determine its localization in these segmentation volumes. Each cluster, which is localized in a particular segmentation volume for 80% or more of the individuals comprising the average, is kept for subsequent analysis.

For the statistical parametic maps, these selected clusters in the targeted regions (e.g., NAc, SLEA, amygdala, and VT/PAG) can be used to sample the individual Talairach-transformed functional data (or functional data transformed into another universal or group specific anatomic space). This individual data can be submitted for robust location and scale estimation using the Tukey bisquare method to evaluate experimental conditions and determine differences between them. Differences across experimental conditions may emerge quantitatively when conditions are sampled together (i.e., morphine vs. saline effects on thermal pain stimuli), or qualitatively in the form of differences in patterns of activation in each of the a priori structures when the conditions are sampled separately. For each analysis across conditions, clusters which have a significant result by robust analysis of variance (ANOVA) will then undergo pairwise contrasts.

In step 524, an anatomic framework or map in 3-D is generated which can localize fMRI signals.

In step 526, examination of imaging signal, in 3-D, relative to physiology, and, separately relative to psychophysical function, can be performed to produce location and scale estimates for statistical evaluation of physiology, & psychophysical effects on brain function.

As part of step 526, individual fMRI data are also evaluated for correlational mapping of subjective effects (as from hedonic analog scales), and correlational mapping of physiological measures correlational analysis will involve multiple correlation of subjective ratings and/or physiological measures with the fMRI data set during which they were collected in each subject. Correlation maps are composed of correlation factors for each pixel. Correlation factors are transformed into probability values using a Fisher transformation. Correlation maps for each individual are anatomically morphed into the Talairach domain or another universal or group anatomic space. These p-value maps are evaluated across each experimental group using a conjunction analysis to quantify the commonality of activations across experimental conditions. The conjunction maps representing the association of subjective effects with fMRI data in individuals are evaluated by identifying clusters of activation in the NAc, SLEA, amygdala, and VT (or other a priori reward/aversion regions).

Evaluation of brain data from regions not included in the initial set of targeted regions can involve use of whole brain data averaged or aggregated across subjects. Alternately, it could also be done in individuals given a sufficiently large cohort for statistical power reasons. A number of statistical mapping procedures are currently available for post-hoc analysis. In one embodiment, a statistical mapping procedure is performed on a voxel-by-voxel basis, using both a wareform based correlation (WCA) analysis, and a multiple correlation analysis.

Analysis of fMRI data can be broadly grouped as model-free or model-based methods, and time-preserving or non-time preserving methods. Most data analysis methods use distribution statistics, such as Student's T-test or Kolmogorov-Smirnov statistics. In these designs a constant hemodynamic response during stimulation is assumed. These techniques are not time-preserving since they compare distribution of activated time points versus resting time points regardless of their time order. Model-based, time-preserving techniques, such as correlation analysis and in some cases, event-related fMRI, maintain the temporal information by including in their analysis the particular time evolution of the model for the fMRI response. These techniques may have some limitations in detecting CNS activation if more than one hemodynamic response is present. The use of an a priori hemodynamic model may mask structures whose responses differ from the chosen model.

In step 524, anatomical localization is performed. Such localization can be accomplished using a number of different techniques. Preferably, anatomic localization is performed using universal anatomic coordinate systems (e.g., Talairach & Tournoux), individual anatomy (e.g., as with segmented brain volumes), and/or anatomically morphed anatomy (e.g., inflated flattened cortical surfaces).

Preferably, anatomically segmented and parcellated brain regions are used for anatomical localization of signal changes. It should be appreciated that alternate embodiments may be developed in the future for more sophisticated and detailed anatomical localization of signal changes observed with functional imaging.

The segmentation methodology, founded upon intensity contour and differential intensity contour concepts is used in step 524. The cortical parcellation technique is based upon the concept of limiting sulci and planes and takes advantage of the observed relationships between cortical surface features and the location of functional cortical areas. An example set of operational definitions is presented in Caviness et al., 1996; Makris et al., 199 which is hereby incorporated herein by reference in its entirety. A critical advantage of this method is that definitions are unambiguously definable in a standardized fashion from the information visible in high resolution MRI.

As is known in the art, targeted regions (e.g., the NAc, SLEA, amygdala, VT/PAG) will have specific anatomic definitions. For instance, for the NAc, SLEA, anygdala, and VT/PAG, the following definitions can be used. The NAc is identified at the inferior junction between the head of caudate and the putamen. The NAc is delimited superiorly by a line connecting the inferior corner of the lateral ventricle and the inferior most point of the internal capsule abutting the NAc and laterally by a vertical line passing from the latter point. The VT/PAG and amygdala is directly visualized, and the posterior extent of amygdala is located at the identical coronal plane as the anterior tip of the anterior hippocampus. The PAG is contained in parcellation units that include the midbrain tegmentum. The SLEA region is identified anteroposteriorly from the midsection of the NAc extending back to the first substration nigra (SN) coronal section. It is identified medially by the hypothalamus (which extends anteroposteriorly from anterior commisure to include posteriorly the mammily body (MB), having a vertical line at the level of the optic tract or the lateralmost extent of the optic chiasm of the internal capsule as its lateral border and the interhemispheric midline as its medial border).

It should be appreciated that the signal processing and statistical analysis is described in terms of the current state of the art for fMRI data. It is recognized that data collection techniques will likely change over the coming years. The statistical procedures may vary somewhat between neuroimaging techniques, but should all involve location and scale estimation, along with techniques for computing general effects and pairwise differences between experimental conditions. The inventive method is compatible with other imaging techniques and future imaging techniques which produce location and scale measurements having equivalent resolution characteristics to current fMRI imagers (i.e. at 3 Tesla and 7 Tesla).

As discussed above, in step 522, an examination of imaging signal, in 3-D, relative to experimental conditions $\{a_1 \rightarrow a_n\}$, produces location and scale estimates for statistical evaluation of paradigm effects. It should be appreciated, however, that the exact sequence of steps between step 522 and step 566, regarding statistical evaluation and anatomic localization may vary, as may the specific method for statistical evaluation or anatomic localization.

In step 528, images from step 522 with those in 524 are merged to allow localization of brain imaging signal for experimental conditions $\{a_1 \rightarrow a_n\}$.

In step 530, brain imaging signals associated with physiology and psychophysics measures are localized.

During the hypothesis testing and determination of significant activity phase 504, brain impulse signal from targeted regions is identified on the basis of previous for reward/pain relevant regions, other imaging studies, or animal data.

The hypothesis testing and determination of significant activity shown in phase 504, includes steps 532–566.

In step 532, an operator or an automated process splits localized results for experimental conditions $\{a_1 \rightarrow a_n\}$ into regions which are a priori (i.e., targeted) and those which are not.

In step 534, an operator or an automated process splits localized results for physiology and psychophysical conditions to regions which are a priori (i.e., targeted) and those which are not.

Hypothesis testing continues in steps 544–550. In step 544, statistical threshold testing based on step 510 is performed on the targeted regions within the motivational and emotional circuitry.

In steps 544, 546, 548, 550, thresholds of significance are computed for the statistical tests to allow for multiple statistical comparisons. This is done in a different fashion depending on the type of statistical analysis being preformed. One method involves using a region of interest analysis to sample maxima of signal change within targeted regions. The signal from these targeted regions in individuals is then submitted to an ANOVA analysis where the p value threshold is corrected for the number of regions being sampled. In contrast to this, a voxel by voxel technique of analysis might incorporate another format of threshold correction. One means of doing this is to measure the volume of tissue sampled in targeted/hypothesized regions, to determine how many voxels cover this tissue, and to divide the p<0.05/x, where x=the number of voxels, to maintain an overall alpha level of less than 0.05. The volume of tissue for the entire brain is also then sampled and used in a similar fashion to produce a correction similar to a Bonferroni correction. After computing thresholds of significance for targeted and non-targeted regions, imaging data from targeted regions is evaluated to determine which data meet a priori and post-hoc thresholds.

In step 544, targeted brain regions are evaluated to determine if they have significant general effects and significant effects between experimental conditions.

In step 546, evaluation of whole brain data (i.e., this may be on a voxel by voxel basis for every voxel acquired during the experiment in the brain), is performed to determine if there are significant general effects and effects between conditions. In step 548, the same procedure is followed regarding the evaluation of physiologic and psychophysical effects in the fMRI data. In step 550, the same procedure used in step 546 is followed, to evaluate physiological and psychophysical effects. The output of the process in step 544 is noted as steps 552 and 554, the output of step 546 is noted as steps 556 and 558, the output of step 548 is noted as steps 560 and 562, and the output of step 550 is noted as steps 564 and 566. The rationale for segregating these outputs in this fashion, is that only steps 552 and 556 contribute the input to the processing which takes place in step 568. Similarly, only the output of step 560 and step 564 contribute the input to the processing of step 570.

In step 552, significant activity in targeted regions from threshold assessment in step 544 is determined. In step 554, subthreshold activity in targeted regions from threshold assessment in step 544 is determined. In step 556, significant activity in non-targeted regions from threshold assessment in step 546 is determined. In step 558, subthreshold activity in non-targeted regions from threshold assessment in step 546 is determined. In step 560 significant activity in targeted regions from threshold assessment in step 548 is determined. In step 562, subthreshold activity in targeted regions from threshold assessment in step 548 is determined. In step 564, significant activity in non-targeted regions from threshold assessment in step 550 is determined. In step 566, subthreshold activity in non-targeted regions from threshold assessment in step 560 is determined.

In step 568, the system evaluates signal features relative to the experiment (e.g. signal valence, graded intensity information, intensity over time and adaptation dynamics). Two examples of evaluating signal features with biological significance are described below. In particular, the use of valence information (from pain and facial expression stimuli), and graded intensity information (from monetary reward stimuli) are described.

In step 568, during fMRI of rewarding or aversive stimuli in humans, positive activation (signal change) in the NAc following rewarding stimuli (including monetary reward, beauty, and drug reward) and negative activation (decreased signal change) following noxious thermal stimuli is observed. These findings directly show that painful stimuli are assessed distinctly from rewarding stimuli, as reflected by an altered valence of NAc signal change. In step 570, the system evaluates of signal features relative to subjective ratings (intensity over time).

One example of the steps included in phase 506 would be a comparison of cocaine infusion maps generated by the comparison of the pre-infusion interval with the post-infusion interval with the statistical maps generated by correlation of subjective ratings with the brain signal. Thus, activations produced by the cross-correlation of rush and/or craving ratings with brain signal can be overlaid with the activations which represent the response to cocaine in general. Some activations from the general cocaine map will correspond with the activations that correlate to rush, others will correspond with the activations that correlate to craving, while a third set may correspond to both, and a fourth set may not correlate to either craving or rush.

In steps 572 and 574, the signals are quantified and compared between experimental conditions. In step 572, the signal features within the same anatomic foci and between different anatomic foci are quantified (i.e., to produce for instance, time to peak and dispersion measures) and compared to experimental conditions $\{a_1 \to a_n\}$. Also in steps 572 and 574, the use of quantified signal indices can describe signal events in anatomic regions. These anatomic regions can then be categorized by these descriptions to show a pattern of signal response across many regions. For example, thermal pain data can be evaluated to produce time-to-peak measures ($T_p$) and dispersion measures ($\Delta$) (i.e. the width of the signal change in response to a painful stimulus from the point of inflection of the signal to its return to baseline). These $T_p$ and $\Delta$ measures can then be evaluated across all regions showing significant signal change (both targeted/hypothesized regions, along with all other brain areas) and divided on the basis of being above or below the mean $T_p$ and mean $\Delta$. This division was legitimized since there were two peaks of $T_p$ and $\Delta$ across the set of regions with significant change. The categorization of regions into a matrix with (a) $T_p < T_p$ mean and $\Delta < \Delta$ mean, (b) $T_p < T_p$ mean and $\Delta > \Delta$ mean, (c) $T_p > \Delta$ mean and $\Delta < \Delta$ mean, and (d) $T_p > T_p$ mean and $\Delta > \Delta$ mean, categorizes the entire set of anatomic regions activated by the experimental condition of applying an aversive (painful) thermal stimulus. This pattern of activated regions can be directly compared to the patterns from other experimental conditions to determine differences between conditions in terms of anatomic regions involved in the different conditions. The categorization of $T_p$ and $\Delta$ above was compared to that from a non-aversive/non-painful thermal stimulus to show the differences in brain regions processing these two categories of stimulus. There are many potentially quantifiable signal indices. Depending on the number of indices used, an N-dimensional matrix can be used to categorize the regional activations so by with the N indices.

In step 574, the signal features within the same anatomic foci and between different anatomic foci are quantified and compared to physiological and psychophysical measurements. In step 576, the overlap between experimental condition and physiological effects, and the overlap between experimental conditions and psychophysical effects is evaluated. For example, autonomic (e.g. GSR) responses, physiological measures (e.g. EKG, BP, RR) or psychological measures (e.g. pain intensity, pain unpleasantness) can be correlated with the brain signal. In this way one can correlate the specificity of the responses with specific regions of the brain that may mediate these physiological/psychological responses.

Time course verification of statistical maps occurs in Phases 506 and 507. Foci of apparent significant change in hypothesized regions, and elsewhere in the brain, are further evaluated by examining the corresponding signal intensity vs. time curves, both for time course data taken from ROI constrained activation clusters (in individuals), and for posthoc voxel-by-voxel focused activation maps. This also provides a means of determining an estimate of mean signal change and confirming that regional activation coincides with the timing of stimulus presentation.

In step 578, experimental conditions which cannot be segregated from physiological conditions are identified. These regions do not receive any more processing. In step 580, experimental conditions which can be segregated from physiological conditions in the same anatomic foci, and between different ones are identified. In step 582, experimental conditions which cannot be segregated from psychophysical effects in the same anatomic foci, or between different ones are identified. In step 584, experimental conditions which can be segregated from psychophysical effects in the same anatomic foci, or between different ones are identified. In step 582 or step 584, the subject can be either conscious or non-conscious.

In step 586 offline studies (done outside neuroimaging system) or questionnaires can optionally be used to modulate interpretation of imaging data. Performance on offline studies or scores from offline questionnaires can be correlated with quantitative signal measures from the functional imaging process. It must be stressed here that the primary data is the neuroimaging data, and that data from offline studies are merely used to fine-tune the interpretation of the neuroimaging results.

In step 588, the system interprets the results from the experiment in terms of motivational and emotional function, or changes therein. Signal features in specific anatomic regions or between different anatomic regions convey a specific picture or script of motivation/emotion function. The biological signals define the motivational and emotional function effected by the experimental paradigm.

It should be appreciated that in phases 502–504 statistical analysis is performed on hypothesized/targeted regions (e.g., such as the NAc, SLEA, VT/PAG, amygdala) and post-hoc/non-targeted regions. Parametric statistical mapping of experimental effects in individual fMRI data may begin with an aggregation process, i.e., all experimental runs for an individual are concatenated. Individual data for the aggregated experiments may then be transformed into a universal anatomic space such as the Talairach domain. Data common to each experiment is then averaged or aggregated across all individuals. This averaged or aggregated functional data then undergoes a statistical comparison of its baseline condition vs. all categorically common experimental conditions, to produce the masks used to collect signal intensity data from individual subjects. Thus, for each experimental condition, a test is preformed between a common baseline and all time-points for all experimental conditions which may be subsequently compared. From these statistical comparisons, clusters of activation are identified using a cluster-growing algorithm. To maintain an overall alpha<0.05, this algorithm will localize activation meeting a corrected threshold of p<0.05/x, (i.e., P for the max vox) where x could be the number of hypothesized brain regions interrogated. The cluster growing algorithm will select voxels with p<0.05/x in a set radius (e.g., 7 mm) of a voxel with a minimum p-value (i.e., max vox). Max vox peaks are within a cluster of a standardized number of voxels (e.g., three voxels), each of which meets the statistical threshold. Max vox peaks will also be separated by a standardized distance (such as 4 mm) from any other putative peak.

As an alternative to the statistical analysis technique described above in phases 502–504, an WCA approach can be used. The WCA approach determines statistical significance using cross correlation of each pixel with a mean hemodynamic response (MHR). The MHR is obtained for a subset of active pixels found active by using a T-test. The WCA approach has been used for a noxious heat experiment, and has been found to yield more information than standard approaches, including more robust levels of significance for signal changes, increased numbers of brain regions that are observed to be activated, and temporal differences in signal time courses for proximate activations (e.g. early activation in some reward/aversion regions and late activation in others).

Also in phases 502–504, in conjunction with the WCA analysis, a multiple correlation analysis of the averaged whole brain data using averaged subjective ratings is performed. For both the WCA and multiple correlation analysis, significance is determined by applying a correction for multiple comparisons. Correction levels are determined as follows:

(1) for a priori regions the corrected p value is 0.05 divided by $n_{apriori}$ (a priori=number of pixels sampled in the a priori regions)

(2) for post hoc regions, the p value is 0.05 divided by $n_{post\,hoc}$ (posthoc=number of pixels in whole brain gray matter region sampled, and approximates a Bonferroni like correction).

Phases 502–506 allow one to determine that the effects of aversive stimuli are distinct from rewarding stimuli on the basis of the pattern of reward/aversion activation. This is shown by distinct patterns of reward/aversion region activity seen during studies of the visual processing of negative vs. positive facial expressions. In these studies with facial expressions (i.e., studies with facial expressions which are responses to aversive stimuli, or responses to rewarding stimuli), positive left and right amygdala activation is observed during the visual processing of fearful faces, positive right amygdala activation is observed following presentation of sad faces, and positive left amygdala activation is observed with happy faces.

Experiments can be explicitly designed to dissect the sub-functions of the informational system for motivated behavior. For instance, in one experiment, monetary reward in a game of chance resembling gambling at a slot machine is used to dissect out activity in reward regions related to the evaluation of probability information (i.e., expectancy), and valuation information (in this case under the general outcome phase of the system}. This monetary reward experiment represents the first demonstration that circuitry involved in human motivation can be dissected into sub-component functions. An important feature of the ability to dissect sub-functions of the informational system for motivated behavior is ordered activation in sets of targeted reward regions which reflect the relative magnitude of the reward. Observing the NAc, SLEA, hypothalamus, and amygdala, can determine how rewarding stimuli are relative to each other.

Figure 6:
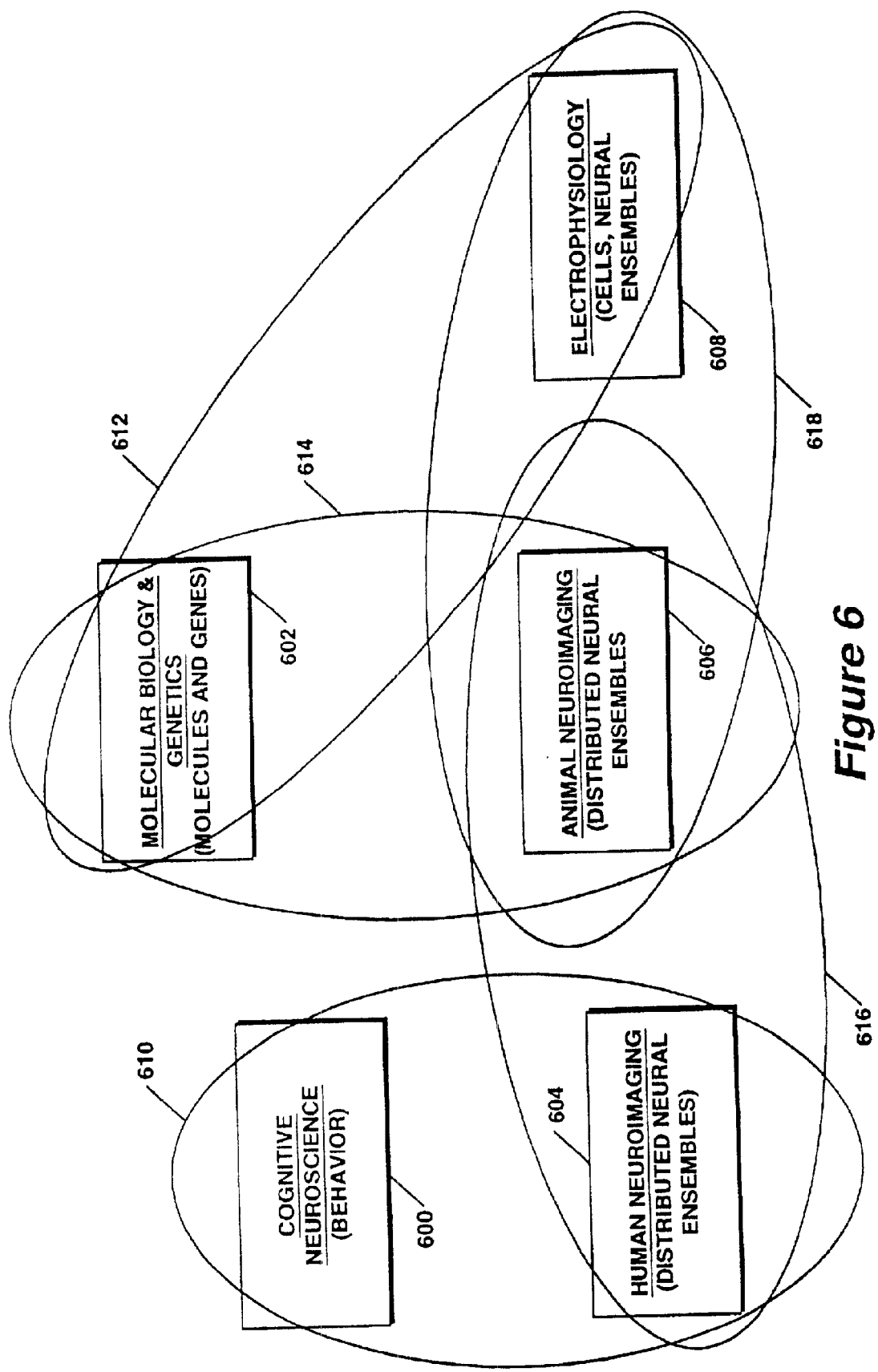
FIG. 6 is a diagram illustrating a number of distract spatial scales of CNS function, and the techniques such as neuroimaging used to interrogate these scales.

Referring now to FIG. 6, a chart shows the relationship of distinct scales of brain function and the research techniques used to investigate these scales. Oval shaped reference lines 610–618 indicate that relationships exist between each of the measurement categories cognitive neuroscience (behavior) 600, human neuroimaging (distributed neural ensembles) 604, animal neuroimaging 606, electrophysiology (cells, neural ensembles) 608 and molecular biology and genetics at the molecular and gene level 602. FIG. 6 is a diagram illustrating an association between functional neuroimaging in humans and animals. The importance of functional neuroimaging in humans and animals is apparent when considering that it is the primary means by which gene and molecular function can be linked to their behavioral effects.

FIG. 6 describes a working format for the interaction of a number of basic neuroscience techniques that measure brain/neural signals from various spatial scales. Thus for example, molecular biology and genetic studies predominantly work with animals to define the contribution of specific genes, modification of these genes or gene products (e.g., receptors) and the effects of molecules (e.g., neurotransmitters) on neuronal function. This evaluation is performed at a cellular/molecular level. However, such techniques may use neuronal markers of activity (e.g., c-fos) to determine the function of groups of neurons throughout the neuraxis. However, this measure is made in-vitro (i.e., special staining methods of brain tissue harvested from animals). Electrophysiology on the other hand may measure the response of a single or multiple neurons to specific activation/perturbation (which may be sensory, mechanical or chemical). Groups of neurons within the CNS may therefore show patterns of response indicative of a particular function of a neuron, group of neurons or brain regions. Neuroimaging, animal or human, allows for the evaluation of signals from neuronal circuits in the living condition. Lastly, cognitive neuroscience and other experimental psychological disciplines allow a description of behavior that can be quantified and interdigitated with neuroimaging (e.g., monetary reward paradigm, using techniques from prospect theory).

Several experiments specific to motivation and emotion function have been performed using the techniques described above. These experiments have produced specific information regarding motivation/emotion functions. For instance, these experiments have involved graded responses to monetary reward in a game of chance, bar press experiments indicating a preference to various stimuli, and experiments evolving direct aversive/rewarding sensations.

In one experiment, the principles of prospect theory (as that term is understood in experimental psychology and behavioral finance) were incorporated into a game of chance with money to evaluate nonnative reward/aversion function during functional magnetic resonance imaging (fMRI) at 3 Tesla. The paradigm involved a sequence of single trials with spinners that shared a subset of outcomes, and segregated expectancy from monetary loss or gain.

In one experiment involving monetary loss and gain, twenty right-handed male subjects were recruited of which eight subsequently were shown after the experiment to have uncorrectable motion or spiking artifact, leading to twelve usable data sets. All subjects were medically, neurologically, and psychologically normal by self-report and review of systems.

This experiment was preformed to map the hemodynamic changes that anticipate and accompany monetary losses and gains under varying conditions of controlled expectation and counterfactual comparison. The paradigm developed in step 510 involved subjects viewing stimuli projected onto a mirror within the bore of the magnet, while maintaining a stable head position by means of an individually molded bite bar. The display consisted of either a fixation point or one of 3 disks ("spinners"). Each spinner was divided into 3 equal sectors. The "good" spinner could yield either a large gain (+$10), a small gain (+$2.50), or no gain ($0), the "bad" spinner could yield a large loss (−$6), a smaller loss (−$1.50), or no loss ($0), and the "intermediate" spinner could yield a small gain (+$2.50), a small loss (−$1.50), or neither a loss nor a gain ($0). Providing larger gains than losses was implemented to compensate for the tendency of subjects to assign greater weight to a loss than to a gain of equal magnitude (per prospect theory).

Before the game began, subjects were shown each spinner 3 times so as to learn its composition. Each trial consisted of (1) a "prospect phase," when a spinner was presented and an arrow spun around it, and (2) an "outcome" phase, when the arrow landed on one sector and the corresponding amount was added to or subtracted from the subject's winnings. During the prospect phase, the image of one of the three spinners was projected for six seconds and the subject pressed one of three buttons to identify the displayed spinner, thus providing a measure of vigilance. The display was static for the first one-half second, and then a superimposed arrow would begin to rotate. The arrow would come to a halt at six seconds, marking the end of the prospect phase. During the first five and one-half seconds of the ensuing outcome phase, the sector where the arrow had come to rest would flash, indicating the outcome. A black disk was then projected as a visual mask during the last one-half second of the twelve second trial. On fixation-point trials, an asterisk would appear in the center of the display for fifteen and one-half seconds, followed by the 0.5-sec mask.

The pseudo-random trial sequence was fully counterbalanced to the first order so that trials of a given type (spinner+outcome) were both preceded and followed once by all nine spinner/outcome combinations and three times by fixation-point trials. Thus, the average 1-trial "history" and "future" was the same for trials of every type. Eight runs with nineteen trials apiece were presented to subjects. Only results of the last eighteen trials were scored for each run, since the initial trial was inserted into the run sequence purely to maintain counter-balancing. Runs were separated by two to four minute rest periods. The same trial sequence was used for all subjects, generating winnings of $142.50, to which was added a $50 endowment. At the end of the scanning session, subjects completed a questionnaire rating their subjective experience of each spinner and outcome using an eleven point opponent scale.

The timing of stimulus events in this experiment, and the rationale for the data analysis, are based on two fundamental assumptions. A first assumption is that the hemodynamic control system is approximately linear in the brain regions targeted by this experiment, on the basis of results from conditions tested to date. A second assumption is that, given appropriate counterbalancing, the compound response can be "peeled apart" by means of selective averaging and comparison of impulse-like hemodynamic responses.

Subject instructions were developed and administered (see e.g. steps 510, 516 in FIG. 5B). Using a set text, subjects were informed that they would be participating in a series of games of chance. At the start of these games, they would receive an endowment of $50 to cover possible losses, and informed of the maximum they could win over the course of the experiment. In the unlikely event that they lost more then their endowment, they would receive no money, but would receive a picture of their brain in action and have a clinical scan on record, worth approximately $1600. For each game of chance they would see a wheel of chance with three sectors. The wheel would move for some time, and the spinner would eventually land on one of the sectors, determining how much they received for that particular game. There would be three wheels of chance, which differ in their general level of outcomes, and would be termed the bad, medium, and good spinners. Subjects were informed they would see each of these spinners in a short video to acquaint them with the game. They were further informed to identify each spinner shown for each game as rapidly as possible using a button box, and to refrain from speech during the scan. After reading the instruction text, subjects' questions were answered, and they then observed a brief set of 10 trials (including the fixation trial) to familiarize them with the stimuli.

Physiological and psychophysical measures of behavior were monitored (in accordance with step 520 discussed above). Subjects made behavioral responses throughout the study, consisting of identification of each spinner as it was presented. Subjects identified spinners using a button box, with the first key on the left (index finger) being used to identify the bad spinner, the second key on the left (middle finger) being used to identity the medium spinner, and the third key on the left (ring finger) being used to identify the good spinner.

Subjects were scanned (in accordance with step 518 discussed above) on an instascan device (3 T General Electric Signa; modified by Advanced NMR Systems, Wilmington, Mass.) using a GE head coil. Imaging for all experiments started with a sagittal localizer scan (conventional T1-weighted spoiled gradient refocused gradient echo (SPGR) sequence; through-plane resolution=2.8 mm; 60 slices) to orient, for subsequent scans, the slices to be acquired for functional scanning. This scan was also used as the structural scan for Talairach transformation. Next, an automated shimming technique was used to optimize $B_0$ homogeneity. Radio-frequency full-width half-maximum (FWHM) line-width after shimming of primary and secondary shims produced a measure of 32.4±2.2 Hertz (Hz) for the 12 subjects with motion-correctable functional data. After shimming, experimental slices were prescribed, with 18 slices parallel to the AC-PC line and covering the NAc, amygdala, SLEA/BF, and VT. In this orientation, an SPGR T1-weighted flow-compensated scan was obtained (resolution=1.6 mm×1.6 mm×3 mm), primarily to aid Talairach transformation during data analysis. The fourth scan was a T1-weighted echo planar inversion recovery sequence (TI=1200 msec, in-plane resolution=1.57 mm) for high-resolution structural images to be used in preliminary statistical maps (but not with Talairach transformed or averaged maps). Finally, functional scans involved a T2*-weighted gradient echo sequence (TR=2 s, TE=35 ms; Flip=70°; in plane resolution=3.125×3.125 mm, through-plane resolution=3 mm, FOV=40×20 cm; 18 contiguous slices, images per slice=108 per run). The shortened TE and nearly isotropic voxel dimensions had been optimized previously in step 514 to minimize imaging artifacts in the regions of interest.

Post-paradigm subjective reports were collected. After finishing the paradigm, subjects completed a questionnaire regarding cumulative gains, and their experience of the prospect and outcome phases of the experimental trials as a means of determining whether they experienced the monetary task in the manner predicted by prospect theory. The questionnaire specifically queried subjects' ability to follow cumulative gains/losses during the experiment, estimates of total winnings, and their subjective experience of spinner presentation, plus outcome from each spinner. To make these ratings of each spinner, and each outcome on the three spinners, subjects marked their response on an 11-point opponent scale ranging from very bad (−5) to very good (+5). Subjects were subsequently informed of their total gains from the experiment. In this particular study, no further offline or neuropsychological measures unrelated to the paradigm itself were performed (as in step 586 FIG. 5D).

Data analysis on behavioral data collected during the paradigm was performed in step 526. The integer output for each behavioral rating was checked against the trial sequence, and performance was listed for each individual. The mean±standard error of the mean (SEM) were computed across the twelve subjects with motion-correctable functional data for each of the eight runs to ascertain that response errors were less than five percent per subject.

Data analysis on post-paradigm data was performed in step 526. The real-number responses of subjects with motion-correctable functional data were tabulated and evaluated using robust methods paralleling those detailed for the fMRI data (see steps, 522–566 FIG. 5B). Specifically, for the subjective ratings of spinner a statistical expert system performed an analysis of raw residuals and recommended against use of variance-adjusted weights and the Tukey bisquare estimator. The efficiency of the robust (bisquare) analysis was only eighty-five percent as great as the efficiency of the traditional least-squares approach, so the recommendation of the expert system was accepted, and a least-squares components ANOVA (one-way) performed with subsequent pairwise comparisons.

For the subjective ratings of outcomes, boxplots of the residuals indicated a number of potential outliers, the presence of which were confirmed with an analysis of raw residuals form the robust fit. The efficiency of the robust (bisquare) analysis was greater than the efficiency of the least squares approach as confirmed with a normal probability plot of residuals, and hence the expert system recommended use of variance-adjusted means and the Tukey bisquare estimator. This recommendation was accepted, and a bisquare components ANOVA (two way—bins nested in spinner) performed with subsequent pairwise contrasts.

The fMRI data was then processed (as in phases 502, 504 in FIG. 5A) and signal processing of fMRI blood oxygen level dependency (BOLD) data before statistical mapping was preformed (in accordance with step 522 of FIG. 5B). To reduce head motion, each subject was positioned using a bitebar, and BOLD data was motion corrected using a motion correction algorithm. After motion correction, time-series series data were inspected to assure that no data set evidenced residual motion in the form of cortical rim or ventricular artifacts>1 voxel. From this analysis, eight of the twenty subjects were found to have uncorrectable motion or spiking artifact, leaving a final cohort of twelve subjects for further evaluation. Motion correction (mean±SEM) of the BOLD data revealed an average maximal displacement for each of eight runs of 0.43±0.097 mm, 0.67±0.16 mm, 0.72±0.18 mm, 0.71±0.15 mm, 0.80±0.19 mm, 1.16±0.30 mm, 1.33±0.39 mm, 1.47±0.43 mm. Motion displacement led to corrections for movement, in terms of the mean correction per time point for each of these runs, of 0.22±0.04 mm, 0.49±0.13 mm, 0.56±0.15 mm, 0.55±0.11 mm, 0.65±0.16 mm, 1.00±0.29 mm, 1.19±0.37 mm, 1.29±0.41 mm.

For all eight runs, fMRI data in the Talairach domain was normalized by intensity scaling on a voxel-by-voxel basis to a standard value of 1000, so that all mean baseline raw magnetic resonance signals were equal (corresponding to step 522 in FIG. 5B). This data was then detrended to remove any linear drift over the course of scan. Spatial filtering was performed using a Hanning filter with 1.5 voxel radius (this approximates a 0.7 voxel gaussian filter). Lastly, mean signal intensity was removed on a voxel-by-voxel basis.

In this experiment, the trials were selectively averaged. In total, there were ten trial types (spinner+outcome), including the fixation baseline. Prospect and outcome phases of the trials each lasted six seconds. Given the standard delay of two seconds for the onset of the hemodynamic response to neural activity, at least fourteen seconds of BOLD response needed to be sampled for selective averaging across trial type. Six seconds of pre-stimulus sampling were incorporated for use in subsequent data analysis as a baseline to zero the onset of each trial. This is a common practice in evoked response experimentation. Counterbalancing was performed to the first order, so that the six seconds before the onset of each trial, when averaged across all iterations of that trial, would represent a common baseline against which to normalized the onset of each trial. Accordingly, selective averaging was performed for twenty second epochs.

Each individual's set of infusion images, along with the associated conventional structural scans, were transformed into Talairach space and resliced in the coronal orientation with isotropic voxel dimensions (x,y,z=3.125 mm) (steps 522, 524 in FIG. 5B). Optimized fit between functional data and structural scans was then obtained via translation of exterior contours.

Talairach-transformed structural and functional data (i.e., the selectively averaged trials, N=10) were averaged across the twelve subjects with interpretable BOLD data (steps 522, 524 FIG. 5B).

Statistical mapping, ROI-based analysis and statistical mapping of main effects as ROI's was then performed (as discussed in phases 502–504 above). All time-points collected during the prospect phase of the experiment, and all time-points collected during the outcome phase of the experiment were statistically evaluated by correlation analysis with a theoretical impulse function. The impulse function for the predicted hemodynamic response was generated using a gamma function. To eliminate cross-trial hemodynamic overlap, the correlation maps were generated with the difference between all prospect data and fixation epoch data, and with the difference between all outcome data and fixation epoch data using time-point by time-point comparison. Subsequently, clusters of activation were identified using a cluster-growing algorithm. In order to maintain an overall $\alpha<0.05$, this algorithm specifically localized activation which met a corrected p-value threshold of $p<0.007$ for the number of hypothesized brain regions being interrogated. Regions of interest (ROIs) were delineated by the voxels with $p<0.007$ in a 7 mm radius of the voxel with the minimum p-value (i.e., max vox). Max voxel peaks had to be within a cluster of at least 3 voxels, making the statistical threshold, and separated by at least 4 mm from any other putative max vox peak. ROIs identified in this manner were then used to sample the individual prospect data (N=10 ROIs) and outcome data (N=6 ROIs).

During the anatomic localization phase 503, statistical maps of group averaged data were superimposed over high-resolution conventional $T_1$-weighted images which had been transformed into the Talairach domain and averaged. Primary anatomic localization of activation foci was preformed by Talairach coordinates of the maximum voxel from each activation cluster with secondary confirmation of this via inspection of the juxtaposition of statistical maps with these coronally resliced T1-weighted structural scans. Confirmation of subcortical localization of activations followed the region of interest conventions described previously for the NAc SLEA, amygdala, and VT. The GOb ROI conventions were not previously described, and are here delineated. Namely, the GOb (BA 11/47) was identified anteriorly behind the ventral surface of the frontal pole (BA10). It began with the orbital gyri (anterior, lateral, and medial) which are visible by the beginning of the orbital sulci, and extended posteriorly to the beginning of the SLEA of the basal forebrain which is visible by the extinguishing of the orbital sulci (transverse orbital sulcus). Laterally, the GOb extended to the anterior horizontal ramus of the Sylvian fissure, and medially, it extended to the olfactory sulcus.

As shown in Phases 502–504 priori regions evaluated for activation clusters included the NAc, amygdala, and VT (for prospects), and the SLEA, amygdala, hypothalamus, and GOb (for outcomes). Regions hypothesized for one condition (i.e., prospects or outcomes), were also evaluated for the other. In total, ten clusters of signal change were noted for these a priori regions during the prospect phase of the experiment. Six other clusters of signal change were noted in a priori regions during the outcome phase of the experiment.

Signal time-course analysis of ROI's was performed in phases 502–504. The normalized fMRI signal was averaged, at each time point, within each activation cluster falling within an ROI. As described above, the averaged data were assembled into time courses, 20 sec in duration, which included a 6-sec epoch prior to trial onset.

An exploratory analysis of the time courses was performed in order to examine the across-subject distribution of the averaged fMRI signal in each cluster. First, the signals for each subject were transformed into deviations from the across-subject mean at each time point within each trial type. The deviation scores for the period beginning 2 sec following trial onset and ending 2 sec following the end of the trial were selected for exploratory analysis, this segment was used because it contained the data that were later used for hypothesis testing concerning expectancy and outcome responses. The deviation scores within the selected time period were combined across time points and trial types and displayed as a normal probability ("quantile-quantile") plot. If the scores of the subjects were distributed normally, such a plot would be a straight line passing through the origin, with a slope equal to the standard deviation.

Normal probability plots of data from some clusters did not deviate strongly from linearity, suggesting that the signals recorded from the different subjects were distributed in an approximately normal fashion. In contrast, substantial deviations from linearity, consistent with the properties of contaminated normal distributions, were noted in the case of several clusters. Thus, it was decided to employ robust statistical methods to describe the time courses. Such statistics are less subject than conventional parametric statistics to the influence of extreme values ("outliers") and provide more efficient estimates of the central tendency ("location") and dispersion ("scale") of contaminated normal distributions. As described below, a formal test of the relative efficiency of the conventional and robust measures was carried out in order to determine whether robust or conventional least-square statistics were the most appropriate for hypothesis testing.

The robust estimates of location and scale are based on the Tukey bisquare estimator (phases 502–504). This estimator weights scores as a function of their deviation from the sample median. The weights decline smoothly to zero in a bell-shaped fashion as the deviation from the median grows. To compute the location estimate, each score is first expressed as a scaled deviation from the sample median:

$$u_i = \frac{x_i - M}{c \times MAD}$$

where
- $x_i$ = fMRI signal for subject i at a given time point
- M = median of the fMRI signals for all subjects at that time point
- c = a tuning constant and
- MAD = the median of the absolute deviations from the median The weighting function is $w_i = (1-u_i^2)^2$ if $|u_i| \leq 1$; $w_i = 0$ if $|u_i|$), the robust estimate of location ($T_{bi}$) is $$T_{bi} = M + \frac{\sum ((x_i - M) \times w_i)}{\sum w_i},$$

and the robust estimate of scale ($s_{bi}$) is $$s_{bi} = \frac{n^{\frac{1}{2}} \times \left(\sum \left((x_i - M)^2 \times (1 - u_i^2)^4\right)^{\frac{1}{2}}\right)}{\left|\sum w_i^{\frac{1}{2}} \times (1 - 5u_i^2)\right|}$$

where n = the number of subjects

The turning constant, c, determines the point at which the weighting function reaches zero. As the value of this constant grows, progressively fewer data points receive zero weight, and the location estimate approaches the mean; as the value of this constant shrinks, progressively fewer data points are rejected, and the location estimate approaches the median. A tuning constant of 6 was employed to compute the location and scale estimates used to graph the signal time courses and their confidence intervals. Given normally distributed data, such a tuning constant would result in assignment of a zero weight to all observations falling more than 4 standard deviations from the median. In the case of the observed distributions, the median percentage of data points assigned a weight of zero was 1.24%. The range for 15 of the 16 clusters was 0.47–2.16%. Whereas the percentage of data points rejected in the case of the remaining cluster was 5.86%.

A baseline adjustment was made. The robust estimates of location and scale were computed first from untransformed data. A within-subject subtraction procedure was then used to align the signal time courses for each trial type with a common baseline. As shown in FIG. 3H in the case of the data to be used for analysis of expectancy responses, the subtrahend consisted of the median fMRI signal during the six seconds prior to trial onset plus the first two seconds of the trial. (Due to the delay in the hemodynamic response, the signal during the first two seconds of the trial should reflect neural activation prior to trial onset.) This median value was then subtracted from the fMRI signals obtained during the subsequent twelve seconds. In the case of the data to be used for analysis of outcome responses, the subtrahend consisted of the median fMRI signal during the first six seconds of the trial (the prospect phase) plus the first two seconds following presentation of the outcome. Thus, in both cases, the median of the signals recorded during the preceding epoch was subtracted from the signals from a given trial phase. Following the application of the subtraction procedure, new robust estimates of location and scale were computed.

The robust estimates of location and scale were used to compute the 95% confidence intervals. Due to the fact that the average weight is less than one, the degrees of freedom must be corrected accordingly. The number of degrees of freedom were multiplied by 0.7 in constructing confidence intervals about the robust estimates of location. The expression for the confidence interval is $$T_{bi} \pm \left(t_{(0.7 \times (n-1))} \times \frac{s_{bi}}{\sqrt{n}}\right)$$

In the hypothesis testing and determination of significant activity phase 504, tests for differences between time courses were carried out using a statistical expert system such as RS/Explore. It should be appreciated that there are several methods and expert systems which can perform the statistical analysis. Separate analyses of the transformed data for the expectancy and outcome phases were conducted.

The multiple-regression module of RS/Explore was employed to carry out an analysis of variance (ANOVA) as part of steps 544–550. In the cases of 12 of the 16 clusters, the data selected for this analysis consisted of the transformed fMRI signals during the period beginning 2 sec following trial onset and ending 8 sec following trial onset. This period lags the timing of the expectancy phase of the trial by 2 sec, consistent with other reports of hemodynamic delay post experimental stimulation.

Examination of the time courses for these 12 clusters confirmed that signals whose confidence intervals cleared zero did indeed lag the onset of the trial by 2 sec. However, in the case of the remaining clusters, the lag was longer. For example, the peak signal in cluster GOb(6) occurred at 6 sec, and that the signal was still elevated at 8 sec. In the four cases such as this one, signal epochs selected for statistical analysis matched the time interval during which the peak signal was attained, and the maximum signal under the curve was observed. Thus, for cluster GOb(6), a 4 second lag allowed selection of the time interval with both the peak signal and maximum signal under the curve.

The data segment selected for analysis of expectancy responses in the case of the 3 other ROIs also consisted of the points at 4, 6, and 8 seconds. Regardless of the hemodynamic lag, the duration of the sampled period was 6 seconds.

The dependent variable in the expectancy ANOVA was the transformed BOLD signal, and the predictors were the spinner and time point. Both spinner and time point were defined as categorical (non-continuous) variables, thus forcing the analysis software to carry out an ANOVA in lieu of fitting a regression surface. By defining the independent variables in this fashion, it was possible to avoid making assumptions about the form of the time courses.

At the outset of the analysis, the statistical expect system compared the relative efficiencies of the Tukey bisquare estimator and conventional least-square statistics. In the cases of 15 of the 16 clusters, the Tukey bisquare estimator was found to be more efficient and thus, a robust ANOVA was carried out; graphical confirmation of the need for a robust estimator was provided by normal probability plots. In the remaining case, the least-squares estimator was found to be slightly (~1%) more efficient and thus, as recommended by the expert system, conventional least-square methods were employed.

A second test carried out prior to the ANOVA compared the within-cell variances. In 15 of 16 clusters, these were found to be sufficiently similar that the use of variance-adjusted weights was not recommended. However, in the remaining cluster, the differences between the within-cell variances were sufficiently large as to cause the expert system to recommend the use of variance-adjusted weights.

The results of primary interest in the expectancy ANOVA were the main effect of spinner and the spinner×time point interaction. A main effect of spinner indicates a difference in the magnitude of the fMRI signals corresponding to the presentation of the three spinners; a spinner×time point interaction indicates the form of the signal time courses differed across spinners. Given that ANOVAs were carried out on the signals from 16 different clusters, a more stringent alpha level (0.003) was used than the conventional 0.05 value as the threshold for a significant effect.

In cases that met the criterion alpha level, the pair-wise across-spinner contrasts were computed at each of the three time points. Regardless of whether the main effect of spinner or the spinner×time point interaction met the significance criterion, the confidence band surrounding the location estimate was compared to zero. Given that multiple comparisons were carried out, simultaneous confidence intervals reflecting the variance at all time points during the expectancy phase were used in this comparison.

The outcome-phase ANOVA was largely analogous to the expectancy-phase ANOVA. In all cases, the data employed fell within a 6-sec period beginning 2 sec after the onset of the outcome phase. The BOLD signal served as the dependent variable, and spinner, trial type, and time point served as the predictors; trial type, a categorical variable, was nested within spinner. (A $10 win following the presentation of the good spinner constitutes one trial type, whereas a $2.50 win constitutes another.)

Prior to the ANOVA, the expert system was used to determine whether robust or least-square statistics were more efficient and whether the use of variance-adjusted weights was recommended. A robust ANOVA was carried out in the case of 13 clusters, and a conventional least-square analysis was carried out in the remaining 3 clusters. Variance-adjusted weights were used in 7 of the 16 clusters. In all cases, the recommendations of the statistical expert system were accepted.

The results of primary interest in the outcome ANOVA were the main effect of trial type and the trial type×time point interaction. A main effect of trial type indicates a difference in the magnitude of the fMRI signals corresponding to the presentation of the different within-spinner outcomes; a trial type×time point interaction indicates that the form of the signal time course varied across trial type. As in the case of the expectancy-phase ANOVAs, the criterion alpha level was set to 0.003.

In cases that met the criterion alpha level, pair-wise contrasts were computed between the three trial types within each spinner, at each of the three time points. Regardless of whether the main effect of trial type or the trial type×time point interaction met the significance criterion, the confidence band surrounding the location estimate was compared to zero. As in the case of the data from the expectancy phase, simultaneous confidence intervals were used in this comparison.

In steps 522 and 524 as part of the Statistical Mapping of Imaging Data phase 502 data was produced for the post-hoc voxel-by-voxel correlational analysis in steps 546 and 550. This analysis sought to determine if regions not included in the hypotheses were potentially active during either the prospect/expectancy phase of the experiment, or the outcome phase. Toward this end, statistical correlational maps were generated against a theoretical impulse (i.e., gamma) function. Specific paired comparisons for the prospect and outcome data were the same as the post-hoc comparisons after the ANOVA analysis. These paired comparisons were all preformed against the medium prospect or the intermediate outcome with one exception, namely all comparisons between the good and bad spinners, or the high and low outcomes, were deemed to be redundant since their main comparison was already contained in the dyadic comparisons of good to intermediate, and bad to intermediate spinners.

Clusters of positive and negative signal change were identified for each paired comparison using the automated cluster growing algorithm described above. In order to maintain an overall $\alpha<0.05$, this algorithm specifically localized activation which met a corrected p-value threshold for the volume of tissue sampled in the a priori regions (i.e., $p<4.96\times10^{-5}$ for both prospects and outcomes). All other regions had to meet a corrected (Bonferroni) threshold for significance of $p<7.1\times10^{-6}$ for the estimated volume of brain tissue per subject sampled in this experiment. As previously, max vox peaks identified by the cluster growing algorithm had to be within a cluster of at least three voxels, of which the two voxels which were not the peak had to meet the statistical threshold of $p<0.07$ and be within a 7 mm radius of the max vox.

All activations were further checked against the functional image data to ascertain that they did not overlap areas of susceptibility artifact. Such overlap was determined by whether or not a voxel's signal intensity during the baseline was less than the average voxel in its slice by 50% of the difference between the average voxel signal intensity in the slice and the average voxel signal intensity outside of the slice.

In Phase 506 significant differential responses to monetary outcomes were recorded from the NAc, SLEA, and hypothalamus to the three outcomes on the good spinner ($10.00, $2.50, $0.00). For these ROIs, the time courses diverged similarly, with signal declines during the $0.00 outcome, and less marked declines in the case of the $2.50 outcome. The highest signal levels were recorded in response to the highest value ($10.00) outcome, and in the NAc and SLEA, the outcome phase response to this outcome rises towards the end of the trial. In these ROIs, the value of the normalized BOLD signal during the outcome phase tracks the subjects' winnings.

The outcome-phase time courses were aligned to a common baseline by subtracting the median of the normalized BOLD signals recorded during the prospect phase. Thus, even in the absence of a hemodynamic response to the outcome, the recorded signal may have decreased during the outcome phase simply due to the waning of the prospect response. The key to distinguishing bona fide responses to the outcomes from the decaying phase of preceding prospect responses is the differential nature of the outcome-phase responses. As shown by the significant effect of outcome or the outcome by time point interaction in the ANOVAs carried out in 12 of the 16 ROIs, differential outcome-phase responses were indeed observed, distinguishing these outcome results from those of the preceding prospect phase. Nonetheless, the decay of prospect-phase responses may have contributed to driving the outcome-phase signals below zero, which was the case at 37 of the 49 time points at which the outcome-phase signals differed reliably from the baseline. Thirty of these 37 time points moving below zero belong to the NAc, SLEA, and hypothalamus alone. In contrast to these subcortical signals, 11 of the 12 time points that move reliably above the baseline belong to GOb ROIs.

The dominant pattern in the most sustained outcome-phase responses (those that cleared the baseline reliably at the greatest number of time points) is typified by the signals recorded from the NAc, SLEA, and hypothalamus. For these three ROIs, relative to the median of the prospect-phase responses, the signal at the end of the outcome phase is lowest in response to the worst outcome on the good spinner ($0.00), somewhat higher in response to the small gain ($2.50), and highest in response to the large gain ($10.00).

A strikingly different pattern is observed in the case of cluster GOb(4). In that case, the responses to the two most extreme outcomes ($10.00, −$6.00) are higher than the responses to the other outcomes on the respective spinners. Thus, the responses in this ROI provide information about the magnitude of the outcome but not about its sign. Only one other time course, the response to the worst outcome on the bad spinner (−$6.00) in the right amygdala, deviates reliably from the baseline at more than one outcome-phase time point. Again, it is the response to an extreme outcome that stands out.

In phase 507, a number of prospect responses demonstrated signals with distinct time to peak measures. Signals from subcortical and brainstem structures with robust simultaneous 95% confidence bands that cleared the baseline, peaked at 4 seconds in 10 of 13 cases. Several of the signals that peaked later were recorded in GOb ROIs, for instance, differential lags are apparent during responses to the good spinner in the SLEA and in GOb(6). It is important to note, for the SLEA and GOb(6), that slice acquisition occurred in interleaved fashion in the axial domain, parallel to the AC-PC line, with a through-plane resolution of 3 mm. The functional data from activations in the SLEA (Talairach coordinates: 18, 0, −6) and GOb(6) (Talairach coordinates: 25, 59, −18) were acquired only one slice apart. Thus, at each time point, at most 100 msec separated acquisition of signal in the SLEA and GOb(6). In contrast, the peak of SLEA signal leads the peak of the GOb(6) signal by 2 seconds, and the GOb(6) response remains near its peak value for an additional 2 seconds during which time, the SLEA signal declines. The temporal separation of these acquisitions cannot be accounted for by technical or averaging constraints.

Phase 508, was not applicable to this experiment.

Research on the psychology of monetary gains and losses shows that the subjective response to an outcome depends on the alternative outcomes available and on prior expectation. In Phase 509, the interpretation of the results suggest that this was also the case in the BOLD signals recorded in the NAc, SLEA, and hypothalamus in response to the $0 outcomes. On the good spinner, $0 is the worst of the three outcomes available. The responses to this outcome fall throughout the outcome phase, dropping below the other time courses. In contrast, the NAc and SLEA responses to the $0 outcome on the bad spinner are rising at the end of the outcome phase, around the time when a hemodynamic response to an outcome might be expected to peak: these signals climb above the responses to the $0 outcome on the good spinner, as does the bad-spinner response in the hypothalamus. The $0 outcome on the bad spinner is the best available on that spinner. Indeed, the form of the BOLD time courses recorded during the outcome phase of bad-spinner trials on which the outcome was $0 resembles the form of the responses in the NAc and SLEA to the best outcome ($10.00) on good-spinner trials. Finally, the psychological research predicts that the $0 outcome on the intermediate spinner, which falls between the two other values, will be experienced as near-neutral. The normalized BOLD time courses corresponding to presentation of this outcome fluctuate near the zero baseline.

The design of this experiment takes into account several principles that have emerged from the psychological study of judgment and decision. Paramount among these is the view that the emotional impact of an outcomes depends strongly on the context within which they are experienced. Thus, the experiment was designed so as to control and manipulate prior expectations as well as post-hoc comparisons with the alternative ("counterfactual") outcomes available. Both the psychological and neurobiological literature suggest that different processes are brought to bear when anticipating and experiencing outcomes. Thus, the trials were structured so as to separate over time the responses of the subjects to prospects and outcomes. Psychological research shows that losses with respect to a neutral point tend to loom larger than gains of the same magnitude. Larger gains than losses were employed in an attempt to offset this tendency. Five different monetary amounts were used, enabling us to determine how the BOLD signal varied as a function of the magnitude and sign of the outcomes. By including one common outcome on all three spinners, the influence of expectation and counterfactual comparison could be assessed. The asset position (cumulative winnings) of the subject was not displayed, thus increasing the likelihood that performance on each trial would be referenced to a common baseline. Modeling of the design of the present study on principles well established in prior psychological research on judgment and decision may have been crucial to the clarity and orderliness of the BOLD signals as well as to their tight linkage to trial events.

The importance of functional neuroimaging in humans and animals is apparent when considering that it is the primary means by which gene and molecular function can be linked to their behavioral effects.

The description below considers three categories of pain: (acute) experimental pain (sometimes referred to herein as "pain 1") (acute) sensitized (e.g., hyperalgesia) or inflammatory pain, (sometimes referred to herein as "pain 2") and chronic pain nociceptive or neuropathic, (sometimes referred to herein as "pain 3").

As used herein, the term "reward/aversion" circuitry refers to those regions referred to in the art as "classic pain regions" and "reward regions." In accordance with the present invention, it has been discovered that a formerly unknown relationship unknown exist, between these regions and thus those regions are referred to herein as "reward/ aversion" regions or "reward/aversion circuitry."

Referring to FIGS. 7A–7J, in which like elements are provided having like reference designations throughout the several figures, central nervous system (CNS) activity in reward/aversion circuitry is shown in response to application of thermal stimuli to a subject over varying ranges of temperature. The response may be measured, for example, by using a system such as that to be described below in conjunction with FIG. 11.

Referring now to FIG. 7A, an image of the anterior cingulate gyrus (aCG) having an activation 702 in response to a 41° C. thermal stimulus is shown. The thermal stimulus is delivered to a subject using a Peltier based thermode (manufactured by Medoc, Haifa Israel). The size of the activation shown in FIG. 7A indicates the relative extent within each region. The size of the region corresponds to the amount of activation volume in the aCG. Thus, a relatively small size corresponds to a relatively low activation volume in the aCG while a relatively large size corresponds to a relatively large activation volume in the aCG.

The aCG is known to activate in pain studies bilaterally (i.e. in both the left and right brain hemispheres.) A similar pattern is observed in the insula and the thalamus regions of the CNS. As is known, a conventional two sample Student's T-test will detect a bilateral activation, but will not indicate a temporal sequence of activation in these structures.

FIG. 7B shows a curve 704 representing a thermal stimulus delivered in the form of a series of blocks or thermal pulses 704a–704d. Each of the thermal pulses 704a–704d are provided having a pulse duration typically of about twenty-five seconds followed by a resting period 705 having a duration typically of about thirty seconds and during which time a neutral temperature is applied to the subject. The curve 704 in FIG. 7B, indicates that the thermal stimulus 704 changes from a first temperature during time periods 705 to a second temperature during time periods 704a–704d. In one application, the first temperature corresponds to a neutral temperature (i.e. a temperature which does not cause pain to a subject) and the second temperature corresponds to a temperature which is different from the neutral temperature but which also does not cause significant pain to a subject (referred to as a non-painful temperature). In one experiment, the first temperature (i.e. the neutral temperature) corresponds to a temperature typically of about 35° C. and the second temperature (i.e. the non-painful temperature) corresponds to a temperature typically of about 41° C. Thus, pulses 704a–704d in FIG. 7B vary from a temperature typically of about 35° C. to a temperature typically of about 41° C.

Also shown in the plot of FIG. 7B is a curve 708 which corresponds to a zero baseline signal and a second curve 706 which corresponds to a plot of signal change (in percent) vs. time (in seconds) of a signal in the aCG brain region generated in response to a thermal stimulus (e.g. the thermal pulses 704a–704d) being applied to the subject. The x-axis represents time in seconds over the length of the experiment and the y-axis represents a percentage signal change with reference to the baseline value which is calculated by averaging dimensionless pixel signal values when the stimulus is not present using a technique which is generally known in the art.

It should be appreciated that for each thermal pulse 704a–704d, there is a corresponding positive percentage change in the temporal response as evidenced by regions 706a–706d of curve 706 in the aCG. That is, each time one of the thermal pulses (e.g. one of pulses 704a–704d) is applied to the subject, an increase is measured in the response of the aCG to the thermal pulse as shown by regions 706a–706d in curve 706 in FIG. 7B. As is known, the aCG is part of the reward/aversion circuitry in the brain and since application of one of the thermal pulses 704a–704d elicits a corresponding increase 706a–706d (as measured by percentage signal change) in the aCG response, the aCG is said to be positively valenced with respect to pain. It should be noted that the shape of pulse 706b is an artifact of noise rather than a measure of a biologically relevant feature.

FIG. 7C shows activation in the aCG710 in the CNS reward/aversion region being activated in response to a painful thermal stimulus. The size and color coding used for the activation in FIG. 7A to convey certain information are similarly used to represent information in FIG. 7C.

Importantly, it should be noted, that it is not possible to determine, from the images shown in FIGS. 7A and 7C, an objective marker of pain experience nor to determine which activation map corresponds to the more painful stimulus. That is, while the images in both FIGS. 7A and 7C convey that the subject has activation in a reward/aversion region of the brain (i.e. the aCG), one stimulation was a thermal sensation and the other was a painful one. Yet they both activate the same structure, albeit with different volumes of activation (i.e., there is no differentiation of "warm" non painful from "painful" heat).

Referring now to FIG. 7D a curve 730 represents a thermal stimulus delivered in the form of a series of blocks of thermal pulses 730a–730d, each of the thermal pulses 730a–730d having a pulse duration typically of about twenty-five seconds during which time a relatively high temperature is applied to the subject followed by a resting period 731 having a duration typically of about thirty seconds and during which time a neutral temperature is applied to the subject. The curve 730 in FIG. 7D, indicates that the thermal stimulus 730 changes from a first temperature to a second temperature. In one application, the first temperature corresponds to a neutral temperature (e.g. a temperature typically about 35° C.) and the second application corresponds to a temperature which is different from the neutral temperature (e.g. a temperature typically about 46° C. which corresponds to a relatively painful temperature). Thus, pulses 714a–714d in FIG. 7D change from a temperature typically of about 35° C. to a temperature typically of about 46° C.

Also shown in the plot of FIG. 7D is a first curve 716 which corresponds to a zero baseline signal and a second curve 714 which corresponds to a plot of signal change (in percent) vs. time (in seconds) of a signal in aCG brain region generated in response to the thermal stimulus (e.g. the thermal pulses 730a–730d) being applied to the subject. The x-axis represents time in seconds over the length of the experiment and the y-axis represents a percentage signal change with reference to the baseline value which is calculated by averaging dimensionless pixel signal values when the stimulus is not present using a technique which is generally known in the art.

It should be appreciated that for each thermal pulse 730a–730d, there is a corresponding positive percentage change in the temporal response 714a–714d in the aCG. That is, each time one of the thermal pulses (e.g. one of pulses 730a–730d) is applied to the subject, a corresponding increase is measured in the response of the aCG to the thermal pulse as shown by regions 714a–7146d in curve 714 in FIG. 7D. As is known, the aCG is part of the reward/aversion circuitry in the brain and since application of one of the thermal pulses 730a–730d elicits a corresponding increase 714a–714d (as measured by percentage signal change) in the aCG, the aCG is said to be positively valenced with respect to pain. The decreasing size of the pulse 714c, 714d indicate habituation to repetitive 46 C stimuli for the subject and thus is in agreement with prior art measurements of subjective responses to similar experiments.

As in the case of FIGS. 7A and 7C, it should be noted that it is not possible to objectively determine which waveform 706 or 714 corresponds to the painful stimulus. Additionally it is not possible to objectively detect a level of pain caused by non-painful thermal stimulus 704 and painful thermal stimulus 712 by evaluating waveforms 706 and 714 which are measured in the classic pain center regions. That is, while the curves in both FIGS. 7B and 7D convey that the subject has activation in a reward/aversion region of the brain (i.e. the ACG), it is not possible from the curves of FIGS. 7B and 7D to determine whether the subject felt pain in either case.

Referring now to FIG. 7E, an image of a NAc region 718 of the in response to a 41° C. thermal stimulus is shown. There are no color coded regions in FIG. 7E indicating no response in this reward/aversion region to the non-painful stimulus.

Referring now to FIG. 7F, when the thermal pulses 704a–704d (shown as shaded regions in FIG. 7F) described above in conjunction with FIG. 7B are applied to the subject, a measure of the response in the NAc brain region 718 (FIG. 7E) is plotted as curve 724. As can be seen from FIG. 7F, curve 724 produces no net change from its baseline, and thus can be said to resemble the zero baseline 719. Curve 719 thus indicates that there is no response in the reward/aversion region to the thermal pulse train described 704. Thus, a non-painful stimulus such as the thermal pulse train 704 does not produce any response in the NAc while such a pulse train does produce a response in the aCG.

FIG. 7G shows the NAc in the CNS reward region 726 being activated in response to a painful (i.e. 46° C.) thermal stimulus. The shaded response depicted in FIG. 7G indicates a highly significant statistical activation in the NAc.

Referring now to FIG. 7H, when the thermal pulses 730a–730d (shown as shaded regions in FIG. 7H) described above in conjunction with FIG. 7D are applied to the subject, a measure of the response in the NAc brain region 726 (FIG. 7G) is plotted as curve 734. As can be seen from FIG. 7H, curve 734 fluctuates substantially below a zero baseline 732.

It should be appreciated that for each thermal pulse 730a–730d, there is a corresponding negative percentage change in the temporal response 734 in the NAc. That is, each time one of the thermal pulses (e.g. one of pulses 730a–730d) is applied to the subject, a corresponding decrease is measured in the response of the NAc to the thermal pulse as shown by regions 734a–734d in curve 734 in FIG. 7H. As described herein above in accordance with the present invention, the NAc is part of the reward/aversion circuitry and since application of one of the thermal pulses 730a–730d elicits a corresponding decrease 734a–734d (as measured by percentage signal change) in the NAc, the NAc is said to be negatively valenced with respect to pain.

Thus, while it is not possible to distinguish a painful thermal stimulus from a non-painful thermal stimulus by simply using measurements from a reward/aversion region such as the aCG, it is possible to distinguish a painful thermal stimulus from a non-painful thermal stimulus by examining the response from two reward/aversion regions such as the aCG and the NAc. Specifically, the aCG responses 702, 706 (FIGS. 7A, 7B respectively) and 710, 714 (FIGS. 7C and 7D respectively) do not contain enough information to allow one to distinguish a painful stimulus from a non-painful stimulus by examination (i.e. it does not provide an objective determination that a subject is actually experiencing pain). However, by examining the responses from both the aCG and the NAc, it is possible to distinguish the painful stimulus from the non-painful stimulus due to the different responses 719, 734 (FIGS. 7F, 7H, respectively) which appear in the NAc.

For each pulse 730a–730d representing an increase in temperature to 46° C. in the thermal stimulus, there is a corresponding negative percentage change in the temporal response 734a–734d in the NAc. 734c may reflect an adaptation of the BOLD response. As shown above, activation information from only the reward/aversion region, signal 714, does not provide enough data to make an objective characterization of the brain activity. However, combining information derived from the correlation of the negative response waveform 734 representing the NAc with signal 714, allows an objective determination that the subject is actually experiencing pain produced by the high temperature (46° C.) thermal stimulus.

Figure 7I:
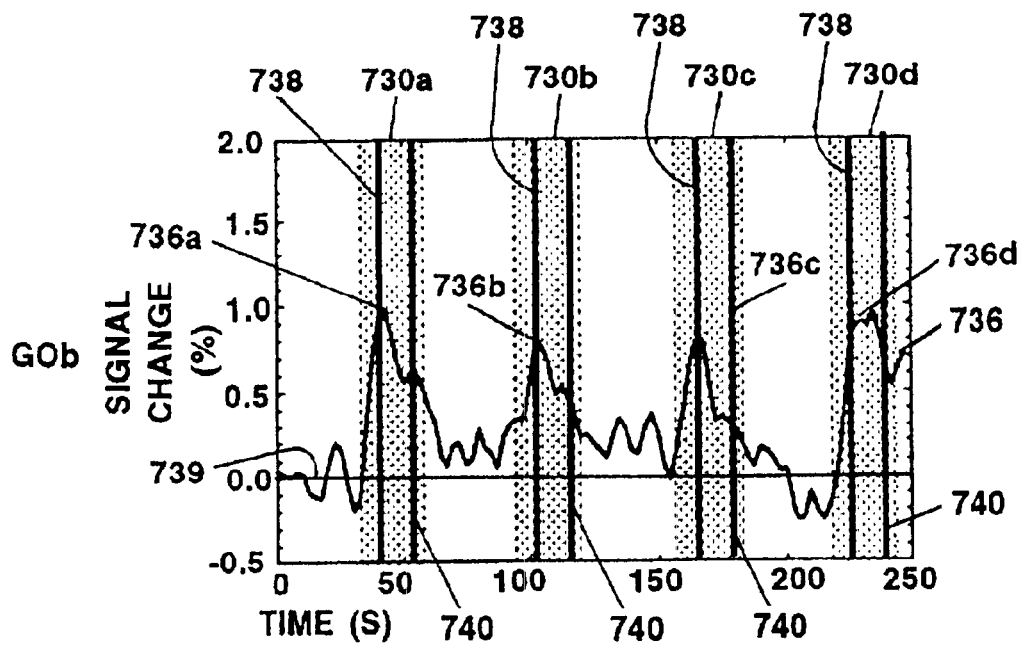
FIG. 7I is a plot of signal change vs. time of a signal in the Gob brain region in response to a painful thermal stimulus.

Referring now to FIG. 7I, a curve 736 of the GOb region of the brain representing the response to a series of thermal pulses 730a, 730d followed by periods of neutral temperature is shown. As described above, the GOb is another brain region implicated in reward/aversion. Curve 739 represents a zero baseline signal. Curve 736 is plotted as percent signal change vs. time (seconds). Vertical time lines 738 indicate the peak of early activation phase for thermal stimuli pulses 730a–730d and vertical time lines 740 indicate the peak of late activation phase for thermal stimuli pulses 730a–730d.

Figure 7J:
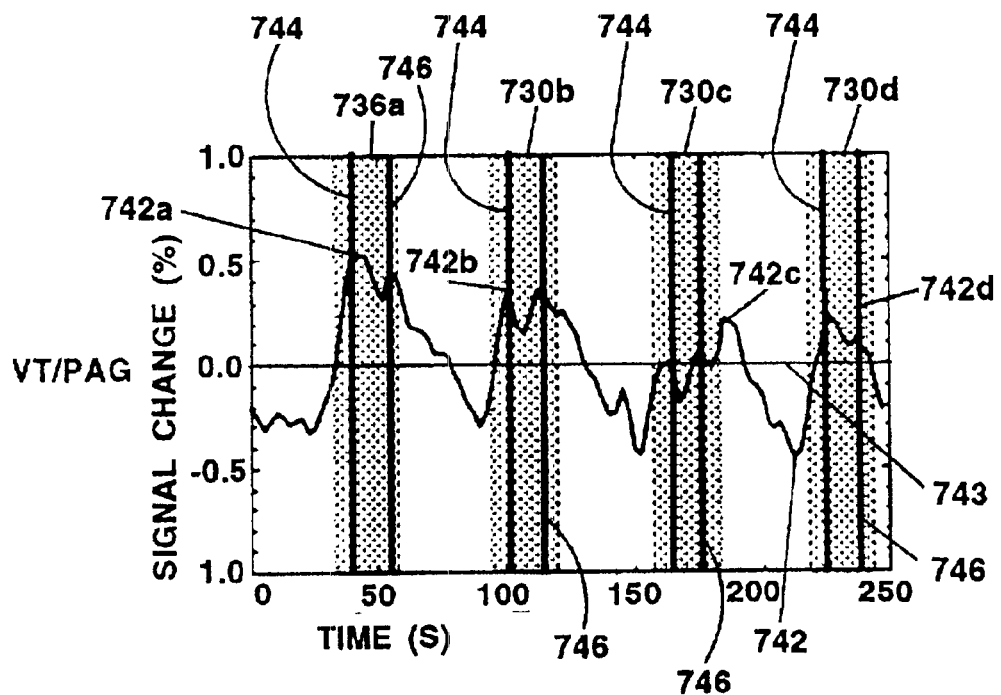
FIG. 7J is a plot of signal change vs. time of a signal in the VT/PAG brain region in response to a painful thermal stimulus.

For each pulse 730a–730d representing an increase in temperature to 46° C. in the thermal stimulus, there is a corresponding positive percentage change in the temporal response 736a–736d in the GOb Referring now to FIG. 7J, a curve 742 of the VT/PAG region of the brain representing the response to a series of thermal pulses 730a–730d followed by periods of neutral temperature is shown. As described above, the VT/PAG region is another brain region implicated in reward/aversion function. Curve 743 represents a zero baseline signal. Curve 742 is plotted as percent signal change vs. time (seconds). Vertical time lines 744 indicate the peak of early activation phase for thermal stimuli pulses 730a–730d and vertical time lines 746 indicate the peak of late activation phase for thermal stimuli pulses 730a–730d.

For each pulse 730a–730d representing an increase in temperature to 46° C. in the thermal stimulus, there is a corresponding positive percentage change in the temporal response 742a–742d in the VT/PAG region. As shown above, activation information from only the classic pain regions, (e.g. signals 706, 714 in FIGS. 7B, 7D respectively), does not provide an objective determination that a subject is actually experiencing pain from the above-described experiment. However as will be described in further detail below, by combining information derived from pain and other regions which are part of the reward/aversion circuitry an objective determination that the subject is actually experiencing pain produced by the high temperature (46° C.) thermal stimulus can be made.

It should be noted that there is a large initial change in the signal 742 during the first epoch 730a of the thermal stimulus and not during subsequent thermal epochs 730b–730d. Habituation reflects adaptation of the reward/aversion system to repeated and/or controlling aversive stimulation. The decreasing size of pulses 742a–742d indicates an adaptation of the brain response.

Referring to FIGS. 8A–8D, in which like elements are provided having like reference designations throughout the several figures, central nervous system (CNS) activity in is shown in response to application of heat as a 41° C. stimulus to a subject sensitized to heat by capsaicin to produce a model of sensitization/hyperalgesia (Pain 2). The response may be measured, for example, by using a system such as that to be described below in conjunction with FIG. 11.

Figure 8D:
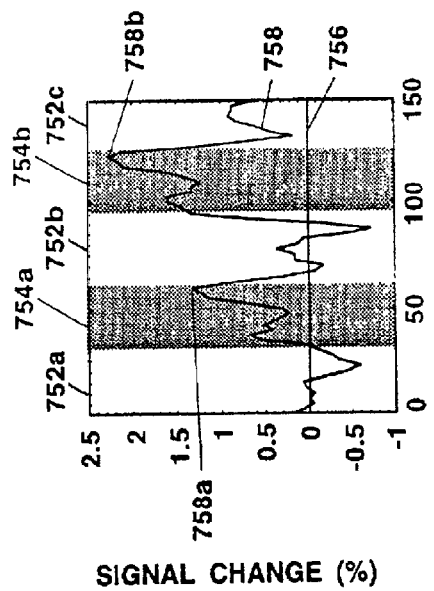
FIG. 8D is a plot of signal change vs. time of a signal in NAc brain region in response to a thermal stimulus and an application of capsaicin.
Figure 8B:
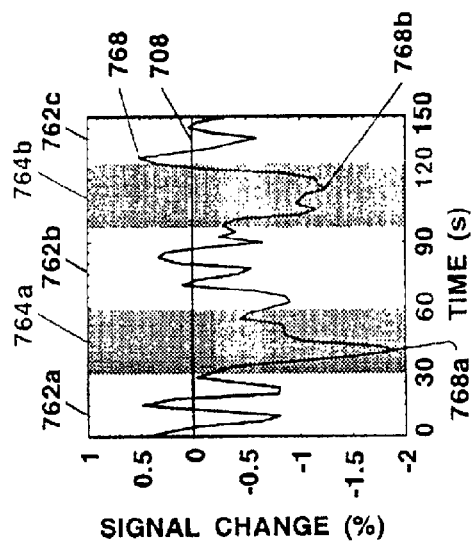
FIG. 8B is a plot of signal change vs. time of a signal in aCG brain region in response to a thermal stimulus and an application of capsaicin.
Figure 8C:
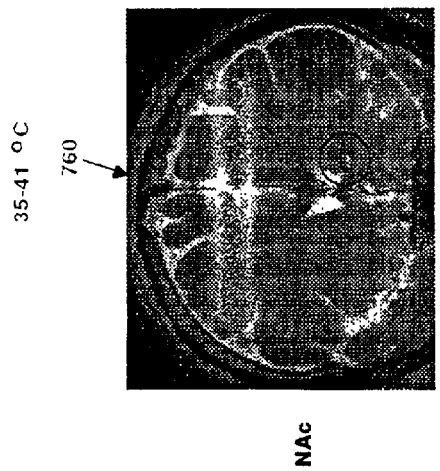
FIG. 8C is a diagram of a portion of a brain showing activation of the NAc brain region in response to a thermal stimulus and an application of capsaicin.
Figure 8A:
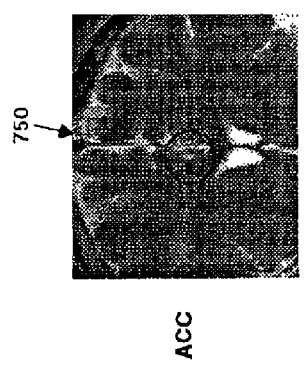
FIG. 8A is a diagram of a portion of a brain showing activation of the aCG brain region in response to a thermal stimulus and an application of capsaicin.

Referring now to FIG. 8A, an image of an anterior cingulate gyrus (aCG) having an activation 750 in response to a 41° C. thermal stimulus is shown. The thermal stimulus is delivered to a subject using a Peltier based thermode. It should be appreciated of course that any thermal mechanical, chemical device can be used to produce pain. The size and shading of the aversion shown in FIG. 8A indicate the relative extent and statistical significance respectively within each region. The size of the region corresponds to the amount of activation in a volume in the aCG. Thus, a relatively small size corresponds to a relatively low activation volume in the aCG while a relatively large size corresponds to a relatively large activation volume in the aCG. Also, a region having a darker shading indicates a less significant activation while a region having a lighter shading indicates a more significant activation. Other models of sensitization produced thermal, mechanical, chemical stimuli could be used, for example prolonged hot thermal stimulus or mustard oil or any stimulus well known to those of ordinary skill in the art into the subject to produced by hyperalgesia could be used.

The aCG is known to activate in pain studies bilaterally. A similar pattern is observed in the insula and the thalamus regions of the CNS. As is known, a conventional two sample Student's T-test will detect a bilateral activation, but will not indicate a temporal correlation with other regions.

FIG. 8B shows a series of unshaded regions 752 and shaded regions 754 representing a resting period and a thermal stimulus respectively delivered in the form of a series of blocks or thermal pulses. The thermal pulses 754a–754b are provided having a pulse duration typically of about thirty seconds followed by a resting period 752b and 752c having a duration typically of about thirty seconds and during which time a neutral temperature is applied to the subject. In one application, the resting temperature corresponds to a neutral temperature (i.e. a temperature which does not cause pain to a subject) and the second application corresponds to a temperature which is different from the neutral temperature but which also does not cause significant pain to a subject (referred to as a non-painful temperature). In one experiment, the first temperature (i.e. the neutral temperature) corresponds to a temperature typically of about 35° C. and the second temperature (i.e. the non-painful temperature) corresponds to a temperature typically of about 41° C. Thus, pulses 752 and 754 in FIG. 8B vary from a temperature typically of about 35° C. to a temperature typically of about 41° C.

Also shown in the plot of FIG. 8B is a curve 756 which corresponds to a zero baseline signal and a second curve 758 which corresponds to a plot of signal change (in percent) vs. time (in seconds) of a signal in the aCG brain region generated in response to a thermal stimulus (e.g. the thermal pulses 752 and 754) being applied to the subject. The x-axis represents time in seconds over the length of the experiment and the y-axis represents a percentage signal change with reference to the baseline value which is calculated by averaging dimensionless pixel signal values when the stimulus is not present using a technique which is generally known in the art.

It should be appreciated that for each thermal pulse 752 and 754, there is a corresponding positive percentage change in the temporal response as evidenced by regions 758a–758b of curve 758 in the aCG. That is, each time one of the thermal pulses (e.g. one of pulses 752 and 754) is applied to the subject, an increase is measured in the response of the aCG to the thermal pulse as shown by regions 758a–758b in curve 758 in FIG. 8B. As is known, the aCG is part of the reward/aversion circuitry in the brain and since application of one of the thermal pulses 752 and 754 elicits a corresponding increase 758a–758b (as measured by percentage signal change) in the aCG response, the aCG is said to be positively valenced with respect to pain.

Referring now to FIG. 8C, an image of aNAc region 760 in response to a 41° C. thermal stimulus is shown. The thermal stimulus is delivered to a subject using a thermal stimuli. The size and color of the activations shown in FIG. 8C indicate the relative activation and statistical significance respectively within each region. The size of the region corresponds to the amount of activation volume in the NAc. Thus, a relatively small size corresponds to a relatively low activation in a volume in the NAc while a relatively large size corresponds to a relatively large activation volume in the NAc.

FIG. 8D shows a series of unshaded regions 762 and shaded regions 764 representing a resting period and a thermal stimulus respectively delivered in the form of a series of blocks or thermal pulses. Each of the thermal pulses 764a–764b are provided having a pulse duration typically of about twenty five seconds followed by a resting period 762b and 762c having a duration typically of about thirty seconds and during which time a neutral temperature is applied to the subject. In one application, the resting temperature corresponds to a neutral temperature (i.e. a temperature which does not cause pain to a subject) and the second application corresponds to a temperature which is different from the neutral temperature but which also does not cause significant pain to a subject (referred to as a non-painful temperature). In one experiment, the first temperature (i.e. the neutral temperature) corresponds to a temperature typically of about 35° C. and the second temperature (i.e. the non-painful temperature) corresponds to a temperature typically of about 41° C. Thus, pulses 762 and 764 in FIG. 8D vary from a temperature typically of about 35° C. to a temperature typically of about 41° C.

Also shown in the plot of FIG. 8D is a curve 766 which corresponds to a zero baseline signal and a second curve 768 which corresponds to a plot of signal change (in percent) vs. time (in seconds) of a signal in aCG brain region generated in response to a thermal stimulus (e.g. the thermal pulses 762 and 764) being applied to the subject. The x-axis represents time in seconds over the length of the experiment and the y-axis represents a percentage signal change with reference to the baseline value which is calculated by averaging dimensionless pixel signal values when the stimulus is not present using a technique which is generally known in the art.

It should be appreciated that for each thermal pulse 762 and 764, there is a corresponding negative percentage change in the temporal response as evidenced by regions 768a–768b of curve 768 in the NAc. That is, each time one of the thermal pulses (e.g. one of pulses 762 and 764) is applied to the subject, a decrease is measured in the response of the NAc to the thermal pulse as shown by regions 768a–768b in curve 768 in FIG. 8D. As is known, the NAc is part of the reward/aversion circuitry in the brain and since application of one of the thermal pulses 762 and 764 elicits a corresponding decrease 768a–768b (as measured by percentage signal change) in the NAc response, the NAc is said to be negatively valenced with respect to pain. It should be appreciated that cold temperatures (in addition to hot temperatures) can be used to induce pain.

Figure 9B:
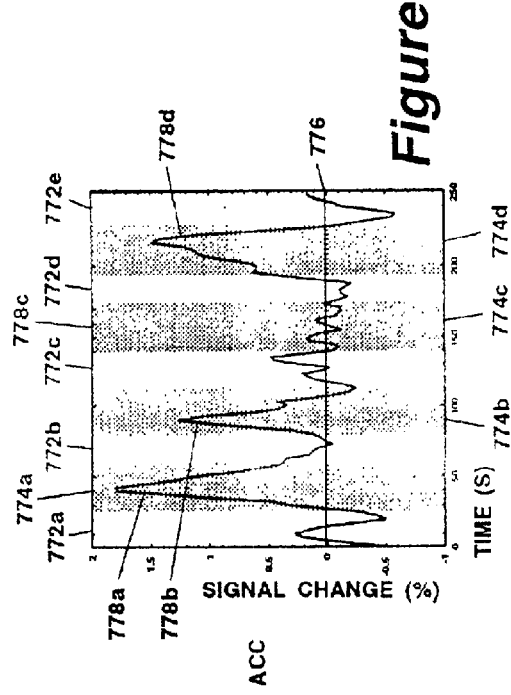
FIG. 9B is a plot of signal change vs. time of a signal in aCG brain region of a subject with neuropathic pain in response to a thermal stimulus.
Figure 9C:
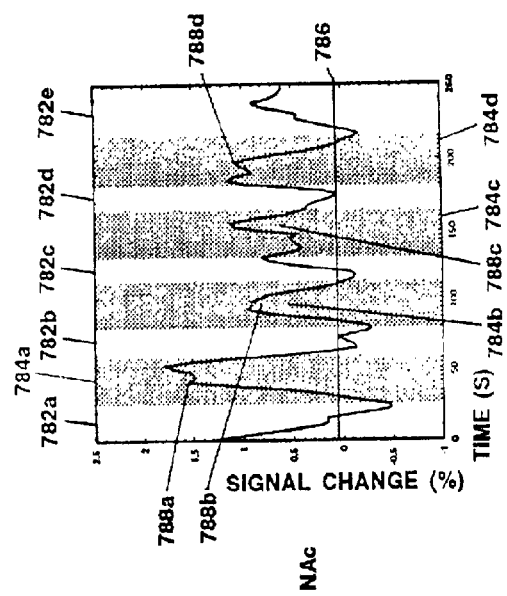
FIG. 9C is a plot of signal change vs. time of a signal in NAc brain region of a subject with neuropathic pain in response to a thermal stimulus.
Figure 9A:
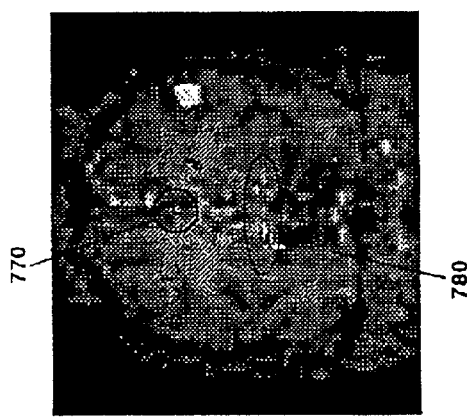
FIG. 9A is a diagram of a portion of a brain showing activation of the aCG and NAc brain regions of a subject with neuropathic pain in response to a thermal stimulus.

Referring to FIGS. 9A–9C, in which like elements are provided having like reference designations throughout the several figures, central nervous system (CNS) activity in reward/aversion circuitry is shown in response to application of a mechanical stimulus (brush) by hand at a rate of about 2 strokes per second stimulus to an area in which a subject has neuropathic pain to produce a model of chronic pain (Pain 3). It should be appreciated that other mechanical stimulus may also be used, and static or dynamic mechanical stimuli may be used. The response may be measured, for example, by using a system such as that to be described below in conjunction with FIG. 11A.

Referring now to FIG. 9A, an image of an anterior cingulate gyrus (aCG) having an activation 770 in response to the brush stimulus is shown. The size of the activation shown in FIG. 9A indicate the relative extent within each region. The size of the region corresponds to the amount of activation in a volume in the aCG. Thus, a relatively small size corresponds to a relatively low activation volume in the aCG while a relatively large size corresponds to a relatively large activation volume in the aCG.

The aCG is known to activate in pain studies bilaterally. A similar pattern is observed in the insula and the thalamus regions of the CNS. As is known, a conventional two sample Student's T test will detect a bilateral activation, but will not indicate a temporal sequence of activation in these regions.

FIG. 9B shows a series of unshaded regions 772 and shaded regions 774 representing a resting period and a brush stimulus respectively delivered in the form of a series of blocks. Each of the brush pulses 774a–774b are provided having a pulse duration typically of about twenty five seconds followed by a resting period 772b and 772c having a duration typically of about thirty seconds and during which time no brush stimulus is applied to the subject. Also shown in the plot of FIG. 9B is a curve 776 which corresponds to a zero baseline signal and a second curve 778 which corresponds to a plot of signal change (in percent) vs. time (in seconds) of a signal in the aCG brain region generated in response to a brush stimulus being applied to the subject. The x-axis represents time in seconds over the length of the experiment and the y-axis represents a percentage signal change with reference to the baseline value which is calculated by averaging dimensionless pixel signal values when the stimulus is not present using a technique which is generally known in the art.

It should be appreciated that for each brush pulses 772 and 774, there is a corresponding positive percentage change in the temporal response as evidenced by regions 778a–778d of curve 778 in the aCG. That is, each time one of the brush pulses (e.g. one of pulses 772 and 774) is applied to the subject, an increase is measured in the response of the aCG to the brush pulse as shown by regions 778a–778d in curve 778 in FIG. 9B. As is known, the aCG is part of the reward/aversion in the brain and since application of one of the brush pulses 772 and 774 elicits a corresponding increase 778a–778d (as measured by percentage signal change) in the aCG response, the aCG is said to be positively valenced with respect to pain.

Referring again to FIG. 9A, an image of aNAc region 780 in response to a 41° C. mechanical stimulus is shown. The mechanical stimulus is delivered to a subject using a mechanical stimulus (e.g., applied by hand or a specialized delivery unit). The size and color of the activations shown in FIG. 9A indicate the relative extent and statistical significance respectively within each region. The size of the region corresponds to the amount of activation volume in the NAc. Thus, a relatively small size corresponds to a relatively low activation volume in the NAc while a relatively large size corresponds to a relatively large activation volume in the NAc.

FIG. 9C shows a series of unshaded regions 782 and shaded regions 784 representing a resting period and a brush stimulus respectively delivered in the form of a series of blocks. Each of the brush pulses 784a–784b are provided having a pulse duration typically of about twenty five seconds followed by a resting periods 782b–e having a duration typically of about thirty seconds and during which time no brush stimulus is applied to the subject.

Also shown in the plot of FIG. 9C is a curve 786 which corresponds to a zero baseline signal and a second curve 788 which corresponds to a plot of signal change (in percent) vs. time (in seconds) of a signal in aCG brain region generated in response to a brush stimulus being applied to the subject. The x-axis represents time in seconds over the length of the experiment and the y-axis represents a percentage signal change with reference to the baseline value which is calculated by averaging dimensionless pixel signal values when the stimulus is not present using a technique which is generally known in the art.

It should be appreciated that for each mechanical stimulus 784, there is a corresponding positive percentage change in the temporal response as evidenced by regions 788a–788d of curve 788 in the NAc. That is, each time one of the brush pulses (e.g. one of pulses 782 and 784) is applied to the subject, an increase is measured in the response of the NAc to the thermal pulse as shown by regions 788a–788d in curve 788 in FIG. 9C. As is known, the NAc is part of the reward/aversion circuitry in the brain and since application of one of the thermal pulses 782 and 784 elicits a corresponding increase 788a–788d (as measured by percentage signal change) in the NAc response, the NAc is said to be positively valenced with respect to pain of the category of pain 3.

Note that both the NAc and aCG are activated positively, in this pain 3 study, unlike the pattern of NAc and aCG activation for pain 1 studies illustrated in FIGS. 7 and 8.

Referring to FIGS. 10A–10D, in which like elements are provided having like reference designations throughout the several figures, central nervous system (CNS) activity in reward/aversions is shown in response to application of heat as a 46° C. stimulus and either saline or morphine is administered to a subject to measure an analgesic effect. The response may be measured, for example, by using a system such as that to be described below in conjunction with FIG. 11. In the x-axis of FIGS. 10B, 10D, the image number corresponds to four cardiac pulses.

Figure 10B:
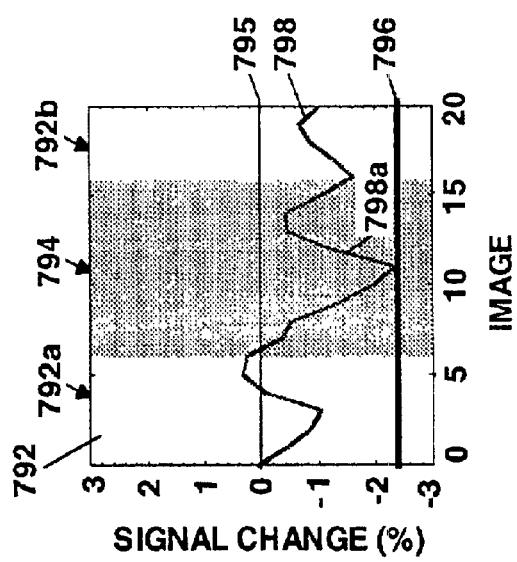
FIG. 10B is a plot of signal change vs. time of a signal in NAc brain region in response to a painful thermal stimulus and an intravenous infusion of saline.
Figure 10D:
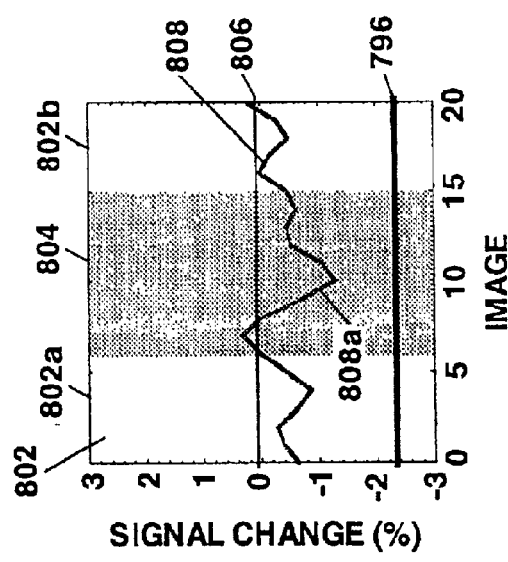
FIG. 10D is a plot of signal change vs. time of a signal in NAc brain region in response to a painful thermal stimulus and an intravenous infusion of morphine.
Figure 10A:
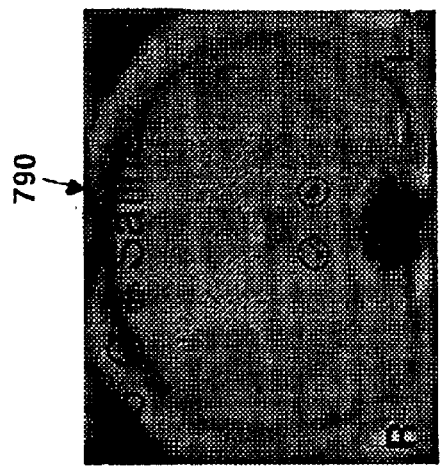
FIG. 10A is a diagram of a portion of a brain showing activation of the NAc brain region in response to a painful thermal stimulus and an infusion of saline.

Referring now to FIG. 10A, an image of the NAc having an activation 790 in response to a 46° C. thermal stimulus in a subject who has been administered intravenous saline is shown. The saline is administered using conventional intravenous techniques. The thermal stimulus is delivered to a subject using a Peltier based thermode. The size of the activations shown in FIG. 10A indicate the relative extent within each region. The size of the region corresponds to the amount of activation in a volume in the NAc. Thus, a relatively small size corresponds to a relatively low activation volume in the NAc while a relatively large size corresponds to a relatively large activation volume in the NAc.

FIG. 10B shows a series of unshaded regions 792a and 792b and a shaded region 794 representing a resting period and a thermal stimulus respectively delivered in the form of a series of blocks or thermal pulses. The thermal pulse 794 is provided having a pulse duration typically of about thirty seconds followed by a resting period 792b having a duration typically of about thirty seconds and during which time a neutral temperature is applied to the subject. In one application, the resting temperature corresponds to a neutral temperature (i.e. a temperature which does not cause significant pain to a subject) and the second application corresponds to a temperature which is different from the neutral temperature and causes pain to a subject (referred to as a painful temperature). In one experiment, the first temperature (i.e. the neutral temperature) corresponds to a temperature typically of about 35° C. and the second temperature (i.e. the painful temperature) corresponds to a temperature typically of about 46° C. Thus, pulses 792 and 794 in FIG. 10B vary from a temperature typically of about 35° C. to a temperature typically of about 46° C.

Also shown in the plot of FIG. 10B is a curve 796 which corresponds to a maximum percentage signal change and a second curve 798 which corresponds to a plot of signal change (in percent) vs. time (in seconds) of a signal in NAc brain region generated in response to a thermal stimulus (e.g. the thermal pulses 792 and 794) being applied to a subject infused with saline. The x-axis represents an image number instead of time (because data is cardiac gated) over the length of the experiment and the y-axis represents a percentage signal change with reference to a zero value which is calculated by averaging dimensionless pixel signal values when the stimulus is not present using a technique which is generally known in the art.

It should be appreciated that for the thermal pulse 792 and 794, there is a corresponding negative percentage change in the temporal response as evidenced by region 798a of curve 798 in the NAc. That is, when the thermal pulse 792 and 794 is applied to the subject, a percentage decrease is measured in the response of the NAc to the thermal pulse as shown by regions 798a in curve 798 in FIG. 10B. As is known, the NAc is part of the reward/aversion reward/aversion in the brain and since application the thermal pulse 792 and 794 elicits a corresponding decrease 798a (as measured by percentage signal change) in the NAc response, the NAc is said to be negatively valenced with respect to pain. When compared to the results in FIG. 7H, prior saline infusion has no effect on the negatively valenced signal in the NAc following the 46° C. stimulus. Note the similar pattern of decreased activation after noxious heat alone as show in FIG. 7H. By comparing curve 798 to curve 808 it can be observed that injection of morphine attenuates the response thus the curves 798, 808 correspond to an objective measure of the drug on pain.

Figure 10C:
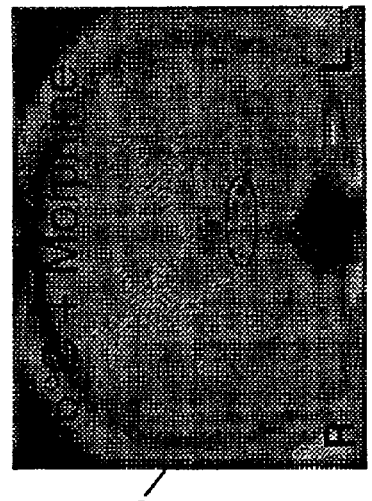
FIG. 10C is a diagram of a portion of a brain showing activation of the NAc brain region in response to a painful thermal stimulus and an intravenous infusion of morphine.

Referring now to FIG. 10C, an image of an NAc region 800 in response to a 46° C. thermal stimulus being applied to a subject infused with morphine is shown. The thermal stimulus is delivered to a subject using a Peltier based thermode. The morphine dose was 4 mg/70 kg. The size and shading of the activations shown in FIG. 10C indicate the relative extent and statistical significance respectively within each region. The size of the shaded region corresponds to the amount of activation volume in the NAc. Thus, a relatively small size corresponds to a relatively low activation volume in the NAc while a relatively large size corresponds to a relatively high activation volume in the NAc. Also, a region having a darker shading indicates a less significant activation while a region having a lighter shading indicates a more significant activation.

FIG. 10D shows a series of unshaded regions 802 and a shaded region 804 representing a resting period and a thermal stimulus respectively delivered in the form of a series of blocks of thermal pulses. The thermal pulses 804 is provided having a pulse duration typically of about twenty five seconds followed by a resting period 802b having a duration typically of about thirty seconds and during which time a neutral temperature is applied to the subject. In one application, the resting temperature corresponds to a neutral temperature (i.e. a temperature which does not cause pain to a subject) and the second application corresponds to a temperature which is different from the neutral temperature and causes pain to a subject (referred to as a painful temperature). In one experiment, the first temperature (i.e. the neutral temperature) corresponds to a temperature typically of about 35° C. and the second temperature (i.e. the painful temperature) corresponds to a temperature typically of about 46° C. Thus, pulses 802 and 804 in FIG. 10D vary from a temperature typically of about 35° C. to a temperature typically of about 46° C.

Also shown in the plot of FIG. 10D is a curve which corresponds to the maximum percentage signal change 796 (FIG. 10B) and a second curve 808 which corresponds to a plot of signal change (in percent) vs. time (in seconds) of a signal in NAc brain region generated in response to a thermal stimulus (e.g. the thermal pulses 802 and 804) being applied to the subject. Curve 796 is provided as a means to compare signals 808 and 798 (FIG. 10B). The x-axis represents an image number instead of time (because data is cardiac gated) over the length of the experiment and the y-axis represents a percentage signal change with reference to a zero value which is calculated by averaging dimensionless pixel signal values when the stimulus is not present using a technique which is generally known in the art.

It should be appreciated that for the thermal pulse 802 and 804, there is a greatly reduced negative percentage change in the temporal response as evidenced by region 808a of curve 808 in the NAc. That is, each time one of the thermal pulses (e.g. one of pulses 804) is applied to the subject, a decrease is measured in the response of the NAc to the thermal pulse as shown by regions 808a–b in curve 808 in FIG. 10D. Note that the magnitude of signal decrease (~1%) is much less than the decrease produced by heat plus saline (2%, as indicated by curve 798). As is known, the NAc is part of the reward/aversion in the brain and since application of one of the thermal pulses 802 and 804 elicits a corresponding decrease 808a (as measured by percentage signal change) in the NAc response, the NAc is said to be negatively valenced with respect to pain By examining the responses from the NAC and the results from the Pain 1 experiments (FIGS. 7A–7H), it is possible to objectively determine the effect of the saline and the morphine on a painful stimulus. It can be objectively determined that morphine at an example dose of 4 mg/70 kg attenuates pain by measuring decrease in activation produced by noxious heat (46° C.) in the NAc in the subject.

This alteration of the signal by an analgesic drug morphine, but not by a placebo control, indicates this method may be used to evaluate drugs with potential analgesic effects, or more general drugs with effects on reward/aversion circuitry that may be used to treat pain, vs. long-term sequelae of pain. Similar techniques may also be used to evaluate drug effects in functional illnesses mediated by altered functions in these reward/aversion brain regions.

Referring to FIGS. 10E and 10F, central nervous system (CNS) activity in reward/aversive regions is shown in response to an infusion of naloxone (in a dose of 4 mg/70 kg) in a subject. The response may be measured, for example, by using a system such as that to be described below in conjunction with FIG. 11.

Referring now to FIG. 10E, the VT/PAG (combined left and right components in region 820) having an activation 820 in response to an infusion of naloxone in a subject. The size and shade of the region 420a indicates the extent of activation and statistical significance respectively within the region. Thus, a relatively small size corresponds to a relatively low activation in a volume in the VT/PAG while a relatively large size corresponds to a relatively larger volume in the VT/PAG. In region 820, a darker shade of gray indicates a less significant activation while a region indicated by a lighter shade of gray indicates a more significant activation.

FIG. 10F shows an unshaded region and a shaded region representing a preinfusion period 822a of naloxone and a period during which naloxone is being infused 822b. The period 822a has a duration typically of about five minutes followed by the infusion period 822b having a duration typically of about five minutes.

The response is represented by curve 828 showing pre-infusion (white background) and post-infusion (stippled background) time points. The x-axis represents time over the length of the experiment and the y-axis represents a percentage signal change with reference to a zero value which is calculated by averaging dimensionless pixel signal values before the infusion using a technique which is generally known in the art.

It should be appreciated that for the infusion period 822b, there is a corresponding negative percent change in the temporal response as evidenced by curve 828 in the VT/PAG. As is known, the VT/PAG is part of the reward/aversion circuitry in the brain and since infusion of naloxone elicits a corresponding decrease (as measured by percentage signal change) in the VT/PAG response, the VT/PAG is said to be negatively valenced with respect to a drug that affects pain function, and analgesic responses to pain.

Figure 11:
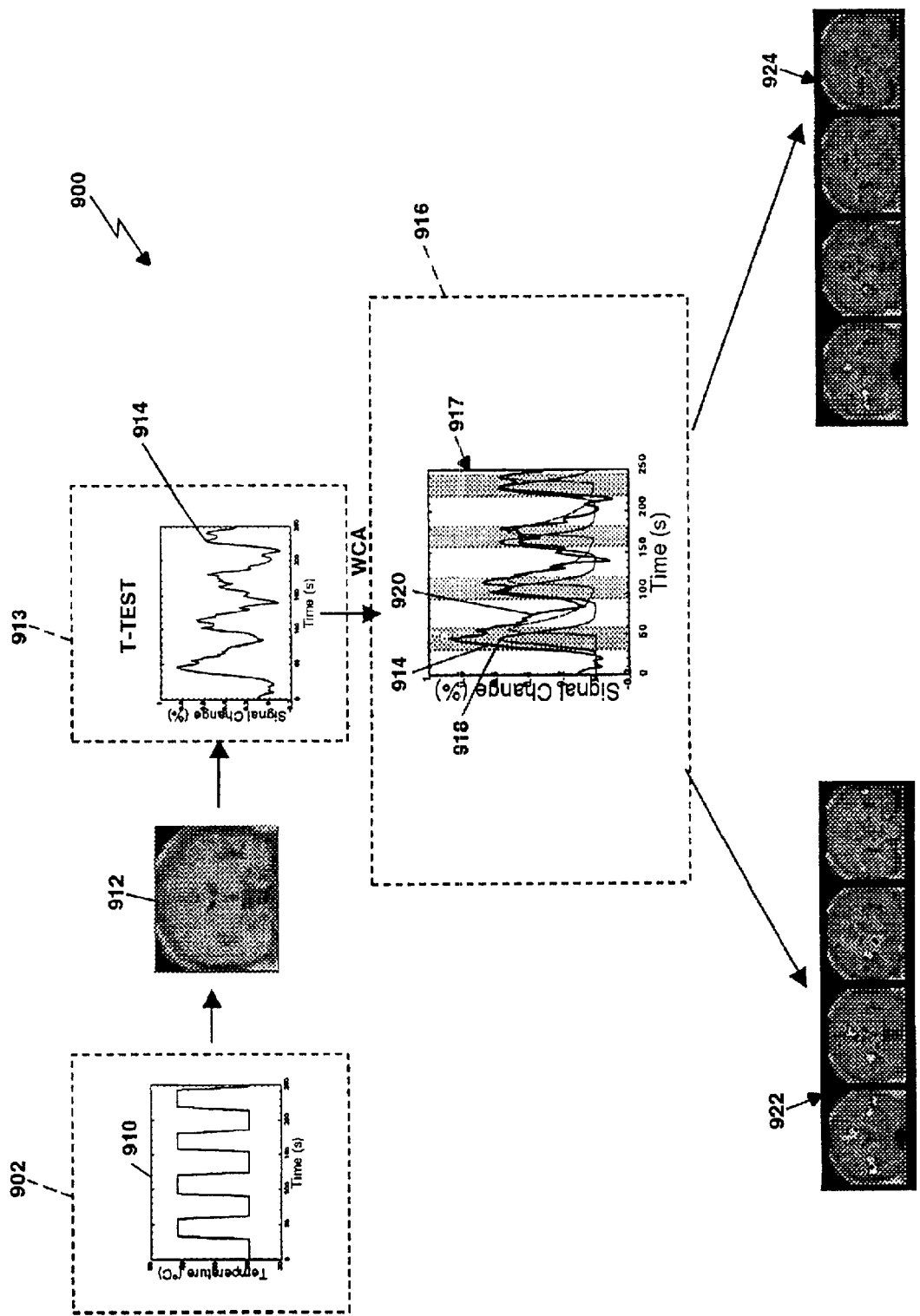
FIG. 11 is a diagram of a system for determining central nervous system activity in reward/aversion circuitry.

Now referring to FIG. 11, a system 900 for determining central nervous system (CNS) activity in the reward/aversion circuitry over time in response to varying temperature ranges of noxious thermal stimuli includes means for delivering a noxious thermal stimulus 902 to a subject (not shown) having a central nervous system (CNS) 912.

A measurement system 913 is disposed about the subject to non-invasively measure one or more signals produced by the CNS 912 in response to the thermal stimulus. The system 913 also produces a statistical activation map by any number of methods including but not limited to applying a so-called Student's T-test and using the results of the T-test to obtain a mean hemodynamic response (MHR), represented as curve 914 for a subset of active pixels found using the T-test. The x axis represents time in seconds over the length of the experiment. The y axis represent a percentage signal change with reference to a baseline value which is calculated be averaging dimensionless pixel signal values when the stimulus is not present. The curve 914 corresponds to the sum of all responses in the brain detected by the T-test.

A waveform-based correlation analysis WCA processor 916 is coupled to receive the MHR values from the system 913. The WCA processor 916 processes the MHR values 914 to decompose the values which form curve 914 to provide a pair of temporal components 918 and 920 of the MHR values. It will be appreciated by those of ordinary skill in the art that the MHR can be decomposed into multiple phases. In general the number of components is a characteristic of the brain response to the motivational salient stimulus. For example, the experiment described in conjunction with FIG. 7 produces activity in reward/aversion circuitry, and the MHR can be decomposed into two components. WCA processor thus decomposes the MHR values into an early phase 918 and a late phase 920. The early phase 918 generally represents the reward and motivation/emotional response, and the late phase 920 generally represents the pain and sensory responses. Once the early and late phase components 918, 920 are provided, the system 900 correlates the brain response in selected regions with the early and late phase components 918, 920 on a pixel by pixel basis to produce activation maps in the motivation/emotional/reward circuitry 922 and sensory/pain circuitry 924. However, if more regions were implicated in the response, then it may be desirable to decompose the signal into still more components.

In one application, means 902 provides the noxious thermal stimulus to a subject (not shown) in a predetermined pattern selected to elicit a predetermined response from the subject exposed to the stimulus. In this particular example, the noxious thermal stimulus is delivered in a block design of twenty-five seconds of a relatively high temperature (i.e. thermal stimulus "on") followed by thirty seconds of neutral temperature (i.e. thermal stimulus "off") as represented by curve 910. The block waveform indicates the noxious thermal stimulus 910 changing from a first temperature to a second higher temperature. In one specific embodiment, the first temperature corresponds to a lower neutral temperature (e.g. a temperature of about 35° C.) and the second temperature corresponds to a higher noxious temperature (e.g. a temperature of about 46° C.). The thermal stimulus produces activity measured by system 913 as a neuroimaging signal in the CNS 912. An analysis applied to fMRI images produces data that are motion corrected, intensity normalized, and talairach transformed. The T-test produces a statistical activation map. Conventionally, after the activation regions were identified by T-test analysis, analysis of the imaged signals was concluded.

The analysis of the imaged signals is continued in the present invention by obtaining the mean hemodynamic response (MHR) curve 914 for a subset of active pixels found using the T-test. Waveform analysis is then evaluated and gamma curves fitted to these signals.

Several functions have been proposed to model hemodynamic response (in this case the MHR). In one embodiment, gamma functions as expressed in Equation (1) below can be used with an added delay to account for different thermal stimulus delivery times.

$$Y = a + b*(t-c)^{d} * e^{-(t-c)/e} \qquad \text{Equation (1)}$$

In which:
  a is an offset correction parameter;
  b is a measure of the amplitude of the hemodynamic response;
  c is a time delay; and
  d and e determine the time to peak and width of the hemodynamic response.

It should be appreciated, however, that other functions such as gaussian and poison can be used to do the fit.

In the thermal study described above in conjunction with FIGS. 7A–7J, four thermal stimuli are delivered for each experiment and it was assumed that the gamma functions across the four stimuli would have the same width and amplitude, but start at different times. It should be noted, however, that an analysis in which the amplitude is also variable and adjusted for each stimulus can be performed. Hence the values b, d, and e were optimized for the four responses, while the parameter c was adjusted for each response. A least-squares approach was used to fit the gamma functions. It should appreciated, however, that the values b, d, and c can be adjusted for each response.

Two sets of gamma functions which were used to model the MHR were obtained and statistical maps for each set, representing the early and late phases respectively, were generated in a similar fashion as the WCA method, i.e., using each set of fitted gamma functions (labeled as early and late phases) as the MHR to calculate Pearson moment correlation coefficients on a voxel-by-voxel manner. In order to improve statistics and to reduce bias in the calculation due to the simultaneous presence of both phases in certain structures, the time courses of all pixels were selectively blocked. Thus, in analyzing the early phase, for example, time points corresponding to the late phase were not included, and vice versa. Time points were blocked between the time of intersection of both hemodynamic models to time points in which the undesired hemodynamic model dropped to amplitudes less than 10% of the maximum amplitude. Final adjustments in the number of time points were made so that each phase had the same number of residual time points.

It should be appreciated, however, that other methods can be used to account for the overlap of phases, such as subtraction methods.

The WCA processor 913 analysis provides time course data from the MHR signal data 914 by decomposing the MHR signal data 914 into two temporal signal components represented by curves 918, 920. Plot 917 shows curves 918 and 920 temporally aligned and superimposed with the MHR curve 914. For the thermal pain experiment curve 918 represents an early phase activation signal correlated with activations in some reward/aversion regions and not others. In contrast to curve 918, these regions all respond before subjects report strong subjective effects of the aversive stimulus. Curve 920 represents the late phase activation signal correlated with activations in distinct reward/aversion regions along with sensory regions that produce signal changes temporally correlated with the subject ratings of pain. WCA analysis thus allows the dissection of early information processing systems from conscious sensory processing systems because of the temporal alignment of the early and late phase activation signals 918, 920. This pattern of regionally localized signal changes for 918 and 920 characterizes a pain response to the 46° C. stimulus in reward/aversion circuitry that is objectively distinct (FIGS. 7C, 7D, 7G, 7H) from responses to the non-aversive thermal stimulus of 41° C. (FIGS. 7A, 7B, 7E, 7F).

It has, in accordance with the present invention, been recognized that the above-described WCA processing is more sensitive than processing which utilizes only T-test processing. Thus, the more sensitive WCA analysis can detect regions activated in the reward/aversion not recognized with prior art techniques, because the T-test alone is not sensitive enough to detect significant activity in some regions.

The WCA approach determines statistical significance using cross correlation of each pixel in a region of interest with the MHR derived from a BOLD signal. WCA analysis looks at pixel by pixel activation on a time of activation basis, but instead of performing pair correlation calculations among all pixels, each pixel is itself correlated with the MHR.

Activation maps for the regions shown in 922 and sensory/pain region 924 are generated conventionally by fusing anatomical images with statistical information indicating a range of validity values. Activation maps allow highly significant areas to be located and correlated to specific CNS structures.

It should be noted that different CNS regions are activated at different times. The early and late phase activation signals 918, 920 are used to derive images 922, 924 which indicate CNS regions generally activated (image 922) for the reward/aversion regions vs. others (image 924) regions respectively. The derivation process includes detecting any temporally correlated activity for a CNS structure of interest (i.e. compare the values in curves 918, 920 and with the CNS regions active during those times).

The early phase activation signal 918 and late phase activation signal 920 can thus be used repeatedly to detect any temporally correlated activity for any CNS structure of interest. The WCA can be applied either on a voxel by voxel basis or by regions of interest such as the NAc.

Further techniques can be used to quantify the activations after the WCA analysis. These techniques can also be applied to the MHR waveform. The methods include but are not limited to spatial comparison; a temporal comparison, a comparison of slope, moment analysis, laterality, synchrony, volume, differential power function, power spectrum analysis, and region matrix analysis. For example, an activation in the NAc can be quantified in time as occurring five seconds before an activation in the aCG.

FIGS. 11A–11I illustrate quantitative indices and qualification describes derived from WCA analysis of brain responses to an aversive stimulus (i.e., 46° C.) that were not observed for the 41° C. stimulus. Observations in this set include but are not limited to: (a) categorical signal differences for some reward/aversion regions; (b) increased volume of temporal lobe signal; (c) signal habituation; (d) biphasic distribution of signal dispersion ($\Delta$), (e) differential pattern of activation organized by time to peak (Tp) and dispersion ($\Delta$) measures; (f) alterations in the MHR waveforms; and (g) synchrony of activation among reward/aversion regions that respond early vs. those that respond late. All these measures provide for the objective dissection of the CNS response to pain. Psychophysical measures provide subjective but not objective assessments of the intensity, unpleasantness or presence of pain. By assessing quantitative descriptors and quantitative indices of function in reward/aversion circuitry, brain imaging can provide an objective measure of the pain experience.

Figure 11A:
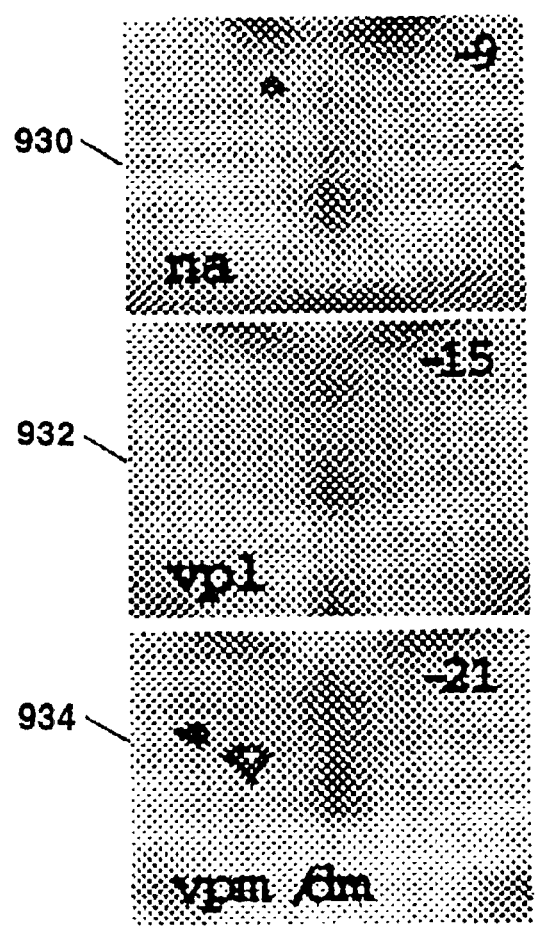
FIGS. 11A–11K are a series of figures which illustrate quantities derived from WCA waveform based correlation.

Referring now to FIG. 11A, the results of a spatial comparison technique are illustrated. Images 930–934 correspond to slices taken in differing spatial locations through the thalamus region. It is possible to spatially differentiate activation after the WCA analysis and detect different nuclei activated with pain by referring to an anatomical atlas of the thalamus.

The lower left side acronyms in images 930–934 identify the different thalamic nuclei. Thus image 930 corresponds to the anterior nucleus (na), (vl) image 932 corresponds to the ventroposteriorlaetral (vpl) and image 934 corresponds to the ventroposterior medial/dorsomedial (vpm/dm) The upper right numbers in each of the images 930–934 correspond to anterior posterior coordinate from the Talairach atlas.

Such spatial differentiation is useful because each nuclei shown in images 930–934 has been implicated in different functions. When some clinical conditions are added which alter the functions of the thalamus, such alterations can be observed using the techniques of the present invention described above in conjunction with FIG. 11. Prior art techniques where unable to trace such changes for pain. The thalamus has a number of nuclei each of which serves different functions (e.g. some at sensory vs. limbic/affective functions) FIG. 11A shows different activations in different nuclei which subserve different functions.

Figure 11C:
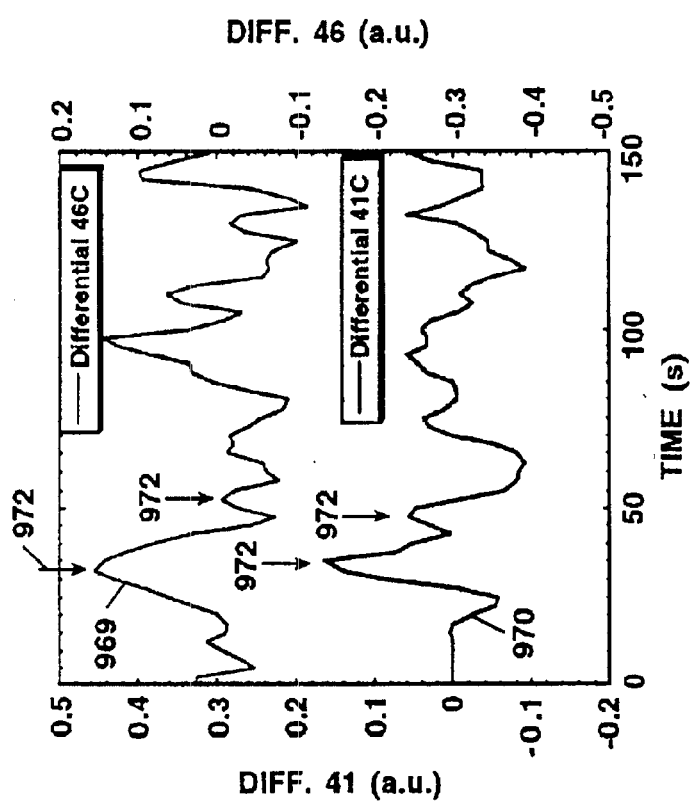
Figure 11B:
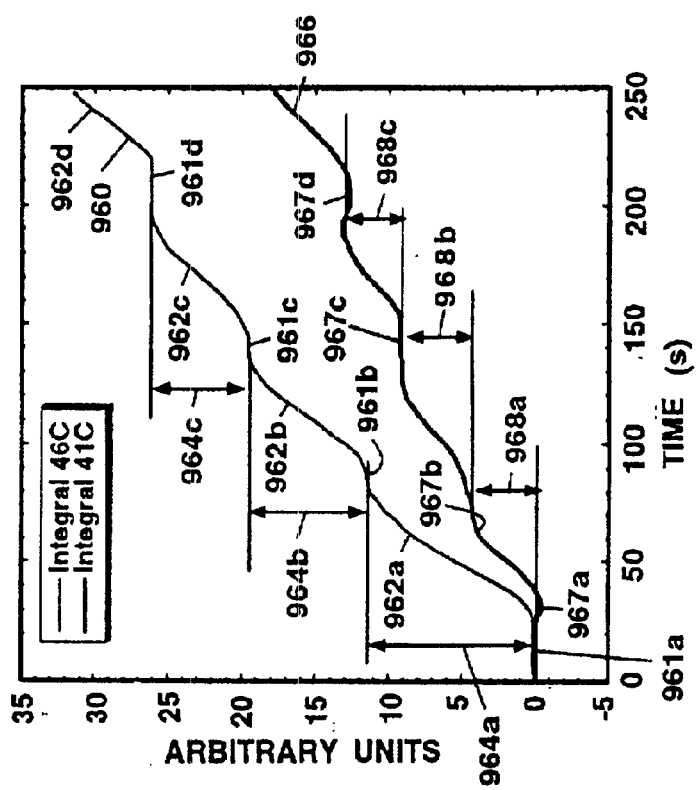

Referring now to FIG. 11B, a technique for quantifying a signal response (e.g. a signal response as measured in FIGS. 7I, 7J) includes integrating an MHR signal over time and measuring the change between any resulting plateau regions produced by the integration.

Such integrating and measuring steps were performed for the 46° C. experiment (as described in conjunction with FIGS. 7 and 11 to produce a curve 960.) Similarly, integrating the MHR over time for the 41° C. experiment produces a curve 966. The relative slope of each curve corresponds to an index for the total response as detected by WCA to the stimuli.

Curve 960 has plateau regions 961*a*–961*d* and rise regions 962*a*–962*d*. The distances between consecutive plateau regions 961*a*–961*d* are designated 964*a*–964*c*. Thus, distance 964*a* represents the vertical distance between plateau region 961*a* and plateau region 961*b*. Similarly distances 964*b* represents the vertical distance between plateau regions 961*b* and 961*c* and distance 964*c* represents the vertical distance between plateau regions 961c and 961d. For example illustrated in FIG. 11B, distance 964a corresponds to 12 units, distance 964b corresponds to 8 units and distance 964c corresponds to 6 units. Curve 960 was generated by applying four stimuli to a subject (i.e. thermal probe applied to a subject) and measuring the response in various brain regions as described above in conjunction with FIGS. 7–11. To generate curve 960, a 46° C. thermal probe was applied to the subject during the 30–60, 80–120, 150–190 and 220–250 time intervals as measured on the x-axis of the plot in FIG. 11B. It should be appreciated that the 46° C. thermal probe requires 5 seconds to reach a temperature of 46° C. when starting from a temperature of 35° C.

Since the distances 964a–964c var, this is a sign of adaptation of activation in the region being measured. In a similar manner to curve 960, curve 966 was generated by applying four stimuli to a subject (i.e. a thermal probe applied to a subject) and measuring the response in various brain regions as described above in conjunction with FIGS. 7–11. To generate curve 966, a 41° C. thermal probe was applied to the subject during the same time intervals described above for the 46° C. probe. It should be appreciated that the 41° C. thermal probe requires 2 seconds to reach 41° C. from 35° C.

Curve 966 has plateau regions 967a–967d separated by vertical distances 968a–968c. Each of the distances 968a–968c are approximately 4.5 units. Since the distances 968a–968c do not vary, this indicates that there is no sign of adaptation of activation in the region in response to the 41° C. thermal probe.

The 46° C. thermal probe is considered a painful stimulus (VAS score greater than 5 out of 10) while the 41° C. thermal probe in considered a non-painful stimulus (VAS score greater between 0 and 3). Thus, curves 960,966 can be used to generate quantitive indices such as measures of signal adaptation/habitation which are used to provide an objective measure of pain, between stimuli such as the 46° C. and 41° C. inputs.

Referring now to FIG. 11C, a plot of the first derivatives with respect to time of the curves 960, 966 of FIG. 11B are shown. Specifically curve 969 in FIG. 11C corresponds to the first derivative with respect to time of the MHR signal 914 in FIG. 11 for the 46° C. thermal probe experiment and curve 970 in FIG. 11C. corresponds to the first derivative of the MHR signal from the 41° C. thermal probe experiment in FIG. 11

Curves 969 and 970 correspond to the first derivative of the MHR's for the 46 and 41° C. experiments respectively. Curve 969 is obtained by differentiating MHR signal 914 (FIG. 11) for the 46° C. experiment. Arrows 972 mark points of inflexion that can be used as indices for the onset of activation. The peak-to-peak times can further be used to quantitate the duration of activation, and further differentiating in a quantitative fashion, the effects of the 46C and 41C stimuli.

Figure 11E:
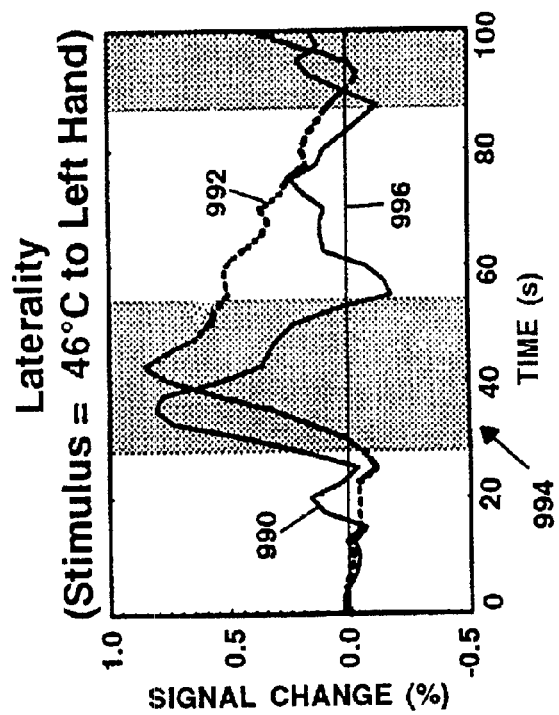
Figure 11D:
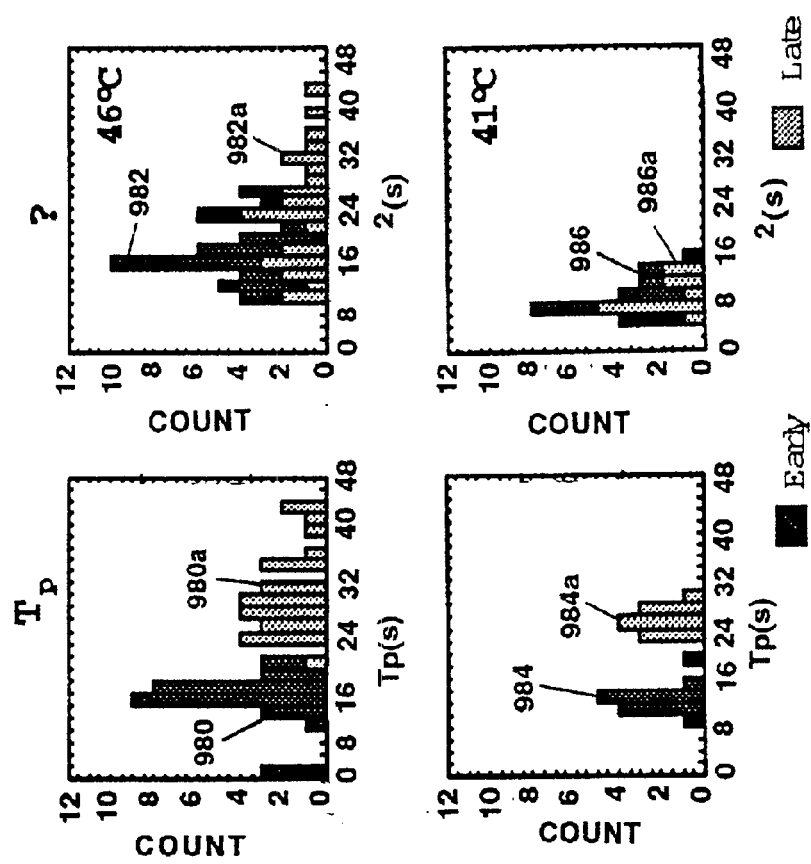

Now referring to FIG. 11D, a means of quantifying the MHR curve 914 (FIG. 11) using moment analysis is illustrated. Histograms 980–986a represent the time-to-peak (Tp) and the width or dispersion ($\Delta$) in CNS regions in response to thermal stimuli. The first moment, Tp, is an index of the onset-time for the response and the second moment, $\Delta$, is an index for the duration of the response. The y axis reflects the count of regions of activation and the x-axis represents time in seconds. The histograms are generated in a thermal stimulus experiment (as described above in conjunction with FIGS. 7 and 11).

Histograms 980 and 982 depict the distribution of the value of Tp and $\Delta$ respectively for activated areas during the early phase of the MHR (FIG. 11) using a 46° C. stimulus. Histograms 980a and 982a depict the distribution of the value of Tp and $\Delta$ respectively for activated areas during the late phase of the MHR (FIG. 11) using a 46° C. stimulus.

Histograms 984 and 986 depict the distribution of the value of Tp and $\Delta$ respectively for activated areas during the early phase of the MHR (FIG. 11) using a 41° C. stimulus. Histograms 984a and 986a depict the distribution of the value of Tp and $\Delta$ respectively for activated areas during the late phase of the MHR (FIG. 11) using a 41° C. stimulus.

The distributions allow one to objectively differentiate between the 46° C. (pain) and the 41° C.)(non-pain) stimuli.

As mentioned above, the time-to-peak (Tp) and dispersion ($\Delta$) measures can be used to segregate activations into a summary matrix as described below in conjunction with FIG. 11J. The response to the first stimulus of each activated area in both the early and late phase responses was fitted to a gamma function. The resulting fitting parameters can be used to calculate the time-to-peak (Tp) and the dispersion ($\Delta$) according to the following formulas and the parameters of equation (2):

$$Tp = c + d*e - 30 \qquad (2)$$

$$\Delta = 2*\sqrt{d}*e \qquad (3)$$

in which:

Tp is defined as the time at which the first derivative of the gamma function becomes zero $\Delta$ is defined as the time span between the two inflection points in the gamma function which could be obtained from the roots of the second order derivative of the gamma function.

In equation (2) 30 seconds were subtracted from Tp to shift the zero time, to the onset of the first stimulus.

Referring now to FIG. 11E, a means of quantifying the MHR curve 914 (FIG. 11) for laterality differentiation is illustrated. Curve 990 is the fMRI response as detected by WCA in the right aCG when the left hand is stimulated with 46° C. stimulus. Curve 992 is the response observed in the contralateral (left) aCG when the left hand is stimulated with 46° C. stimulus. The shaded area 994 represents the time when the stimulus is applied. Curve 996 represents a zero baseline signal. The x-axis represents time in seconds over the length of the experiment. The y-axis represents a percentage signal change with reference to the baseline value which is calculated by averaging dimensionless pixel signal values when the stimulus is not present.

Using WCA, bilateral signal changes can be deconvolved into early or late phase activations, and potentially localized in opposite hemispheres. In this way, one can quantify the temporal ordering of the brain activation. It should be noted that curves 990, 992 illustrate that both the left and right aCG activate, but that the activations have different times-to-peak and durations of activation, even though the same stimulus was applied. FIG. 11E thus illustrates that one can measure a sequence of events for subcomponents of the same structure. There may be some components that, although dominant, require that another component be involved to achieve an integrated response.

Figure 11F:
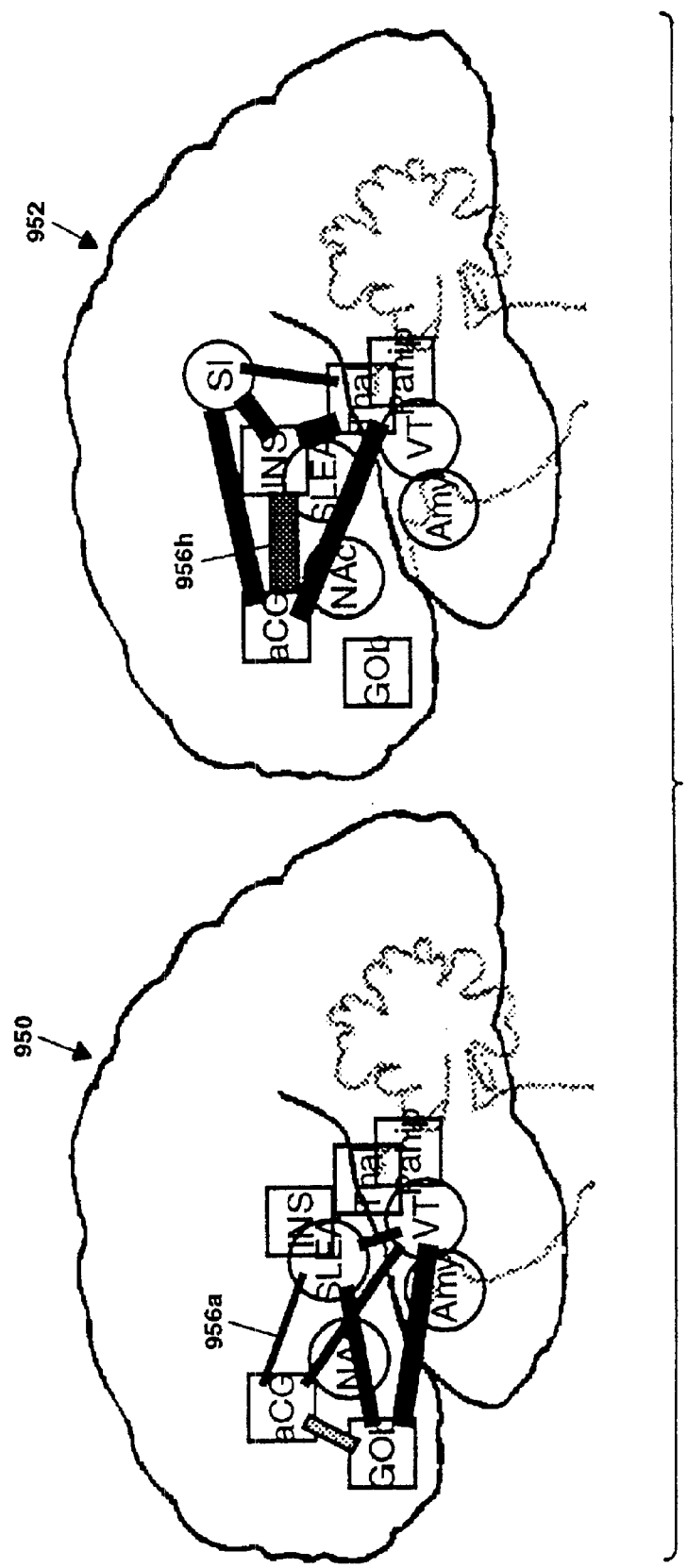

FIG. 11F shows the synchrony of activation within two sets of reward/aversion regions 950 and 952 following a noxious thermal stimulus. This synchrony pattern separates the pain response from the non-pain response. In the past, regions shown in region 950 were termed reward regions while regions shown in region 952 were thought to be classic pain regions. Establishing a temporal sequence of activation is one method to quantify the mapping results of the WCA analysis. The structures in the region 950 that shows significant correlation consist of the SLEA, VT/PAG, orbital gyrus and anterior cingulate cortex. Analysis of the correlation among structures in the region 952 indicated significant correlation of the insula, the thalamus, the SI, and the aCG.

The lines interconnecting each pair of regions represent a temporal correlation between the two regions. The thicker the line the greater the correlation. For example, the correlation coefficient between the aCG and the SLEA 956a is between 0.3–0.4. In 952, the correlation coefficient between the aCG and the INS 956h is greater than 0.9. It should be appreciated that no single part of the brain defines the response to chronic, acute or any other pain process. Generally the activation's illustrated in 950 occur in a early phase that occurs before the activations illustrated in 952.

Activation's for the 46° C. stimulus that are temporally correlated can be identified via a Pearson's correlation analysis. Significant correlation's (p<0.0025) can be observed for activation in the early phase of some reward/aversion. A strong correlation exists between the SLEA and VT/PAG along with the GOb and the aCG. In contrast, the NAc, which displayed a negative signal, does not correlate with the form or phase of signal from these regions. It should be appreciated that although only positive correlation's are shown in FIG. 11F, negative correlation's can be calculated.

Highly significant positive correlation is observed between structures such as SI somatosensory cortex, insula, and thalamus, that also occur in the late phase. The results indicate that a number of regions classically identified with pain function show correlated activation during the late phase.

Figure 11G:
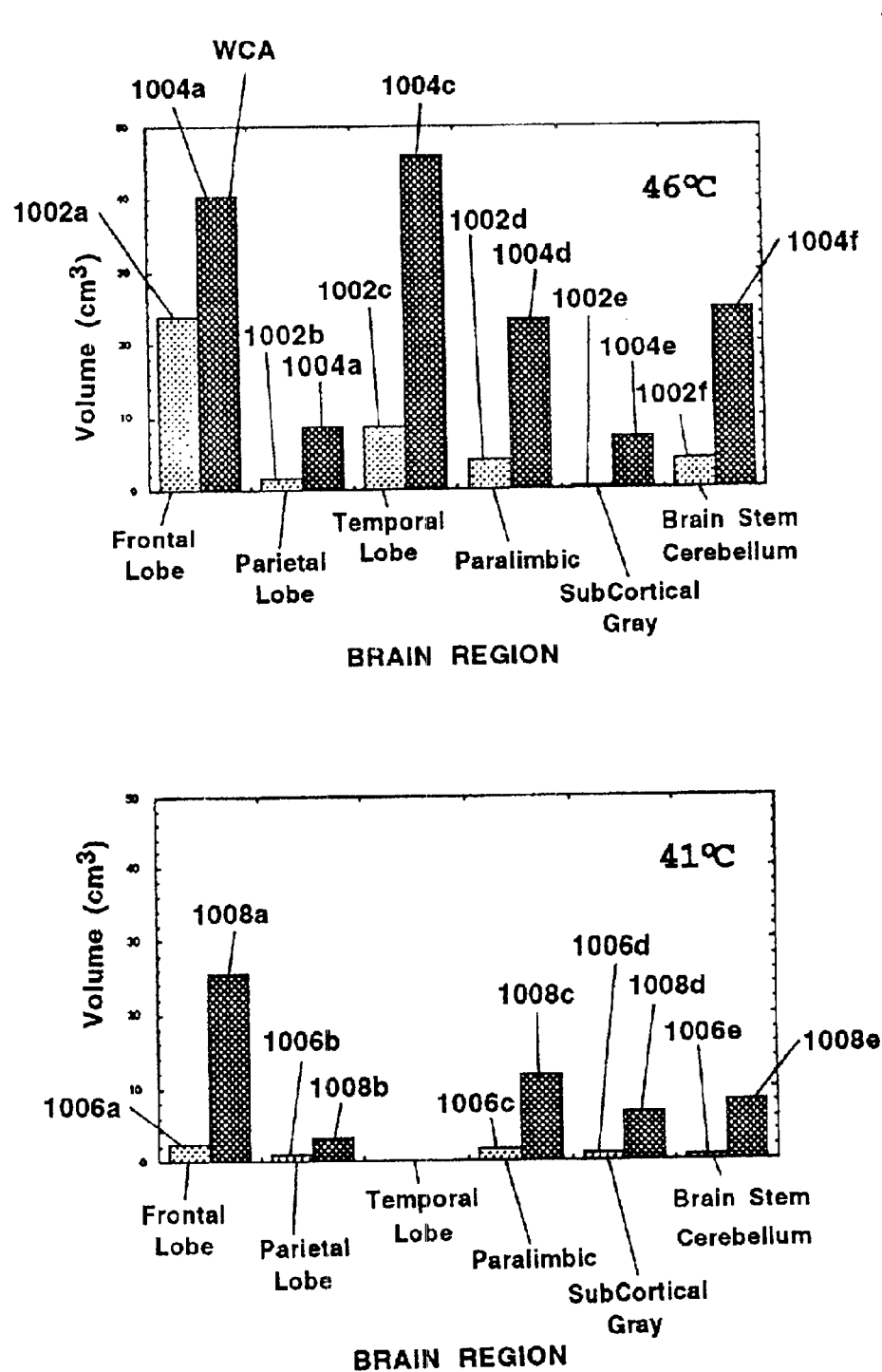

Referring now to FIG. 11G, an example of the quantification of the volume of activation as detected using both the WCA technique described above in conjunction with FIG. 11 and the standard T-test is shown both for 41° C. and 46° C. thermal probe experiments. By comparing the relative volumes via bars 1002a–1002f from the results of the T-test to the relative volume expressed as bars 1004a–1004f from the results of the WCA analysis, it is seen that the WCA analysis is more sensitive than the T-test (i.e. the WCA analysis is able to measure a greater volume of signal change with a greater sensitivity than the T-test approach). The volumes are measured as the total number of voxels activated above a statistical threshold in a particular region (the threshold is defined using a priori or post hoc criteria defined previously). FIG. 11G illustrates measured volumes for each technique in the frontal lobes, the parietal lobes, temporal lobes, medial paralimbic regions, subcortical gray matter, and the brainstem and cerebellum.

For parietal, temporal, paralimbic particular subcortical, and brainstem regions, activation for the 46° C. experiment, and for most of the regions for the 41° C. experiment. WCA detects more volume than the standard Student T-test analysis. These distinct volumes for the 46C and 41C conditions, as detected by WCA, further distinguish the pain response from the non-pain response.

Figure 11H:
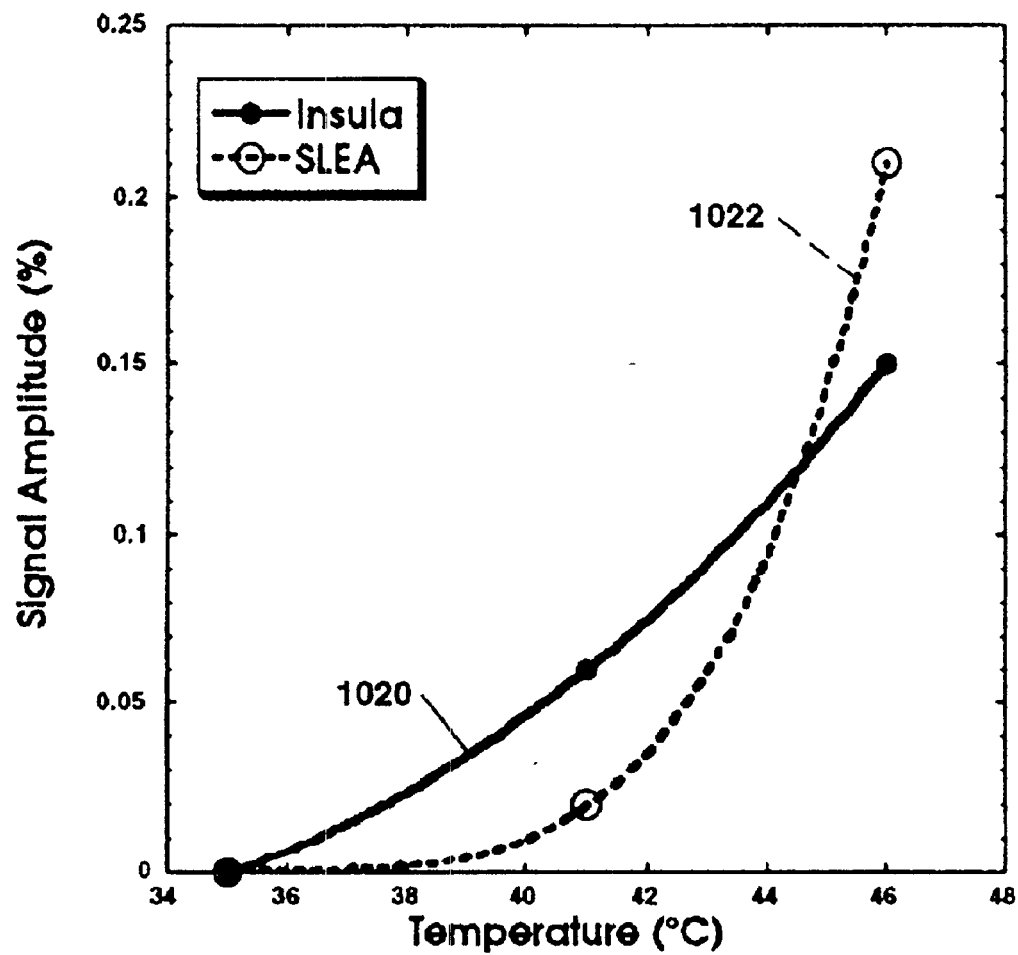

Now referring to FIG. 11H, a quantification of the differential power function as a function of temperature is shown. Curve 1020 corresponds to the percentage change of signal amplitude of activation as detected by WCA for the insula. Curve 1022 corresponds to the percentage change of signal amplitude of activation as detected by WCA for the SLEA. Both curves 1020 and 1022 display differential power law dependence on temperature. Such differences are used as indices for quantifying reward/aversion circuitry responses to painful vs. non-painful stimulation.

It should be appreciated that different structures might have a power function relationship to temperature which is different from each other. A number of reward/aversion structures may have a response similar to that shown for the insula, while others may have responses similar to that shown for the SLEA.

An exponent of power function for each for each brain regions is computed as:

$$(T-35)^x$$

| Structure | X |
|---|---|
| SLEA | 4.3 |
| INS | 2.1 |

Each of the responses of these brain regions can then be characterized by these indices.

Figure 11I:
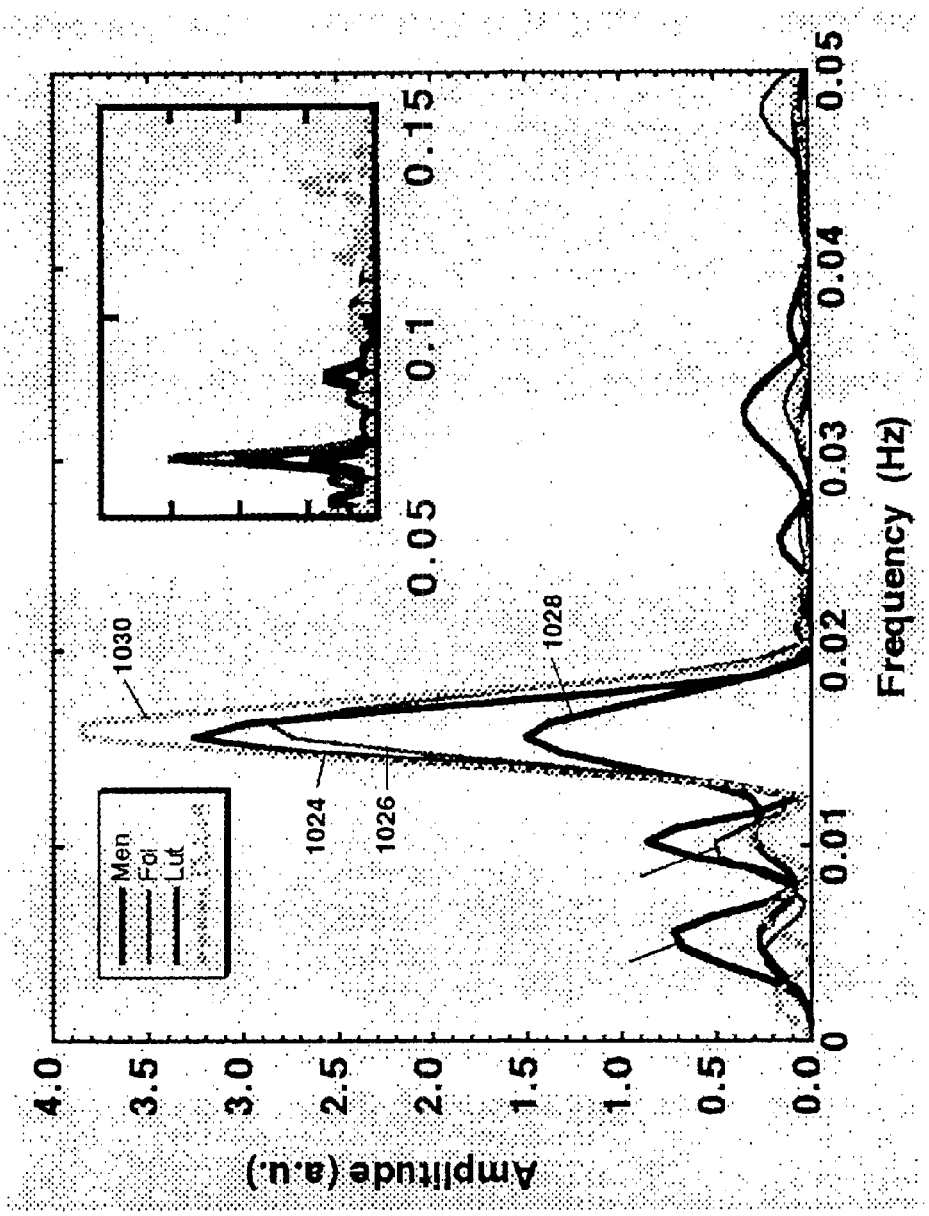

Now referring to FIG. 11I, fourier-transforms of MHR signals are shown for four temperature stimulus experiments. Curve 1024 represents a spectrum for a temperature experiment performed using male subjects. Curve 1026 represents a spectrum for an experiment performed using female subjects during the follicular phase of the menstrual cycle.

Curve 1028 represents a spectrum for an experiment performed using female subjects during the luteal phase of the menstrual cycle. Curve 1030 corresponds to the power spectrum of the actual temperature curve of the probe.

The inset graph is a continuation of the x-axis but at a different scale (as shown on the y-axis of the inset).

Each curve includes different contributions of other harmonics, taken together these harmonics uniquely characterize each curve. For example, signals having relatively high harmonics in the frequency range of 0.02 Hz to 0.05 Hz tend to have a relatively rapid onset and a relatively rapid return to baseline (curve 1028). Signals having responses in the frequency range of 0 to about 0.0125 Hz tend to have a relatively long lasting response. As shown by curves (1026 and 1028) this power spectrum analysis reveals relatively large differences for brain activation in female subjects at different points in their menstrual cycle. Thus power spectrum analyses provide another technique to quantify the response of a signal. Thus if it is desired to quantify the response to pain in three different groups, then power spectrum analysis can be used to segregate and identify the different groups.

Figure 11J:
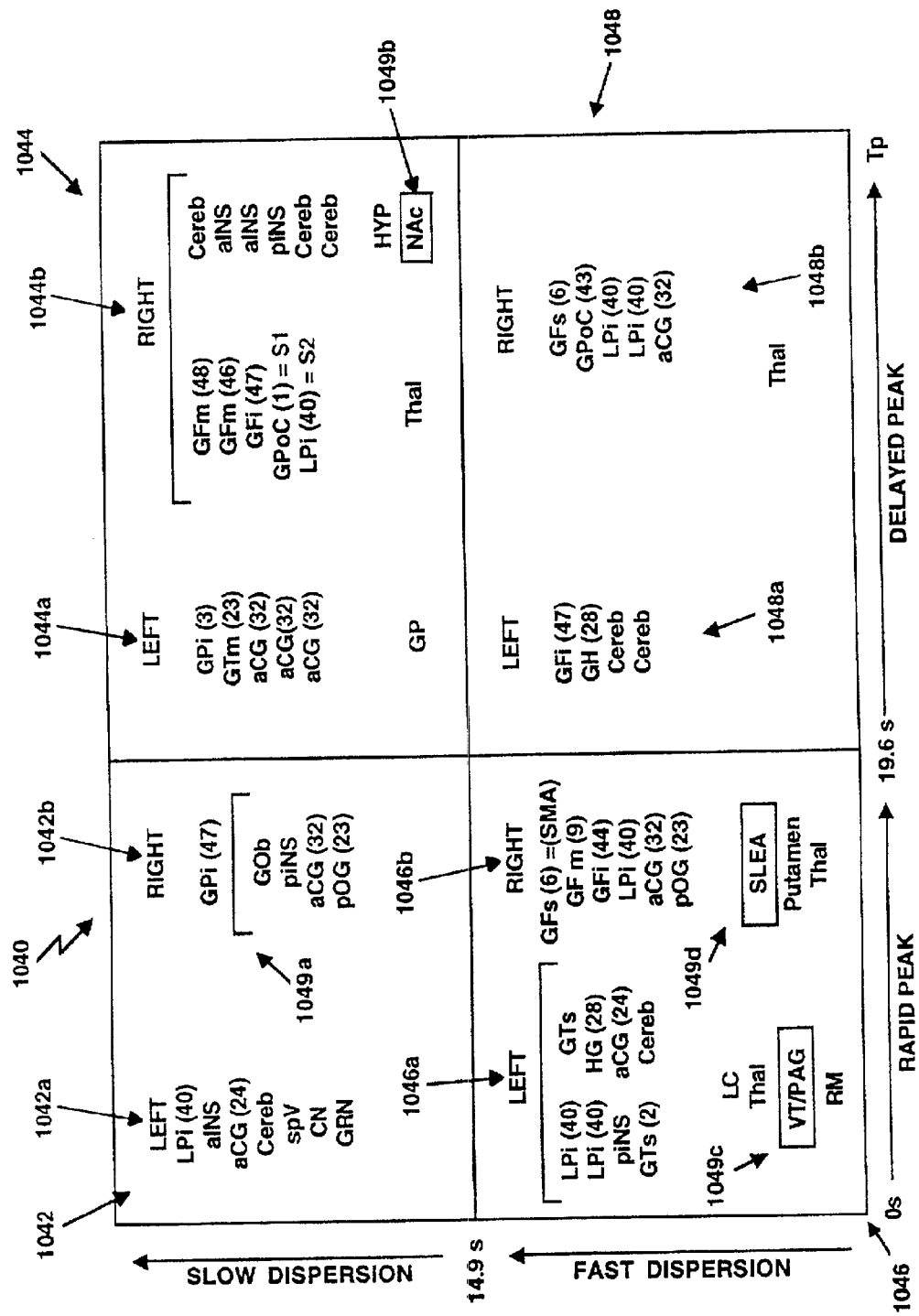

Referring now to FIG. 11J, a matrix 1040 can be generated for classifying various regions on the basis of response time (rapid peak or delayed peak),. dispersion time (fast or slow), and location (left or right). It should be appreciated that matrix 1040 corresponds to a pattern recognition matrix having a pattern recognition format for a brain function. In this particular example, matrix 1040 provides a matrix pattern for recognition of noxious heat. It should be appreciated, however, that other matrix patterns will be used for other stimuli (e.g. drug effects, etc . . . ). Matrix 1040 includes four quadrants 1042–1048. Each of the quadrants 1042–1048 include a left column 1042a–1048a and a right column 1042b–1048b.

Quadrants 1042, 1044 have listed therein brain regions having a dispersion time of greater than 14.9 seconds and which are thus characterized as having a relatively slow dispersion characteristic. Quadrants 1046, 1048 have listed therein brain regions having a dispersion time of less than 14.9 seconds and thus which are characterized as having a relatively fast dispersion characteristic.

Columns 1042a, 1042b, 1046a, 1046b have listed therein left and right brain regions having a peak response time of less than 19.6 seconds respectively and thus which are characterized as having a relatively rapid peak response time. Columns 1044a, 1044b, 1048a, 1048b are the left and right brain regions having a peak response time of greater than 19.6 seconds respectively and thus which are characterized as having a delayed peak response time.

Many of the brain regions also are listed with parenthetical reference numbers which correspond to Brodmann areas. It should be appreciated that regions 1049a, 1049b, 1049c and 1049d correspond to portions of the reward/aversion circuitry that in the past have had formally been considered to mediate reward and not pain functions. The work profiled here shows that these traditional reward regions are part of a generalized reward/aversion circuitry.

Activations can be classified as having a "rapid response" where $Tp<Tp_{mean}$ or having a fast dispersion where $\Delta<\Delta_{mean}$ ($Tp_{mean(46° C.)}=19.6\pm7.5$ s; $\Delta_{mean(46° C.)}=14.9\pm6.8$ s (mean±SD)). Structures with a Tp or a Δ larger than the average can be described as having a "slow response" or a "slow dispersion." Examples of regions with a rapid response and rapid dispersion to the 46° C. stimulus include the GOb while an example of a region with a slow response and slow dispersion is observed with SI somatosensory cortex.

It should be appreciated that matrix 1040 defines a pattern of indices for a particular pain or analgesic state (i.e. pain 1—a 46° C. thermal stimulus).

It is recognized, however, that for a different pain or analgesic state the pattern of indices will differ from that showm in FIG. 11J. For example, in response to an analgesic or non-noxious stimulus, the NAc, SLEA will not activate and thus no corresponding index will appear in the matrix 1040. As another example, the computation of the indices includes the valence characteristic of the regions. In a pain-2 state it is known that thalamus will change valence. Thus, the value of the index associated with the thalamus in the matrix will change from the value which is computed in the pain-1 case.

For Pain 3 both the NAc and the thalamus change valence and thus the values of these indices will change from that computed in the pain-1 case.

Also, the position of the indices within the matrix 1040 may change. That is NAc index may move from quadrant to another quadrant in response to some stimuli.

Figure 11K:
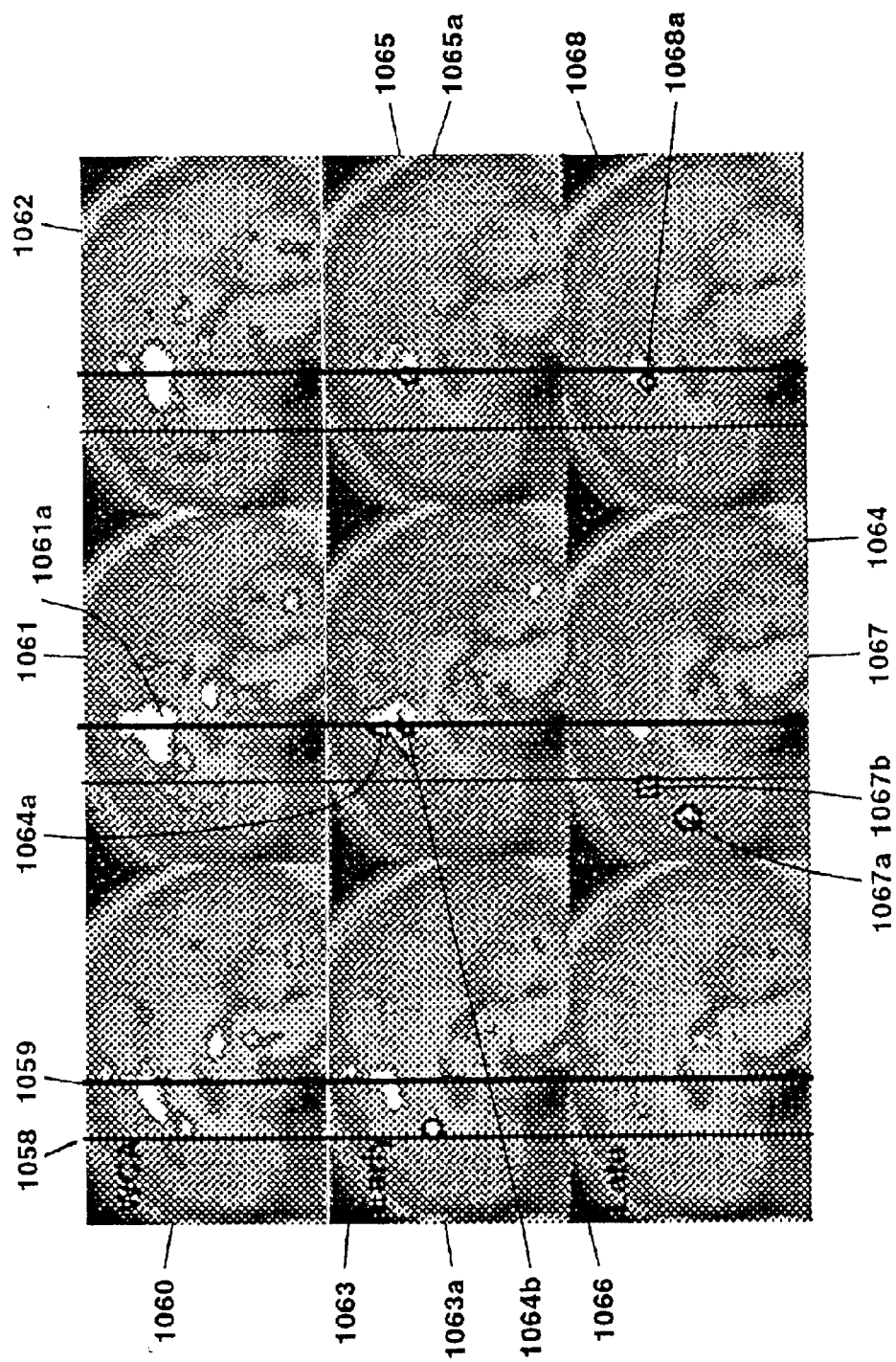

FIG. 11K illustrates how WCA analysis enables evaluation of foci of activation in a structure of interest such as the aCG. As described above, a focus of activation is a group of pixels showing significant activation compared with baseline that are found in a the gray matter of the brain. Typically one considers a focus of activation within a single structure, for instance, it is possible to differentiate activation within a structure (e.g. such as the aCG that occurs early or late after a aversive thermal stimulus).

Images 1060–1068 represent 3.125 mm MRI sagittal slices across the brain midline. Vertical lines indicate the location of the anterior commissaure (thick vertical line) 1059, and head of the corpus callosum 1058 (thin vertical line).

The top row, images 1060, 1061 and 1062, depicts activation in the aCG detected by WCA of the MHR. The middle row, images 1063, 1064 and 1065, depicts activation detected in the early phase, and the bottom row, images 1066, 1067 and 1068, depicts activation detected in the late phase. The center slice, images 1061, 1064, and 1067, runs through the middle of the brain, the others are located 3 mm to the right (left column) and 3 mm to the left (right column).

By deconvolving the WCA analysis of the MHR into the early and late phase (as described above in conjunction with FIG. 11), images 1063–1068 divide some activations into sets of activations with distinct temporal behaviors. Image 1061 has an activation region 1061a which can be deconvolved into early and late activation regions as shown in images 1064, 1067. For example, the pattern of activation in the aCG could be divided into number of foci, some within the putative "cognitive division", and the other within the putative "affective division" of the aCG.

The activation localized in the putative "cognitive division" could be dissected using WCA analysis into 4 foci in the early phase 1063a, 1064a, 1064b, 1065a and one focus in the late phase 1068a (images 1063–1068). No focus within the "affective division" of the aCG appeared during the early phase images 1063–1065, though at least two foci 1067a, 1067b activated in the late phase images 1066–1068.

Activation in the aCG that occurs early or late may represent activation in

This functional partition of the structure on the basis of its temporal response to an aversive stimulus distinguishes this response from the structures response during non-aversive stimulation, and can be used to identify the pain response as such merely from the functional imaging data.

To distinguish subtypes of pain, such as acute thermal pain (pain 1), from a surrogate model of neuropathic pain (e.g., capsaicin induced hyperalgesia, pain 2), or between acute pain (pain 1) and actual neuropathic pain (pain 3), other patterns of reward/aversion circuitry activation can be evaluated. For instance, to first focus on the distinction of acute thermal pain (pain 1) from an acute model of neuopathic pain (pain 2) by the patterns of brain activation, brain regions such as the brainstem spV region and the thalamus can be interrogated.

Referring now to FIGS. 12A–12F in which like elements are provided having like reference designations throughout the several views, the images reveal an activation of the spV ($5^{th}$ cranial nerve nuclei in the brainstem) following application of noxious heat (46° C.) in the manner described above in conjunction with FIGS. 7–11 to the skin of a healthy volunteers. Activation measured using a non-invasive measurement technique is shown in a coronal plane 1202 (FIG. 12) at an activation point 1204, in a horizontal plane 1206 (FIG. 12A) at an activation point 1208 and a sagittal plane 1210 (FIG. 12B) at an activation point 1212. The statistical threshold for activation was $p<0.01$.

The activation sites shown in FIGS. 12–12B can be compared with an anatomic map 1214 shown in FIG. 12C. A region 1216 in the anatomic map 1214 corresponds to an activation in the spV. Reference designators 1218 (FIGS. 12C, 12E) show the approximate location of activation in sagittal and horizontal anatomical sections. Reference designators 1220 (FIGS. 12D, 12F) show the location of the spV in caudal pons and caudal medulla. The designators "R," "L," "D," and "V" indicates right, left, dorsal, and ventral regions respectively.

Figure 13:
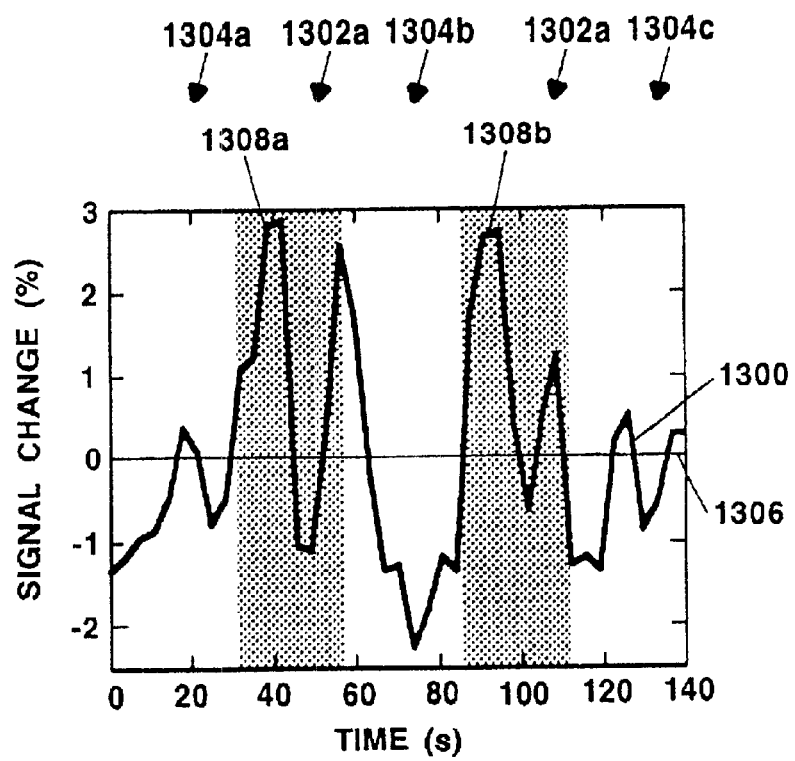
FIGS. 13 and 13A illustrate activation in the brainstem region spV and thalamus following allodynia produced by a heat-capsaicin model in a healthy volunteer.

Referring now to FIG. 13, surrogate models of sensitization are explained. Activation in the spV and thalamus following allodynia produced by a heat-capsaicin model in a healthy volunteer are, together, different than in acute pain.

In one experiment, the following paradigm was used. First allodynia was induced by application of heat in the form of a heat probe as described above to portions of the face of a subject. The heat was applied at a temperature of 44° C. for time period of 5 minutes. Next, a 0.075% capsaicin cream was applied for 20 minutes in the same facial area where the heat probe had been. The capsaicin cream was modified following the method described in "A new human experimental pain model: the heat/capsaicin sensitization model," Petersen and Rowbotham, Neuroreport. 1999; 10(7):1511–6. Allodynia was produced by the application of normally non-noxious brush and 41 ° C. stimuli to the right (R) and left (L) V2 division of the trigeminal node.

For the 5 minute thermal application, the capsaicin application and the pain induced by normally non-noxious mechanical and thermal stimuli to the right or left V2 region, the subjects rated the intensity of the pain they experienced using a conventional on-line VAS rating scheme (i.e. an 11 point visual analogue scale 0–10; where 0=no pain and 10=maximum pain). The subjects rated the 5 minute thermal application and the capsaicin application on the V2R as approximately 5 and 2.5, respectively, on the VAS rating scale. The application of the brush to the V2R region was rated as a 2.5 on the VAS scale and the brush to the V2L region (i.e. the untreated V2 region) produced no pain. Also, application of the 41° C. probe to the V2R region was rated as approximately 9 on the VAS scale while application of the 41° C. probe to the V2L region was rated as approximately 1 on the VAS scale.

Following the application of the 41° C. thermal probe to the V2 area of the skin treated with capsaicin, activation in the ipsilateral spV was observed using a noninvasive measurement technique (e.g. fMRI) while no activation was observed in the contralateral/untreated V2 side using the same noninvasive measurement technique. This indicates that the measured activations in the ipsilateral spV correspond to the ratings provided by the subjects on the VAS scale, and are the same during a surrogate model of neuropathic pain (pain 2) and during acute pain (pain 1)

As shown in FIG. 13, a curve 1300 of the spV region representing the response to a series of non-noxious thermal pulses 1302a, 1302b (as administered via 41° C. thermal probe pulses) followed by periods of neutral temperature 1304a, 1304b is shown. Curve 1306 represents a zero baseline signal. Curve 1300 is plotted as percent signal change vs. time (seconds).

For each thermal pulse period 1302a, 1302b representing an increase in temperature to 41° C. in the thermal stimulus, there is a corresponding positive percentage change in the temporal response 1308a, 1308b in the ipsilateral spV. Thus the ipsilateral spV is positively valenced with respect to thermal pain indices by experimental allodynia (pain 2). This response can be used in conjunction with responses from other reward/aversion circuitry (e.g. GOb, NAc) to allow an objective determination of whether a subject is actually experiencing pain to be made.

To distinguish between pain 1 and pain 2, differential responses in the thalamus may be used. In acute pain, the thalamus produces positive signal change (FIG. 1F, 952).

Figure 13A:
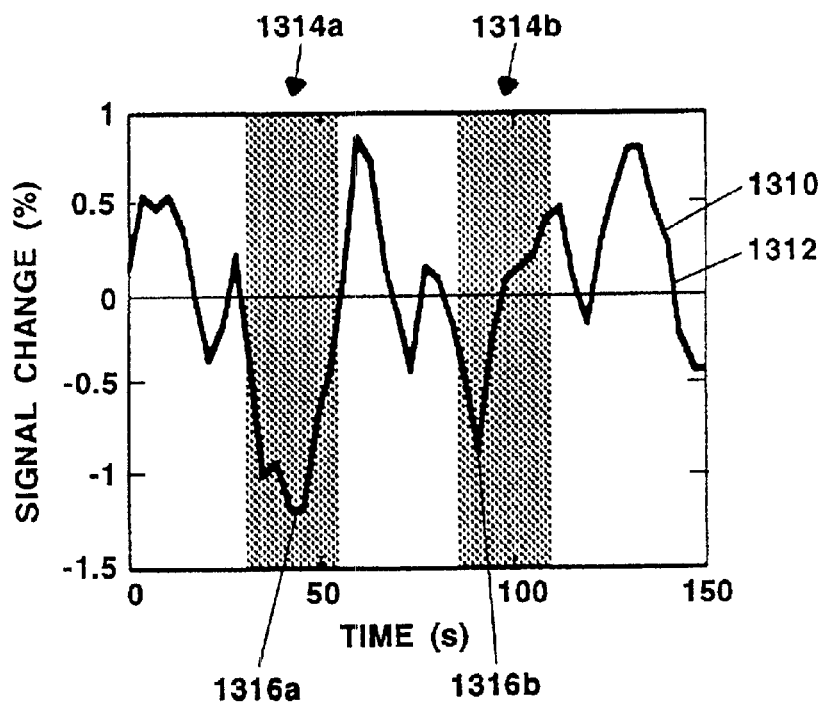

Referring now to FIG. 13A, a curve 1310 representing the response of the thalamus to a series of brush strokes of an example of pain 2 is shown. Curve 1312 represents a zero baseline signal. The brush strokes are applied during time periods designated 1314a, 1314b. Curve 1310 shows a decreased signal change in the thalamus in the sensitized state as evidenced by regions 1316a, 1316b.

That is, there is a decrease in signal in the contralateral thalamus following brush induced allodynia compared with no signal induced by brush on the contralateral mirror side alone (p<0.01, t-test).

Differences in the sign of signal change in reward/aversion regions such as the thalamus may be used to distinguish subtypes of pain such as pain 1 and pain 2.

Referring to FIGS. 14A and 14B, a means for objectively differentiating acute physiological or acute pain (pain 1) from chronic pain (pain 3) is shown. Central nervous system (CNS) activity in the NAc is shown in response to application of capsaicin and a brush stimulus. A camel hair brush is applied to the skin to produce a painful response in a chronic pain subject with damaged nerves (allodynia). The response may be measured, for example, by using a system such as that to be described below in conjunction with FIG. 11.

Referring now to FIG. 14A, an image of a NAc having an activation 1400 in response to a brush stimulus is shown. The brush stimulus is delivered to a subject using a camel hair brush. The size and shading of the activation shown in FIG. 14A indicate the relative extent and statistical significance respectively within each region. The size of the shaded region corresponds to the amount of activation volume in the NAc. Thus, a relatively small size corresponds to a relatively low activation volume in the NAc while a relatively large size corresponds to a relatively large activation volume in the NAc. Also, a region having a darker shading indicates a less significant activation while a region having a lighter shading indicates a more significant activation.

FIG. 14B shows a series of unshaded regions 1402 and shaded regions 1404 representing a resting period and a brush stimulus respectively delivered in the form of a series of brush strokes. Each of the brush stimuli 1404a–1404b are provided having a pulse duration typically of about twenty-five seconds followed by a resting period 1402b and 1402c having a duration typically of about thirty seconds and during which time no stimulus is applied to the subject.

Also shown in the plot of FIG. 14B is a curve 1406 which corresponds to a zero baseline signal and a second curve 1408 which corresponds to a plot of signal change (in percent) vs. time (in seconds) of a signal in NAc generated in response to the stimulus (e.g. the series of brush strokes 1404a and 1404b) being applied to the subject. The x-axis represents time in seconds over the length of the experiment and the y-axis represents a percentage signal change with reference to the baseline value which is calculated by averaging dimensionless pixel signal values when the stimulus is not present using a technique which is generally known in the art.

It should be appreciated that for each the series of brush strokes 1404a and 1404b, there is a corresponding positive percentage change in the temporal response as evidenced by regions 1408a–1408b of curve 1408 in the NAc. That is, each time one of the series of brush strokes 1404a and 1404b is applied to the subject, an increase is measured in the response of the NAc to the series of brush strokes as shown by regions 1408a–1408b in curve 1408 in FIG. 14B. As is known, the NAc is part of the reward/aversion in the brain and since application of one of the series of brush strokes 1404a and 1404b elicits a corresponding increase 1408a–1408b (as measured by percentage signal change) in the NAc response, the NAc is said to be positively valenced with respect to pain. Typically heat pain produces negative/decreased signal in the NAc (i.e., pain activation in the normal and sensitized state in a normal nervous system produces decreased signal in the NAc). However, pain produced by brush in a chronic pain patient with damaged nerve (allodynia) results in a positive signal in the NAc. By recognizing this type of response using WCA, a means for objectively differentiating acute physiological or acute pain (pain 1) from chronic pain (pain 3) is provided.

Referring now to FIGS. 15–15C, activations for a thermal stimulus experiment (as described in conjunction with FIGS. 7 and 11) in three structures for men, for women during the follicular phase of the menstrual cycle, and for women during the lateral phase of the menstrual cycle are shown.

In FIG. 15, images 1502, 1503, and 1504 depict activation in the frontal lobes, while images 1505, 1506, and 1508 depict activation in the insula and images 1510, 1511, and 1512 depict activation in the aCG.

FIGS. 15A–15C show curves 1514, 1516, and 1518 which correspond to measured MHR's for men, women during the mid-follicular and during the mid-lateral phases respectively. Curves 1514, 1516, 1518 correspond to average MHR signals for the entire brain. It should be noted that the responses as evidenced by curves 1514, 1516, 1518 are different for each of the different groups of subjects. That is, the MHR curve 1514 for men differs from the MHR curves 1516, 1518 for women during the follicular and during the luteal phases respectively. Thus an objective measure of gender differences is provided.

Similarly, curve 1516 for women during the follicular phase differs from curve 1518 during the luteal phase. Thus an objective measure of differences between women at different points in their menstrual cycle is provided.

Such results can be incorporated in a pattern matrix such as the pattern matrix described above in conjunction with FIG. 11J. Furthermore, in addition to measuring differences in gender and differences in women at different phases of their menstrual cycle, the measurements can also be used in selecting subjects for a drug study. For example, if one is performing a drug study using men and women, it is desirable to have the subjects as closely correlated as possible. Thus, it may be desirable to use the above objective measure to select, for example, women in the follicular rather than luteal phases of their menstrual cycle if they are to be compared to a group of men.

Figure 16:
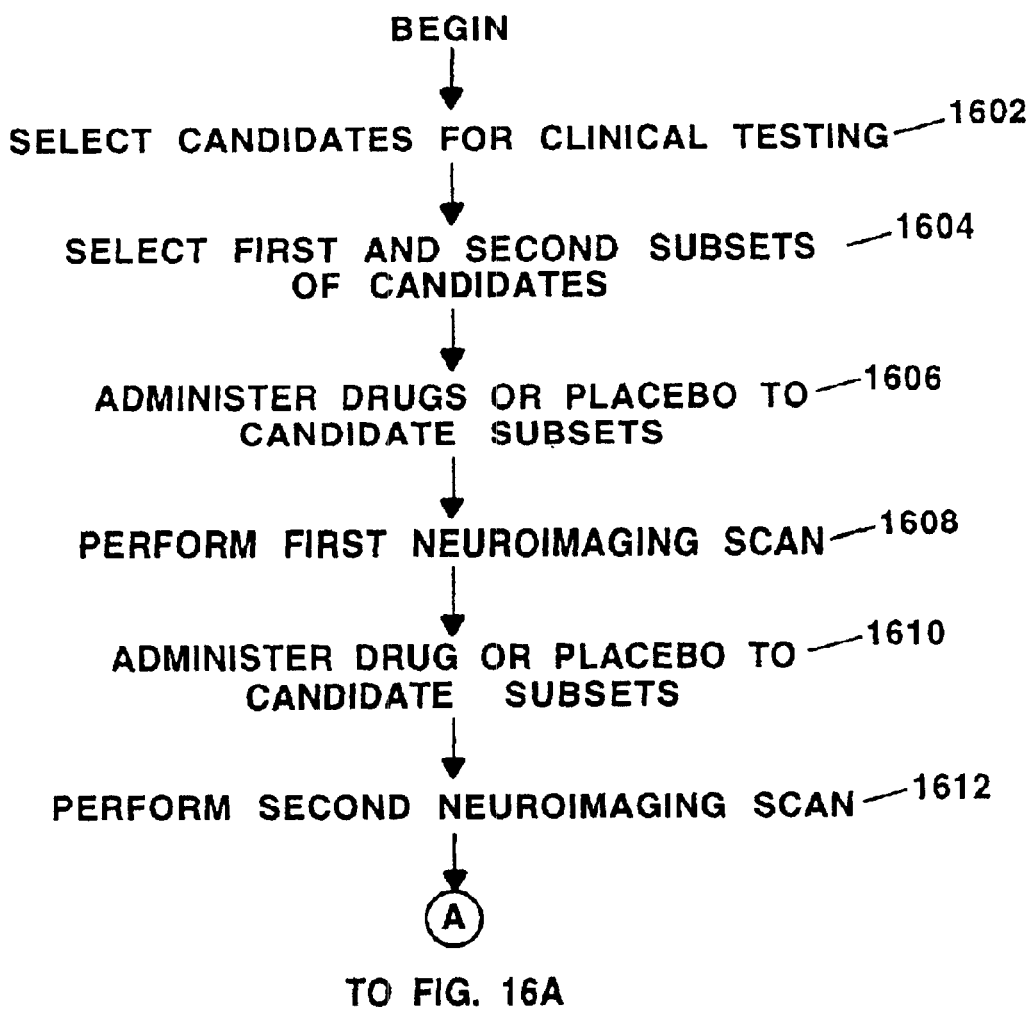
FIG. 16 is a schematic diagram of a method for rapid drug evaluation in humans.
Figure 16A:
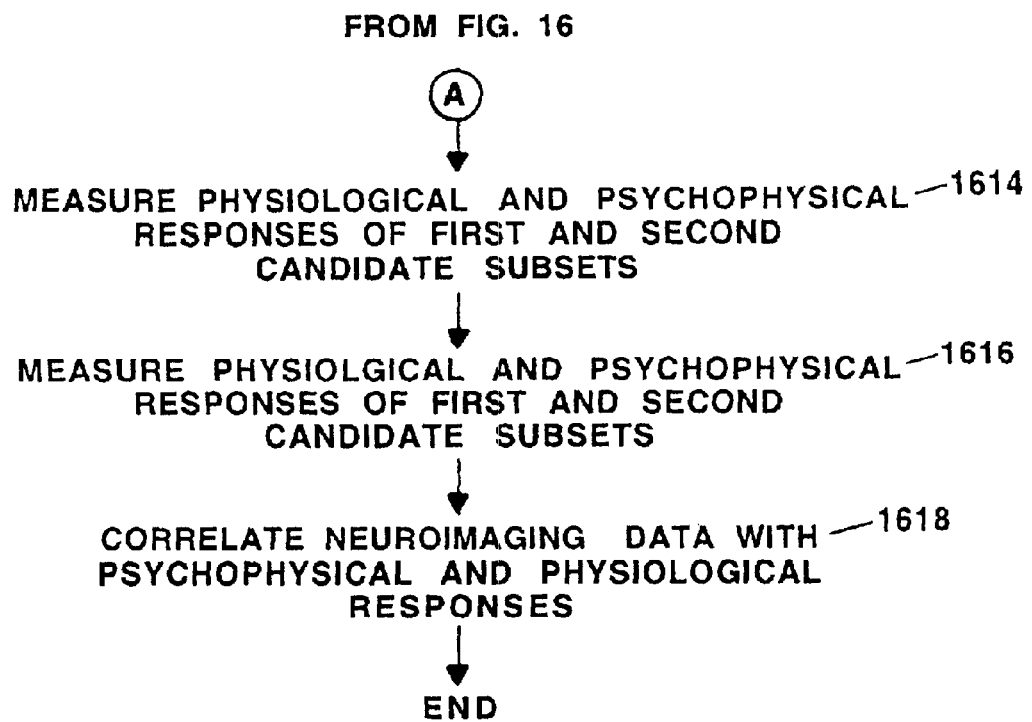

Referring now to FIG. 16, a drug evaluation technique for rapidly evaluating drugs in subjects, including human subjects, begins with step 1602 in which candidates are selected for clinical testing. The step of selecting candidates includes selecting a group of subjects and performing conventional molecular discovery and pre-clinical evaluation to select candidates for the clinical testing. The selection step may include, for example, the selection of an enriched group (e.g. a group in which the subjects have a response to a particular drug/test which indicates that the subjects are mechanistically similar or a group in which there is a pain response after withdrawing medication). The selection step may alternatively seek a random group of subjects meeting study inclusion criteria. Other methods, well known to those of ordinary skill in the art for selecting relatively small groups for drug testing may also be used.

The technique then proceeds to step 1604 in which each of the selected candidates are randomly selected to be included in one of the first and second subsets (i.e. the candidates are divided into two groups). Next, as shown in step 1606, each of the candidates in the first subset has a drug administered to them and each of the candidates in the second subset has a placebo administered to them. The dosage of the drug or placebo administered to each of the candidates corresponds to an amount equal to a therapeutic or sub-therapeutic dose of the drug to be tested or the placebo.

Before describing steps 1608–1616 it should be noted that these steps are preferably performed simultaneously. However, it may be possible to practice some of steps 1608–1616 at a different time than other of steps 1606–1608.

In step 1608, the first neuroimaging study is then performed on both the first and second groups of candidates to non-invasively measure signals from the their central nervous systems (CNS), specifically focused on reward/aversion circuitry, or output/input regions to them. In one example, fMRI measurements from a central nervous system (CNS) are then processed using the WCA method described above in conjunction with FIGS. 7 and 11, to evaluate signals for various CNS regions in each candidate in response to the effects of the drugs and placebo. Thus, in steps 1606 and 1608, a drug being investigated is provided to the first subset of candidates while a placebo is given to the second subset of candidates and a noninvasive measurement of a response in a brain region is made.

The technique then continues by administering a placebo to each of the candidates in the first subset and a drug to each of the candidates in the second subset as shown in step 1610 and then performing a second neuroimaging scan on both the first and second subset of candidates as shown in step 1612. Thus, in steps 1610, 1612, a drug being investigated is provided to the second subset of candidates while a placebo is given to the first subset of candidates and a noninvasive measurement of a response in a brain region is made.

The process continues in steps 1614, 1616 in which the psychophysical responses and physiological responses are collected for each of the subjects in response to the effects of the drugs and placebo. The physiological data may be collected, for example, during a series of experiments in which stimuli are provided to the subject. Such psychophysical and physiological responses are described above in conjunction with the MEMP processing described in FIG. 5.

The fMRI data (showing differential activation), on-line psychophysical (e.g., pain ratings and other hedonics) and physiological data (e.g. heart rate (HR), electrocardiogram (ECG), ETCO2, GSR or laser-Doppler measures of skin-blood flow) are recorded for correlation analysis.

In step 1618 the fMRI data, psychophysics data and physiological data are correlated. Such correlation maybe performed, for example, as described above in conjunction with FIG. 5. The objective measures provided by the fMRI technique allows fewer test subjects to be used than in prior art techniques. By computing fMRI data for each of the candidates in the first and second groups and correlating the fMRI data with the psychophysics data and the physiological data, the effect of the drug on the candidate can be rapidly evaluated.

In one embodiment, the technique utilizes an N of 1 design method with a double-blind cross-over design (e.g. neuroimaging I and II). This may then be repeated on a third trial for either a placebo or a drug. The candidates receive three scans with a drug or a placebo in a double-blind, randomized, cross-over (Neuroimaging I and II or III) design. This procedure can optionally be repeated in a third trial for either the placebo or the drug. The physiological/psychophysical and fMRI data sets are all collected during the experiments. By correlating the fMRI measurement with physiological and psychophysical measures, one is able to dissect the fMRI brain data into its functional subcomponents as discussed above. It is desirable to correlate fMRI data with physiological and psychophysical since a positive correlation between the fMRI and physiological and psychophysical measurements, one can objectively define the relationship between structure and function. It also allows verification that the data is not tainted by physiological artifacts.

The data can be further correlated to results from testing a similar drug or a drug which has desirable properties. The results can be used to look at analgesic effects of drugs by objectively examining the time correlated effects in the reward/aversion regions with the psychophysical and the psychophysical measurements.

The technique of the present invention can thus be used to evaluate drugs more rapidly than conventional methods because it uses physiological and psychophysical data which is correlated with activations in CNS regions (i.e. an absolutely objective measure provided via the fMRI process) which are implicated in the effects of the drug compound.

Conventional techniques fail to provide an objective test for measuring the effect of a drug on chronic pain. Animal models may not adequately define the human condition during chronic pain, and thus are frequently not helpful for early determination of potential clinical efficiency. The qualitative description and quantitative indices characterizing the pain response (for Pain 1, 2, or 3), in reward/aversion circuitry as accessed by neuroimaging will further allow investigators to discover where a particular drug acts on the CNS to produce its effects.

Clinical trials using the technique of the present invention can provide an accurate assessment of a drug by evaluating a low number of subjects (i.e., 20 subjects) instead of the large cohort typically needed by other empirical techniques. Furthermore, the current invention gives an absolute objective measure of pain.

The experiments and stimuli provided to the subjects can be developed using empirical techniques. In the above examples, thermal probes and mechanical brushes were used. It should be appreciated, however, that other thermal, mechanical, chemical or other stimuli can also be used.

It will be appreciated by those of ordinary skill in the art that the technique of the present invention can be used to evaluate various compounds, drugs, and biopharmaceuticals both in therapeutic and sub-therapeutic dosages. The technique of the present invention can also be used to discover new drugs, gene products, and therapy (for example acupuncture).

Coupled with specifically designed experiments, this method can augment or replace clinical experts and panels using techniques such as the Diagnostic Statistical Manuals (such as DSM-NR) for psychiatric classification of disease. This method would specifically evaluate reward/aversion regions implicated in the presentation of psychiatry and psychological dysfunctions, to objectively determine the presence of such psychiatric or psychological problems in clients and patients. This method would thus produce a set of radiological tools and techniques to replace the current use of patient signs and symptoms as used in current DSM-NR or other diagnostic formulations to diagnose psychiatric and psychological dysfunction, to predict treatment response, to monitor treatment progress, and ultimately to determine successful treatment. It is important to note, that this method would also be applicable to evaluating and diagnosing functional sequelae of pain syndromes.

This technique reduces the number of subjects typically required for an evaluation to a substantially smaller cohort site (for example, N=10 subjects).

Figure 17:
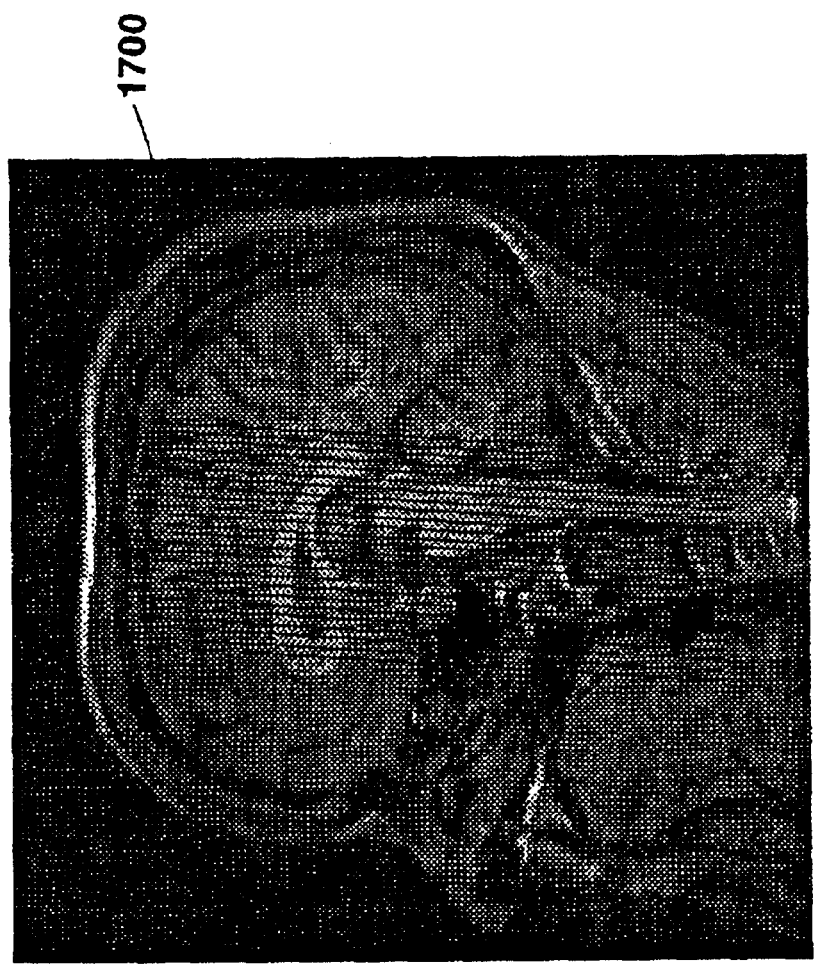
FIG. 17 is a flow diagram of a method to image CNS regions in the brainstem (trigeminal nucleus).

Referring now to FIG. 17, a technique for imaging the trigeminal nucleus is shown. It is desirable to image the SpV since the SpV is the first synapse from the periphery and thus it provides information regarding pain input to reward/aversion circuitry (i.e. it is the "gateway" to the central nervous system). Conventionally, CNS regions in the spinal cord 1702 have not been imaged to detect pain because the region is difficult to image with MRI and not accessible with PET. The degradation of the MRI signal is due to the noise induced by cardiac-induced effects. The cardiac-induced signal fluctuations overwhelm or partially mask the signal of interest, making it difficult to process. The artifact in the images occurs because the standard imaging plane is orthogonal to the spinal cord. The conventional method and imaging axis tend to be optimized for imaging other areas of the brain and not the brain stem. A non-standard plane is used in the technique of the present invention to minimize cardiac-induced signal fluctuations on the signals of interest.

The selection of planes (called "slice prescription") was discovered by observing slices capturing the brain stem. It was noticed that the brain stem was coming in and out of the image with each cardiac pulse. Those slices were prescribed per standard methodology (i.e. a methodology in which alignment is done with brain landmarks such as the anterior commissar-posterior commissar axis). In the present technique, slices are prescribed that are parallel to the brain stem. In one embodiment, the technique includes prescribing 3–4 slices out of 30 behind the brain-stem with each slice being 3 mm thick. It is thus not necessary to measure angles, as with any standard prescription of slices. In one embodiment, slices can be aligned with certain landmarks. In one particular example, the fifth slice is placed at the posterior edge of the brain stem and runs as parallel as possible along it. Cardiac gating can also be used with the above technique to further improve the measurement results.

All references cited herein are hereby incorporated herein by reference in their entirety.

Having described preferred embodiments of the invention, it will now become apparent to one of ordinary skill in the art that other embodiments incorporating their concepts may be used. It is felt herefore that these embodiments should not be limited to disclosed embodiments, but rather should be limited only by the spirit and scope of the appended claims.

What is claimed is:

1. A method of processing brain activity signals, the method comprising:

selecting an experimental process which elicits a response in one or more reward/aversion regions of a subject;

applying a reward/aversion stimulus to the subject to elicit the response;

noninvasively obtaining signals of central nervous system (CNS) activity from the subject;

localizing signals to specific anatomical and functional CNS regions which participate in reward/aversion functions;

correlating the signals in the one or more reward/aversion brain regions to a type of pain; and interpreting the correlation results as an indication of the type of pain in the subject, wherein correlating the signals from reward/aversion brain regions comprises evaluating the temporal nature of a neuroimaging signal using waveform based correlation analysis (WCA).

2. The method of claim 1, wherein the reward/aversion regions include at least one of the subcortical gray, brainstem, cerebellum and frontal brain regions.

3. The method of claim 2 wherein the brainstem region includes the spinal cord.

4. The method of claim 3 wherein the spinal cord includes the trigeminal nucleus and the method further includes the step of non-invasively obtaining signals from the trigeminal nucleus.

5. The method of claim 4, further comprising:

aligning an imaging axis of an imaging device with the spinal cord of a subject such that the imaging axis is aligned in a plane parallel to a spinal cord axis and perpendicular to a cerebral mid-plane; and obtaining images of CNS regions in the spine.

6. The method of claim 1 wherein the reward/aversion regions include at least one of the orbital gyrus (Gob), ventral tegmentum/periaqueductal gray (VT/PAG), nucleus accumbems (NAc), sublenticular extended amygdala (SLEA), cingulate gyrus, primary somatosensory cortex (S1), secondary somatosensory cortex (S2), thalamus, insula, cerebellum, prefrontal cortex, amygdala, hypothalamus, parahippocampal gyrus, hippocampus, entorrhinal cortex, ventral pallidum, dorsal striatum, primary motor cortices (M1), secondary motor cortices (M2), supplementary motor cortex (SMA), frontal eye field (FEF), rostral ventralmedial medulla (RVM), and brainstem subnucei.

7. The method of claim 1, wherein obtaining signals CNS activity includes using a neuroimaging device wherein the signals reflect at least one of functional activation, chemical signatures, brain structure, neurotransmission, electromagnetic activity, perfusion effects and cell metabolism.

8. The method of claim 7, wherein the neuroimaging device corresponds to one or more of a positron emission tomography (PET) device, a functional magnetic resonance imaging (fMRI) device, a magnetoencephalography (MEG) device, an electroencephalography (EEG) device, a single photon emission computer tomography (SPECT) device, an infrared (IR) device, a magnetic resonance spectroscopy (MRS) device, and a functional computerized tomography (CT) device.

9. The method of claim 1, wherein non-invasively obtaining signals of central nervous system activity further comprises:

correcting the signals to reduce the effects of head motion;

transforming the signals into a uniform atomic space;

normalizing the transformed signals;

statistically mapping the normalized signal; and locating the statistical maps over images reflecting at least one of: a uniform atomic space, an average anatomic space, and an individual atomic space.

10. The method of claim 1, wherein non-invasively obtaining signals of central nervous system activity further comprises:

correcting the signals to reduce the effects of head motion;

aligning the signals with individual brain anatomy;

normalizing the transformed signals;

statistically mapping the normalized signal; and locating the statistical maps over images reflecting at least one of; a uniform atomic space, an average anatomic space, and an individual atomic space.

11. The method of claim 1, wherein data obtained from central nervous system activity is segregated temporally.

12. The method of claim 11 wherein data obtained from central nervous system activity is segregated temporally into a plurality of phases.

13. The method of claim 12, wherein interpreting the results of the correlating procedure further comprises correlating a plurality of pixels from regions in the CNS to distinct waveforms.

14. The method of claim 13, wherein the distinct waveforms correspond to at least one of an early phase waveform and a late phase waveform.

15. The method of claim 13, wherein interpreting the results of the correlating procedure further comprises producing indices by quantifying the signals using at least one of:

a spatial analysis;

a temporal analysis;

a comparison of slope analysis;

moment analysis;

laterality analysis;

synchrony analysis;

volume analysis;

power function used to generate indices;

power spectrum analysis used to generate indices;

integral analysis; and derivative analysis.

16. The method of claim 15, wherein interpreting the results of the correlating procedure further comprises using one or more quantitative indices wherein at least one of the one or more quantitative indices corresponds to one of:

a coordinate index from a uniform anatomic space;

a subregion index;

a subnuclear index;

a first time index $T_p$ corresponding to a first moment of a signal response;

a second time index $\Delta$ corresponding to a second moment of a signal response;

a rate of signal change index;

an average time of response index;

a width of response index;

a tail index corresponding to a third moment of a signal response;

an R index;

an L index;

a fractional laterally index;

a correlation factor (r) index;

a volume index;

an exponent index;

a power spectrum index representing amplitudes of signal response harmonics and subharmonics computed using a power spectrum analysis;

an index corresponding to one or more amplitudes changes computed using an integral analysis of a signal response;

an index corresponding to a maximum rate of change of a signal response computed using a derivative analysis of a signal response; and an index corresponding to a time to achieve a maximum rate of change of a signal response computed using a derivative analysis of the signal response.

17. The method of claim 11, wherein the step of temporally segregating includes the step of segregating into an early phase waveform and a late phase waveform.

18. The method of claim 1, further comprising:

providing a known first set of indices;

measuring one or more signal responses in a subject;

generating a second set of indices by computing one or more index for each of the one or more signal responses; and comparing the second set of indices to the first set of indices.

19. The method of claim 18 wherein:

the step of providing the known first set of indices, includes the step of providing the known first set of indices to a processor; and the step of comparing the second set of indices to the first set of indices includes the steps of:

providing the second set of indices to the processor; and comparing the second set of indices to the first set of indices using the processor.

20. The method of claim 19 wherein the processor corresponds to a neural network processor.

21. The method of claim 1, wherein the experimental process comprises:

exposing a subject to at least one of a thermal, mechanical or chemical stimulus;

and measuring the response of the subject to the stimulus.

22. The method of claim 1, further comprising:

administering a treatment to the subject; and correlating the treatment to brain activity.

23. The method of claim 22, wherein the treatment corresponds to at least one of a drug/gene product, a surgical treatment, a radiation treatment, a behavioral treatment, and an acupuncture treatment.

24. The method of claim 1 wherein the step of interpreting the correlation result comprises:

correlating the signals from pain and reward brain regions; and comparing results of the correlation to a predetermined index.

25. A method of determining the effect of a compound on pain in a subject, the method comprising (a) administering to the a subject at least one of: a drug, a gene product, a biopharmaceutical, a virus, a gene, one or more receptors, and a neurochemical;

(b) applying a stimulus to the subject, wherein the stimulus elicits a response in one or more reward/aversion regions of the subject; and (c) measuring a brain response of the subject, wherein the measuring comprises:

noninvasively obtaining signals of central nervous system (CNS) activity from the subject;

(d) localizing signals to specific anatomical and functional CNS regions which participate in reward/aversion functions; and (e) correlating the signals in the reward/aversion brain region to a type of pain, thereby determining the effect of the compound on pain in the subject.

26. The method of claim 25 further comprising measuring the response of the subject over time.

27. The method of claim 26 wherein measuring the response of the subject over time comprises the steps of waiting a period of time and repeating steps (a)–(c).

28. The method of claim 26 wherein measuring the response of the subject over time comprises:

waiting a period of time;

administering a placebo to the subject;

applying a stimulus to the subject; and measuring an analgesic response of the subject.

29. A method for evaluating the efficacy of a treatment for pain comprising:

non-invasively obtaining signals of activity from at least two different reward/aversion regions of the CNS;

quantifying the signals to generate a first pattern of activity;

administering a candidate treatment, excluding acupuncture;

non-invasively obtaining signals of activity from the at least two different reward/aversion regions of the CNS;

quantifying the signals to generate a second pattern of activity;

obtaining physiological or psychophysical data from the subject; and correlating the first and second patterns and the physiological or psychophysical data, thereby evaluating the efficacy of the treatment for pain.

30. The method of claim 29, wherein one the reward/aversion regions is the NAc.

31. A method for evaluating the efficacy of a treatment for pain comprising:

non-invasively obtaining signals of activity from the nucleus accumbens (NAc);

quantifying the signals to generate a first pattern of activity;

administering a candidate treatment, excluding acupuncture;

non-invasively obtaining signals of activity from the NAc;

quantifying the signals to generate a second pattern of activity;

obtaining physiological or psychophysical data from the subject; and correlating the first and second patterns and the physiological or psychophysical data, thereby evaluating the efficacy of the treatment for pain.

* * * * *